US012758505B2

(12) United States Patent
Van Der Meel et al.

(10) Patent No.: US 12,758,505 B2
(45) Date of Patent: Oct. 13, 2026

(54) NUCLEIC ACID CONTAINING NANOPARTICLES

(71) Applicant: Bio-TRIP B.V., Eindhoven (NL)

(72) Inventors: Roy Van Der Meel, Eindhoven (NL); Willem J. M. Mulder, Eindhoven (NL); Ewelina Kluza, Zaltbommel (NL); Stijn Hofstraat, Eindhoven (NL); Tom Anbergen, Nijmegen (NL); Robby Cornelis Zwolsman, Eindhoven (NL); Henricus Marie Janssen, Eindhoven (NL); Pieter Michele Fransen, Boxtel (NL)

(73) Assignee: Bio-TRIP B.V., Eindhoven (NL)

( * ) Notice: Subject to any disclaimer, the term of this patent is extended or adjusted under 35 U.S.C. 154(b) by 273 days.

(21) Appl. No.: 18/572,415

(22) PCT Filed: Jun. 22, 2022

(86) PCT No.: PCT/EP2022/067073

§ 371 (c)(1),
(2) Date: Dec. 20, 2023

(87) PCT Pub. No.: WO2022/268913

PCT Pub. Date: Dec. 29, 2022

(65) Prior Publication Data

US 2024/0216291 A1 Jul. 4, 2024

(30) Foreign Application Priority Data

Jun. 22, 2021 (EP) .................................... 21180786

(51) Int. Cl.

| | |
|---|---|
| *A61K 9/51* | (2006.01) |
| *A61K 9/00* | (2006.01) |
| *A61K 31/713* | (2006.01) |
| *A61K 47/14* | (2017.01) |
| *A61K 47/18* | (2017.01) |
| *A61K 47/24* | (2006.01) |
| *A61K 47/28* | (2006.01) |

(52) U.S. Cl.

CPC .......... *A61K 9/5123* (2013.01); *A61K 9/0019* (2013.01); *A61K 31/713* (2013.01); *A61K 47/14* (2013.01); *A61K 47/18* (2013.01); *A61K 47/24* (2013.01); *A61K 47/28* (2013.01)

(58) Field of Classification Search

None

See application file for complete search history.

(56) References Cited

U.S. PATENT DOCUMENTS

| | | | |
|---|---|---|---|
| 2024/0391978 | A1 | 11/2024 | Van Der Meel et al. |
| 2025/0325491 | A1 | 10/2025 | Fransen et al. |
| 2026/0041638 | A1 | 2/2026 | Van Der Meel et al. |

FOREIGN PATENT DOCUMENTS

| | | | |
|---|---|---|---|
| CN | 113616602 | A | 11/2021 |
| WO | 2004/050062 | A1 | 6/2004 |
| WO | 2004/050062 | A2 | 6/2004 |
| WO | 2009/051451 | A2 | 4/2009 |
| WO | 2009/158678 | A1 | 12/2009 |
| WO | 2010/088537 | A2 | 8/2010 |
| WO | 2010/105209 | A1 | 9/2010 |
| WO | WO 2011044545 | A2 * | 4/2011 |
| WO | 2013/125769 | A1 | 8/2013 |
| WO | 2017/044424 | A1 | 3/2017 |
| WO | 2017/201076 | A1 | 11/2017 |
| WO | 2019/103998 | A2 | 5/2019 |
| WO | WO 2019138235 | A1 * | 7/2019 |
| WO | 2020/206231 | A1 | 10/2020 |
| WO | 2020/219833 | A1 | 10/2020 |
| WO | 2022/204053 | A1 | 9/2022 |

OTHER PUBLICATIONS

Tam et al., "Advances in Lipid Nanoparticles for siRNA Delivery," Pharmaceutics 2013, 5, 498-807 (Year: 2013).*

Notification of Transmittal of the International Search Report and Written Opinion for International Application No. PCT/EP2022/067073, mailed Sep. 22, 2022.

Berraondo, P. et al., "Cytokines in clinical cancer immunotherapy," British Journal of Cancer, vol. 120; 6-15 (2019).

Chen, W. et al., "Tethering Interleukin-22 to Apolipoprotein A-I Ameliorates Mice from Acetaminophen-induced Liver Injury," Theranostics, vol. 7; Issue 17; 4135-4148 (2017).

Christensen, D.J. et al., "Apolipoprotein E and Peptide Mimetics Modulate Inflammation by Binding the SET Protein and Activating Protein Phosphatase 2A," J Immunol, vol. 186; 2535-2542 (2011).

Dal Magro, R. et al., "Artifical apolipoprotein corona enables nanoparticle brain targeting," Nanomedicine: Nanotechnology Biology, and Medicine, vol. 14; 429-438 (2018).

Fioravanti, J. et al., "The Fusion Protein of IFN-α and Apolipoprotein A-I Crosses the Blood-Brain Barrier by a Saturable Transport Mechanism," J Immunol, vol. 188; 3988-3992 (2012).

Gao, A. et al., "Overview of recent advances in liposomal nanoparticle-based cancer immunotherapy," Acta Pharmacologica, vol. 40; 1129-1137 (2019).

Scodeller, P. and Asciutto, E.K., "Targeting Tumors Using Peptides," Molecules, vol. 25; 808; 24 pages (2020).

Vasquez, M. et al., "Antitumor effect of an adeno-associated virus expressing apolipoprotein A-1 fused to interferon alpha in an interferon alpha-resistant murine tumor model," Oncotarget, vol. 8; No. 3; 5247-5255 (2017).

(Continued)

*Primary Examiner* — Robert A Wax

(74) *Attorney, Agent, or Firm* — Hamilton, Brook, Smith & Reynolds, P.C.

(57) ABSTRACT

Herein disclosed are nanoparticles comprising a phospholipid, apolipoprotein and/or an apolipoprotein mimetic, sterol, cationic lipid or ionizable cationic lipid and a nucleic acid and compositions comprising such nanoparticles and a method for preparing such nanoparticles. The nanoparticles may be used as a medicament, such as in the treatment of a disease by stimulating or inhibiting an innate immune response.

38 Claims, 13 Drawing Sheets

Specification includes a Sequence Listing.

(56) References Cited

OTHER PUBLICATIONS

Zykova, A.A. et al., "Highly Immunogenic Nanoparticles Based on a Fusion Protein Comprising the M2e of Influenza A Virus and a Lipopeptide," Viruses, vol. 12; 1133; 11 pages (2020).
Crosby, N.M et al., "Anti-CD20 single chain variable antibody fragment-apolipoprotein A-1 chimera containing nanodisks promote targeted bioactive agent delivery to CD20-positive lymphomas," Biochem Cell Biol., vol. 93; No. 4; 343-350 (2015).
Hald Albertsen, C.H. et al., "The role of lipid components in lipid nanoparticles for vaccines and gene therapy," Advanced Drug Delivery Reviews, vol. 188; 114416; 17 pages (2022).
Marques, A.C. et al., "Lipid Nanoparticles Functionalized with Antibodies for Anticancer Drug Therapy," Pharmaceutics, vol. 15; 216; 22 pages (2023).
Pearce, A.K. et al., "Insights into Active Targeting of Nanoparticles in Drug Delivery: Advances in Clinical Studies and Design Considerations for Cancer Nanomedicine," Bioconjugate, vol. 30; 2300-2311 (2019).
Ren, X. et al., "Nanobody-Based Apolipoprotein E Immunosensor for Point-of-Care Testing," ACS Sens., vol. 2; 1267-1271 (2017).
Akinc, A. et al., "The Onpattro story and the clinical translation of nanomedicines containing nucleic acid-based drugs," Nature Nanotechnology, vol. 14; 1084-1087 (2019).
Khan, O.F. et al., "Ionizable Amphiphilic Dendrimer-Based Nanomaterials with Alkyl-Chain-Substituted Amines for Tunable siRNA Delivery to the Liver Endothelium In Vivo," Angew. Chem. Int. Ed., vol. 53; 14397-14401 (2014).
Khan, O.F. et al., "Dendrimer-Inspired Nanomaterials for the in Vivo Delivery of siRNA to Lung Vasculature," ACS Publications, Nano Lett., vol. 15; 3008-3016 (2015).
Kulkarni, J.A. et al., "On the Formation and Morphology of Lipid Nanoparticles Containing Ionizable Cationic Lipids and siRNA," ACS Nano, vol. 12; 4787-4795 (2018).
Maeki, M. et al., "Microfluidic technologies and devices for lipid nanoparticle-based RNA delivery," Journal of Controlled Release, vol. 344; 80-96 (2022).
Sebastiani, F. et al., "Apolipoprotein E Binding Drives Structural and Compositional Rearrangement of mRNA-Containing Lipid Nanoparticles," ACS Nano, vol. 15; 6709-6722 (2021).
Dalhaimer, P. et al., "Interactions of Apolipoprotein with Lipid-Based Nanoparticles," ACS Nano, vol. 17; 837-842 (2023).
Miroshnichenko, S. et al., "Apolipoprotein A-I Supports MSCs Survival under Stress Conditions," Int. J. Mol. Sci., vol. 21; 4062; 20 Pages (2020).
Miroshnichenko, S. et al., "Engineering a New IFN-ApoA-I Fusion Protein with Low Toxicity and Prolonged Action," Molecules, vol. 28; 8014; 18 Pages (2023).
Paunovska, K. et al., "The Extent to Which Lipid Nanoparticles Require Apolipoprotein E and Low-Density Lipoprotein Receptor for Delivery Changes with Ionizable Lipid Structure," Nano. Lett., vol. 22; 10025-10033 (2022).

* cited by examiner ( I )

Example 8: p = 2
Example 9: p = 1
(with oleoyl chains)

( III )

Example 10
R1 = n-C11
and p = 1

( IV )

Example 12
R1 = n-C11 and p = 2

( II )

Example 1: R1 = n-C11 and p = 2
Example 2: R1 = n-C10 and p = 2
Example 3: R1 = n-C9 and p = 2
Example 4: R1 = n-C11 and p = 1
Example 5: R1 = n-C10 and p = 1
Example 6: R1 = n-C9 and p = 1
Example 7: R1 = n-C17 and p = 1

( II )

Example 11: R1 = n-C11 and p = 3

( V )

Example 13: p = 2
Example 14: p = 1
Example 15: p = 0

Fig. 11

Table 1

| Formulation # | Phospholipid | Phospholipid (mg) | Dlin-MC3-DMA (mg) | Cholesterol (mg) | Triglycerides (mg) | Apo A1 (mg) | siRNA (mg) |
|---|---|---|---|---|---|---|---|
| 1 | POPC | 2.5 | 1.25 | 0.54 | 0 | 1 | 0.2 |
| 3 | POPC | 2.5 | 3.75 | 0.54 | 0 | 1 | 0.2 |
| 6 | DMPC | 2.5 | 2.5 | 0.54 | 0 | 1 | 0.2 |
| 7 | DMPC | 2.5 | 3.75 | 0.54 | 0 | 1 | 0.2 |
| 8 | DMPC | 2.5 | 5 | 0.54 | 0 | 1 | 0.2 |
| 9 | POPC | 2.5 | 1.25 | 1.35 | 0 | 1 | 0.2 |
| 10 | POPC | 2.5 | 2.5 | 1.35 | 0 | 1 | 0.2 |
| 11 | POPC | 2.5 | 3.75 | 1.35 | 0 | 1 | 0.2 |
| 12 | POPC | 2.5 | 5 | 1.35 | 0 | 1 | 0.2 |
| 14 | DMPC | 2.5 | 2.5 | 1.35 | 0 | 1 | 0.2 |
| 18 | POPC | 2.5 | 2.5 | 3.37 | 0 | 1 | 0.2 |
| 19 | POPC | 2.5 | 3.75 | 3.37 | 0 | 1 | 0.2 |
| 20 | POPC | 2.5 | 5 | 3.37 | 0 | 1 | 0.2 |
| 21 | DMPC | 2.5 | 1.25 | 3.37 | 0 | 1 | 0.2 |
| 22 | DMPC | 2.5 | 2.5 | 3.37 | 0 | 1 | 0.2 |
| 23 | DMPC | 2.5 | 3.75 | 3.37 | 0 | 1 | 0.2 |
| 24 | DMPC | 2.5 | 5 | 3.37 | 0 | 1 | 0.2 |
| 29 | DMPC | 2.5 | 1.25 | 0.54 | 5 | 1 | 0.2 |
| 31 | DMPC | 2.5 | 3.75 | 0.54 | 5 | 1 | 0.2 |
| 32 | DMPC | 2.5 | 5 | 0.54 | 5 | 1 | 0.2 |
| 33 | POPC | 2.5 | 1.25 | 1.35 | 5 | 1 | 0.2 |
| 34 | POPC | 2.5 | 2.5 | 1.35 | 5 | 1 | 0.2 |
| 35 | POPC | 2.5 | 3.75 | 1.35 | 5 | 1 | 0.2 |
| 39 | DMPC | 2.5 | 3.75 | 1.35 | 5 | 1 | 0.2 |
| 42 | POPC | 2.5 | 2.5 | 3.37 | 5 | 1 | 0.2 |
| 43 | POPC | 2.5 | 3.75 | 3.37 | 5 | 1 | 0.2 |
| 44 | POPC | 2.5 | 5 | 3.37 | 5 | 1 | 0.2 |
| 45 | DMPC | 2.5 | 1.25 | 3.37 | 5 | 1 | 0.2 |
| 46 | DMPC | 2.5 | 2.5 | 3.37 | 5 | 1 | 0.2 |
| 47 | DMPC | 2.5 | 3.75 | 3.37 | 5 | 1 | 0.2 |
| 48 | DMPC | 2.5 | 5 | 3.37 | 5 | 1 | 0.2 |
| 50 | POPC | 2.5 | 2.5 | 0.54 | 10 | 1 | 0.2 |
| 54 | DMPC | 2.5 | 2.5 | 0.54 | 10 | 1 | 0.2 |
| 55 | DMPC | 2.5 | 3.75 | 0.54 | 10 | 1 | 0.2 |
| 56 | DMPC | 2.5 | 5 | 0.54 | 10 | 1 | 0.2 |
| 59 | POPC | 2.5 | 3.75 | 1.35 | 10 | 1 | 0.2 |
| 60 | POPC | 2.5 | 5 | 1.35 | 10 | 1 | 0.2 |
| 67 | POPC | 2.5 | 3.75 | 3.37 | 10 | 1 | 0.2 |
| 68 | POPC | 2.5 | 5 | 3.37 | 10 | 1 | 0.2 |
| 71 | DMPC | 2.5 | 3.75 | 3.37 | 10 | 1 | 0.2 |
| 72 | DMPC | 2.5 | 5 | 3.37 | 10 | 1 | 0.2 |

Fig. 11 (continued)

| Formulation # | Phospholipid (mol%) | Dlin-MC3-DMA | Cholesterol (mol %) | ApoA1 (mol%) | siRNA (mol%) | Triglycerides (mol%) |
|---|---|---|---|---|---|---|
| 1 | 49% | 29% | 21% | 0.50% | 0.18% | 0% |
| 3 | 31% | 55% | 13% | 0.32% | 0.11% | 0% |
| 6 | 41% | 43% | 15% | 0.37% | 0.13% | 0% |
| 7 | 34% | 53% | 13% | 0.31% | 0.11% | 0% |
| 8 | 29% | 60% | 11% | 0.26% | 0.09% | 0% |
| 9 | 37% | 22% | 40% | 0.38% | 0.14% | 0% |
| 10 | 31% | 36% | 33% | 0.31% | 0.11% | 0% |
| 11 | 26% | 46% | 28% | 0.26% | 0.10% | 0% |
| 12 | 22% | 53% | 24% | 0.23% | 0.08% | 0% |
| 14 | 33% | 35% | 31% | 0.30% | 0.11% | 0% |
| 18 | 21% | 24% | 55% | 0.21% | 0.08% | 0% |
| 19 | 18% | 33% | 49% | 0.19% | 0.07% | 0% |
| 20 | 17% | 39% | 44% | 0.17% | 0.06% | 0% |
| 21 | 26% | 14% | 61% | 0.23% | 0.08% | 0% |
| 22 | 23% | 24% | 53% | 0.21% | 0.07% | 0% |
| 23 | 20% | 32% | 48% | 0.18% | 0.07% | 0% |
| 24 | 18% | 38% | 43% | 0.17% | 0.06% | 0% |
| 29 | 21% | 11% | 8% | 0.19% | 0.07% | 60% |
| 31 | 17% | 27% | 6% | 0.16% | 0.06% | 49% |
| 32 | 16% | 33% | 6% | 0.14% | 0.05% | 45% |
| 33 | 17% | 10% | 18% | 0.17% | 0.06% | 55% |
| 34 | 15% | 18% | 16% | 0.16% | 0.06% | 50% |
| 35 | 14% | 25% | 15% | 0.14% | 0.05% | 46% |
| 39 | 16% | 25% | 15% | 0.14% | 0.05% | 45% |
| 42 | 12% | 15% | 33% | 0.13% | 0.05% | 40% |
| 43 | 12% | 20% | 31% | 0.12% | 0.04% | 37% |
| 44 | 11% | 26% | 29% | 0.11% | 0.04% | 35% |
| 45 | 15% | 8% | 35% | 0.13% | 0.05% | 42% |
| 46 | 14% | 14% | 32% | 0.12% | 0.04% | 39% |
| 47 | 13% | 20% | 30% | 0.12% | 0.04% | 37% |
| 48 | 12% | 25% | 28% | 0.11% | 0.04% | 34% |
| 50 | 11% | 13% | 5% | 0.11% | 0.04% | 71% |
| 54 | 12% | 13% | 5% | 0.11% | 0.04% | 70% |
| 55 | 11% | 18% | 4% | 0.10% | 0.04% | 66% |
| 56 | 11% | 23% | 4% | 0.10% | 0.04% | 62% |
| 59 | 10% | 17% | 10% | 0.10% | 0.04% | 63% |
| 60 | 9% | 22% | 10% | 0.09% | 0.03% | 59% |
| 67 | 8% | 15% | 22% | 0.09% | 0.03% | 54% |
| 68 | 8% | 19% | 21% | 0.08% | 0.03% | 52% |
| 71 | 9% | 15% | 22% | 0.08% | 0.03% | 54% |
| 72 | 9% | 19% | 21% | 0.08% | 0.03% | 51% |

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: ApoA1 mimetic peptide 18A

<400> SEQUENCE: 1

Asp Trp Leu Lys Ala Phe Tyr Asp Lys Val Ala Glu Lys Leu Lys Glu
1               5                   10                  15

Ala Phe


<210> SEQ ID NO 2
<211> LENGTH: 18
<212> TYPE: PRT
<213> ORGANISM: Artificial Sequence
<220> FEATURE:
<223> OTHER INFORMATION: ApoA1 mimetic peptide 2F
<220> FEATURE:
<221> NAME/KEY: SITE
<222> LOCATION: (1)..(1)
<223> OTHER INFORMATION: acetamide capped
<220> FEATURE:
<221> NAME/KEY: SITE
<222> LOCATION: (18)..(18)
<223> OTHER INFORMATION: amide-group

<400> SEQUENCE: 2

Asp Trp Leu Lys Ala Phe Tyr Asp Lys Val Ala Glu Lys Leu Lys Glu
1               5                   10                  15

Ala Phe
```

NUCLEIC ACID CONTAINING NANOPARTICLES

This application is the U.S. National Stage of International Application No. PCT/EP2022/067073, filed Jun. 22, 2022, which designates the U.S., published in English, and claims priority under 35 U.S.C. § 119 or 365(c) to EP Application No. 21180786.2, filed Jun. 22, 2021. The entire teachings of the above applications are incorporated herein by reference.

FIELD OF THE INVENTION

The invention relates to the field of nucleic acid therapeutics and provides a novel and inventive nanoparticle for the intracellular delivery of nucleic acids at a target site. The invention further relates to methods of treatment using the nanoparticle, for example in the treatment of a disease by stimulating or inhibiting an innate immune response. The invention further relates to an in vivo, in vitro or ex vivo method for introducing a nucleic acid in a cell using the nanoparticles.

INCORPORATION BY REFERENCE OF MATERIAL IN ASCII TEXT FILE

This application incorporates by reference the Sequence Listing contained in the following ASCII text file:

a) File name: 62911000001_Sequence_Listing.txt; created Dec. 12, 2023, 961 Bytes in size.

BACKGROUND OF THE INVENTION

Nucleic acid therapeutics (NAT) such as small antisense oligonucleotides (ASO), small interfering RNA (siRNA), messenger RNA (mRNA) and other types are a revolutionary new class of drugs that have the potential to regulate gene expression. In recent years, several nucleic acid-based drug products for in vivo applications have been approved including ASOs, N-acetylgalactosamine (GalNAc)-siRNA conjugates, lipid nanoparticles (LNP) containing siRNA or mRNA and a number of viral vectors containing plasmid DNA (pDNA). In addition, there are several NAT in late-stage clinical trials. Furthermore, several genetically engineered ex vivo cell therapy drug products have been approved.

The therapeutic application of nucleic acids following parenteral administration is challenging. Although nucleic acid types vary in size and physicochemical properties, their common features include their large, macromolecular size and negative charge. As a result, upon systemic administration, nucleic acids are rapidly cleared from the circulation due to kidney filtration and nuclease degradation. In addition, NAT act intracellularly but cannot readily pass cellular membranes. Finally, administration of exogenous nucleic acids provokes an immune response. While this can be advantageous (e.g., for vaccine development), usually this contributes to nucleic acids' rapid clearance and adverse effects.

To overcome these challenges, all nucleic acid therapeutics rely on chemical modifications and/or nanotechnology-based delivery systems. All approved NAT are dependent on chemical modifications and/or nanotechnology platforms to facilitate their intracellular delivery and subsequently induce therapeutic effects following parenteral administration:

1) ASOs are heavily chemically modified to increase their stability, reduce immunostimulatory effects and increase their efficacy. They are administered subcutaneously to target hepatocytes or intrathecally to target cells in the central nervous system.
2) GalNAc-siRNA conjugates are similarly modified as ASOs and are administered subcutaneously. The GalNAc moiety ensures asialoglycoprotein receptor-mediated uptake in hepatocytes.
3) Lipid nanoparticles (LNPs) are ~50-100 nm in diameter and can be administered systemically, intradermally or intramuscularly. Following systemic administration, LNPs efficiently accumulate in hepatocytes providing opportunities for gene silencing (siRNA) or protein production (mRNA). Following intradermal or intramuscular administration, LNPs are taken up by immune cells such as antigen presenting cells which can be exploited for vaccine purposes. LNPs are the current golden standard for mRNA therapeutics and will likely also become the standard delivery platform for gene editing applications in vivo. LNPs contain synthetic polyethylene glycol (PEG)-conjugated lipids which have been associated with hypersensitivity reactions and or anaphylaxis.
4) Viral delivery systems such as adenoviruses, lentiviruses or adeno-associated virus (AAV) vectors are effective vehicles to deliver DNA. Viral vectors are characterized by their limited payload capacity and immunogenicity. However, in immune-privileged tissues such as the eye, viral vectors constitute the current golden standard for NAT. Viral vectors are extensively used for ex vivo therapeutics (e.g., CAR T) or are administered intravenously to target cells in the liver, intravitreally/subretinally to target cells in the retina or intramuscularly for vaccine purposes.

With the exception of viral vector- or LNP-mRNA-based vaccines, the majority of approved nucleic acid therapeutics is developed for other indications than immunotherapy. Delivering therapeutic nucleic acids to the myeloid compartment therefore remains a challenge. Furthermore, chemical modifications of nucleic acid molecules or viral delivery inherently have the risk of unwanted activation of the immune system, resulting in degradation or clearance of the NAT.

For example, nanoparticles carrying nucleic acids have been described for example in WO2009127060A1 which describes the use of cationic lipids combined with non-cationic lipids and nucleic acids. The cationic lipids neutralize the nucleic acid, allowing the formation of nanoparticles which may be used for non-targeted delivery of the nucleic acids in a subject. A drawback of these nanoparticles is that they are not capable of targeting the myeloid compartment.

Other systems, for example in WO2019103998A2, describe nanobiologics that are able to target the myeloid compartment, the nanobiologics comprising phospholipids and ApoA1 and a small molecule drug. The drawback of these nanobiologics is that due to their hydrophobic core they do not allow the incorporation of polar structures such as nucleic acids, e.g. DNA and RNA.

Therefore, there is a need for improved delivery systems for therapeutic nucleic acids to the myeloid compartment.

SUMMARY OF THE INVENTION

Present inventors were the first to develop a nanoparticle that allows delivery of a nucleic acid cargo to the myeloid compartment. More particularly, present inventors have developed stable, lipid-based nano-sized formulations (diameter ~10-200 nm) comprising an apolipoprotein and/or apolipoprotein mimetic, a phospholipid, a sterol, a cationic or ionizable cationic lipid and a nucleic acid, such as siRNA or mRNA. Without wishing to be bound by any theory, present inventors believe that the core of the nanoparticle comprises an assembly of nucleic acid interacting with the (ionizable) cationic lipid, wherein this core is packaged and buried within an outer protective surface or lipid shell comprising the apolipoprotein and/or an apolipoprotein mimetic, the phospholipid and the sterol, which functions as a surface barrier.

The nucleic acid is properly and stably incorporated into the nanoparticles of present invention, without the need of synthetic (non-natural) hydrophilic polymers or (lipid) conjugates of such polymers, such as polyethylene-glycol (PEG).

Furthermore, the nanoparticles of present invention also do not uncontrollably aggregate and/or coalesce, even when such synthetic (non-natural) hydrophilic polymers or (lipid) conjugates of such polymers are absent.

In addition, the nanoparticles of present invention have a targeting capability towards myeloid cells and other cells associated with the immune system, as a result of the presence of apolipoproteins and/or apolipoprotein mimetics at the outer surface of the nanoparticle.

Moreover, the nanoparticles as taught herein are stable, have a low toxicity or are non-toxic, have a high nucleic acid retention and a high nucleic acid activity.

Present inventors further have developed a controlled formulation process for successfully incorporating a nucleic acid in an apolipoprotein and/or apolipoprotein mimetic-based nanoparticle.

Accordingly, a first aspect of the invention provides a nanoparticle comprising:

a core surrounded by a surface layer, wherein:

the core comprises a nucleic acid and a cationic or ionizable cationic lipid; and the surface layer comprises:

- a phospholipid,
- a sterol, and
- an apolipoprotein or an apolipoprotein mimetic or a combination thereof.

The invention further relates to a composition comprising the nanoparticle according to the invention and a physiologically acceptable carrier.

The invention further relates to the nanoparticle or the composition according to the invention for use as a medicament.

The invention further relates to the nanoparticle or the composition according to the invention for use in the treatment of a disease by stimulating or inhibiting an innate immune response.

The invention further relates to a method for producing a nanoparticle, comprising the step of:

a) rapid mixing of lipid components in organic solvent with a nucleic acid in an aqueous buffer to produce lipid nanoparticles, wherein the lipid components comprise a phospholipid, a sterol, a cationic lipid or ionizable cationic lipid, and optionally a filler material, preferably a triglyceride, at a pH of 5.0 or lower; and b) rapid mixing of the lipid nanoparticles (as prepared under a)) with an apolipoprotein, an apolipoprotein mimetic, or a combination thereof to produce the nanoparticle at a pH between 6.0 and 8.0.

The invention further relates to an in vitro or ex vivo method for introducing a nucleic acid in a cell, the method comprising contacting the nanoparticle or the composition according to the invention with a cell.

The invention further relates to the nanoparticle according to the invention obtainable or obtained by the method according to the invention.

The invention further relates to an in vivo method for introducing a nucleic acid in a cell, the method comprising contacting the nanoparticle or the composition according to the invention with a cell.

The invention further relates to the nanoparticle or the composition according to the invention for use in the in vivo delivery of a nucleic acid to a subject.

The invention further relates to a method for the in vivo delivery of a nucleic acid, the method comprising administering the nanoparticle or the composition according to the invention to a subject.

The invention further relates to a method for treating a disease or disorder in a subject in need thereof by stimulating or inhibiting an innate immune response, the method comprising administering a therapeutically effective amount of the nanoparticle or the composition according to the invention to the subject.

BRIEF DESCRIPTION OF THE FIGURES

FIG. 11: Table 1: illustrative formulations of the library of 72 siRNA aNP formulations.

DETAILED DESCRIPTION OF THE INVENTION

Figure 1:
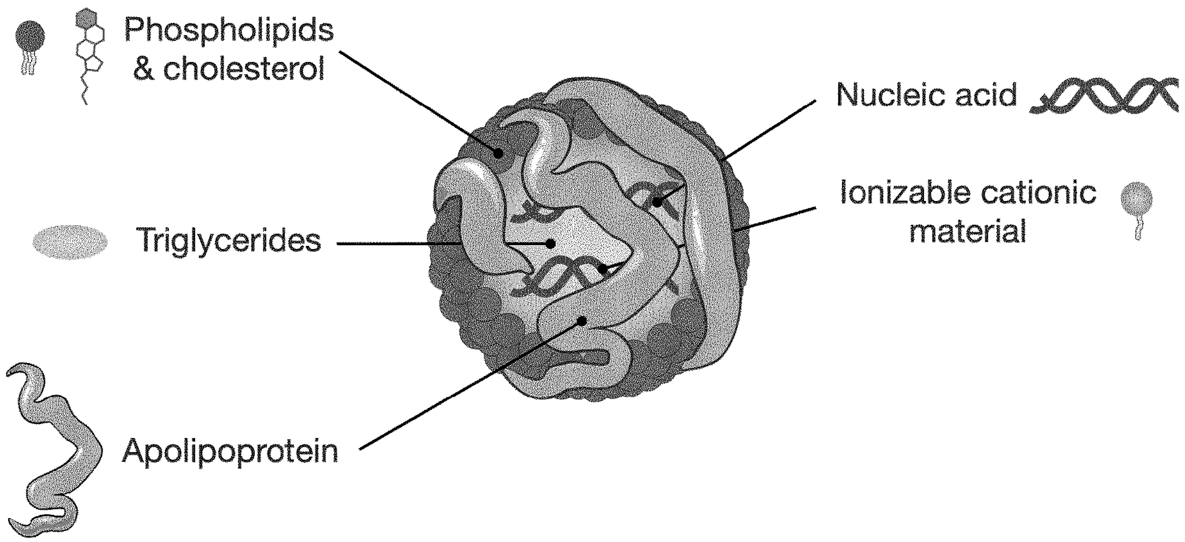
FIG. 1: Schematic overview of apolipoprotein lipid nanoparticle (aNP) platform technology according to certain embodiments of the invention, for nucleic acid delivery. Without wishing to be bound by any theory, such RNA-aNPs are believed to be composed of a hydrophobic core containing optional filler material (e.g. triglycerides) and nucleic acids, such as RNA, complexed by (ionizable) cationic lipids. The hydrophobic core is enclosed and shielded by a surface layer or barrier, possibly a monolayer, containing phospholipids and sterols. The lipid nanoparticle's surface also comprises apolipoproteins for structural integrity, to prevent aggregation, to provide particle stability, to provide natural stealth and/or to facilitate interactions with immune cells.

As used herein, the singular forms "a", "an", and "the" include both singular and plural referents unless the context clearly dictates otherwise.

The terms "comprising", "comprises" and "comprised of" as used herein are synonymous with "including", "includes", "containing", or "contains", and are inclusive or open-ended and do not exclude additional, non-recited members, elements or method steps. The terms also encompass "constituted of", "consists in", "consisting of", and "consists of", and also the terms "consisting essentially of", "consisting essentially in" and "consists essentially of", which enjoy well-established meanings in patent terminology.

The recitation of numerical ranges by endpoints includes all integer numbers and, where appropriate, fractions subsumed within the respective ranges, as well as the recited endpoints. This applies to numerical ranges irrespective of whether they are introduced by the expression "from . . . to . . . " or the expression "between . . . and . . . " or another expression. Any numerical range recited herein is intended to include all sub-ranges subsumed therein.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

As used herein, the term "and/or" when used in a list of two or more items, means that any one of the listed items can be employed by itself or any combination of two or more of the listed items can be employed. For example, if a list is described as comprising group A, B, and/or C, the list can comprise A alone, B alone, C alone, A and B in combination, A and C in combination, B and C in combination, or A, B, and C in combination.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation or meaning is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Similarly, it should be appreciated that in the description of illustrative embodiments of the invention, various features of the invention are sometimes grouped together in a single embodiment, figure, or description thereof for the purpose of streamlining the disclosure and aiding in the understanding of one or more of the various inventive aspects.

The term "in vitro" is well understood in the art and may in particular refer to experimentation or measurements conducted using components of an organism that have been isolated from their natural conditions.

As used herein, the term "ex vivo" is well understood in the art and may in particular refer to experimentation or measurements done in or on tissue from an organism in an external environment with minimal alteration of natural condition.

The terms "nucleic acid", "nucleic acid molecule" and "polynucleotide" are well understood in the art. By means of further guidance, the terms typically refer to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U), which are widespread in naturally-occurring nucleic acids, other naturally-occurring bases (e.g., xanthine, inosine, hypoxanthine), as well as chemically or biochemically modified (e.g., methylated), non-natural or derivatised bases. Exemplary modified nucleobases include, without limitation, 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as, without limitation, 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoro-arabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used in this context particularly encompasses lower hydrocarbon moieties, e.g., $C_1$-$C_4$ linear or branched, saturated or unsaturated hydrocarbon, such as methyl, ethyl, ethenyl, propyl, 1-propenyl, 2-propenyl, and isopropyl.

Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

In certain embodiments, the terms may be intended to include DNA molecules and RNA molecules, as well as locked nucleic acid (LNA), bridged nucleic acid (BNA), morpholino or peptide nucleic acid (PNA). A nucleic acid (molecule) may be any nucleic acid (molecule), it may for example be single-stranded or double-stranded.

The terms "subject" or "individual" or "animal" or "patient" or "mammal", which may be used interchangeably, are well understood in the art and may in particular refer to any subject, particularly a mammalian subject, for whom diagnosis, prognosis, or therapy is desired. The terms may for example refer to animals, preferably warm-blooded animals, more preferably vertebrates, even more preferably mammals, still more preferably primates, and may specifically include human patients and non-human mammals and primates. Preferred patients are human subjects including both genders and all age categories thereof. Mammalian subjects include humans, domestic animals, farm animals, and zoo-, sports-, or pet-animals such as dogs, cats, guinea pigs, rabbits, rats, mice, horses, cattle, cows, bears, and so on. As defined herein a subject may be alive or dead. Samples can be taken from a subject post-mortem, i.e. after death, and/or samples can be taken from a living subject. Preferably, the subject is a human.

The terms "treat" or "treatment" are well understood in the art and may in particular encompass both the therapeutic treatment of an already developed disease or condition, as well as prophylactic or preventive measures, wherein the aim is to prevent or lessen the chances of incidence of an undesired affliction, such as to prevent occurrence, development and progression of a disease or disorder. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

When used herein, the term "nanoparticle" in particular refers to a small particle, e.g. in the range of about 10 nm to about 200 nm in diameter which may be used to deliver a payload to a target, e.g. an organ or cell in a subject.

When used herein, the term "targeting", when referring to targeting a cell (e.g. a target cell such as but not limited to a myeloid cell) or targeting a tissue or organ should be understood to mean bringing in proximity of the intended cell, organ or tissue, or to enrich in the proximity of the intended cell, organ or tissue. This implies that when targeting an intended cell, organ or tissue, on average more nanoparticles are in proximity of the intended cell, organ or tissue as can be expected based on random or natural distribution of the particle. In proximity herein means being located such that the nanoparticle can interact with the cell (or tissue or organ) to deliver its payload (nucleic acid).

The term "myeloid cell" is well understood in the art and may particularly refer to blood cells that are derived from a common progenitor cell for megakaryocytes, granulocytes, monocytes, erythrocytes. Myeloid cells are a major cellular compartment of the immune system comprising monocytes, dendritic cells, tissue macrophages, and granulocytes. The term myeloid compartment, when used herein, refers to the totality of myeloid cells in an organism.

The term "alkyl" by itself or as part of another substituent refers to a hydrocarbyl group of formula $C_nH_{2n+1}$ wherein n is a number greater than or equal to 1. Alkyl groups may be linear or branched and may be substituted as indicated herein. Generally, alkyl groups of this invention comprise from 1 to 18 carbon atoms, preferably from 1 to 17 carbon atoms, preferably from 1 to 15 carbon atoms, preferably from 1 to 6 carbon atoms, preferably from 1 to 5 carbon atoms, preferably from 1 to 4 carbon atoms, more preferably from 1 to 3 carbon atoms, still more preferably 1 to 2 carbon atoms. When a subscript is used herein following a carbon atom, the subscript refers to the number of carbon atoms that the named group may contain. For example, the term "$C_{1-6}$-alkyl", as a group or part of a group, refers to a hydrocarbyl group of formula —$C_nH_{2n+1}$ wherein n is a number ranging from 1 to 6. Thus, for example, "$C_{1-6}$-alkyl" includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers. For example, "$C_{1-5}$alkyl" includes all includes all linear or branched alkyl groups with between 1 and 5 carbon atoms, and thus includes methyl, ethyl, n-propyl, i-propyl, butyl and its isomers (e.g. n-butyl, i-butyl and t-butyl); pentyl and its isomers. For example, "$C_{1-4}$alkyl" includes all linear or branched alkyl groups with between 1 and 4 carbon atoms, and thus includes methyl, ethyl, n-propyl, i-propyl, butyl and its isomers (e.g. n-butyl, i-butyl and t-butyl). For example "$C_{1-3}$alkyl" includes all linear or branched alkyl groups with between 1 and 3 carbon atoms, and thus includes methyl, ethyl, n-propyl, i-propyl.

When the suffix "ene" is used in conjunction with an alkyl group, i.e. "alkylene", this is intended to mean the alkyl group as defined herein having two single bonds as points of attachment to other groups. As used herein, the term "$C_{1-6}$alkylene", by itself or as part of another substituent, refers to $C_{1-6}$alkyl groups that are divalent, i.e., with two single bonds for attachment to two other groups. Alkylene groups may be linear or branched and may be substituted as indicated herein. Non-limiting examples of alkylene groups include methylene (—$CH_2$—), ethylene (—$CH_2$—$CH_2$—), methylmethylene (—$CH(CH_3)$—), 1-methyl-ethylene (—$CH(CH_3)$—$CH_2$—), n-propylene (—$CH_2$—$CH_2$—$CH_2$—), 2-methylpropylene (—$CH_2$—$CH(CH_3)$—$CH_2$—), 3-methylpropylene (—$CH_2$—$CH_2$—$CH(CH_3)$—), n-butylene (—$CH_2$—$CH_2$—$CH_2$—$CH_2$—), 2-methylbutylene (—$CH_2$—$CH(CH_3)$—$CH_2$—$CH_2$—), 4-methylbutylene (—$CH_2$—$CH_2$—$CH_2$—$CH(CH_3)$—), pentylene and its chain isomers, hexylene and its chain isomers.

The term "alkenyl" as a group or part of a group, refers to an unsaturated hydrocarbyl group, which may be linear, or branched, comprising one or more carbon-carbon double bonds. When a subscript is used herein following a carbon atom, the subscript refers to the number of carbon atoms that the named group may contain. For example, the term "$C_{2-6}$alkenyl" refers to an unsaturated hydrocarbyl group, which may be linear, or branched comprising one or more carbon-carbon double bonds and comprising from 2 to 6 carbon atoms. For example, $C_{2-4}$alkenyl includes all linear, or branched alkenyl groups having 2 to 4 carbon atoms. Examples of $C_{2-6}$alkenyl groups are ethenyl, 2-propenyl, 2-butenyl, 3-butenyl, 2-pentenyl and its isomers, 2-hexenyl and its isomers, 2,4-pentadienyl, and the like.

The term "aryl", as a group or part of a group, refers to a polyunsaturated, aromatic hydrocarbyl group having a single ring (i.e. phenyl) or multiple aromatic rings fused together (e.g. naphthyl), or linked covalently, typically containing 6 to 24 carbon atoms, preferably 6 to 12 atoms; preferably 6 to 10, wherein at least one ring is aromatic. Examples of suitable aryl include $C_{6-10}$aryl, more preferably $C_{6-8}$aryl. Non-limiting examples of $C_{6-12}$aryl comprise phenyl; biphenylyl; biphenylenyl; or 1- or 2-naphthanelyl; 1-, 2-, 3-, 4-, 5- or 6-tetralinyl (also known as "1,2,3,4-tetrahydronaphthalene); 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl; 1,2,3,4-tetrahydronaphthyl; and 1,4-dihydronaphthyl; 1-, 2-, 3-, 4- or 5-pyrenyl. When the suffix "ene" is used in conjunction with an aryl group; i.e. arylene, this is intended to mean the aryl group as defined herein having two single bonds as points of attachment to other groups. Suitable "$C_{6-12}$arylene" groups include 1,4-phenylene, 1,2-phenylene, 1,3-phenylene, biphenylylene, naphthylene, indenylene, 1-, 2-, 5- or 6-tetralinylene, and the like. Where at least one carbon atom in an aryl group is replaced with a heteroatom, the resultant ring is referred to herein as a heteroaryl ring. The heteroatom may be selected from the group consisting of O, N, P and S; preferably O or N.

The term "alkylene-aryl", as a group or part of a group, means a alkylene as defined herein, wherein at least one hydrogen atom is replaced by at least one aryl as defined herein. Alkylene-aryl groups typically contain 7 to 25 carbon atoms. Non-limiting examples of alkylene-aryl group include benzyl, phenethyl, dibenzylmethyl, methylphenylmethyl, 3-(2-naphthyl)-butyl, and the like. The term "arylene-alkyl", as a group or part of a group, means a arylene as defined herein, wherein at least one hydrogen atom is replaced by at least one alkyl group as defined herein. Arylene-alkyl groups typically contain 7 to 25 carbon atoms.

Ester, amide, carboxylic acid and alcohol groups are defined hereunder, where Rp represents a hydrogen atom or a cyclic, linear or branched alkyl or alkylene groups. In groups that contain more than one Rp element, then these elements can be independently selected. An ester (functional) group or moiety as indicated in this document is to be understood as a group according to the formula: —C(O)—O—. An amide (functional) group or moiety as indicated in this document is to be understood as a group according to the formula: —NRp-C(O)—. A carboxylic acid (functional) group or moiety as indicated in this document is to be understood as a moiety or group according to the formula: —C(O)OH. An alcohol (or hydroxy) functional group or moiety as indicated in this document is to be understood as a group according to the formula: —OH.

The current invention constitutes a nanoparticle platform technology suitable for NAT delivery to the myeloid cell compartment. The nanoparticles described herein are (phospho)lipid-based nanoparticles stabilized by apolipoproteins and/or apolipoprotein mimetics that protect the NAT payload in the circulation by preventing it from degradation and rapid clearance. At the same time, the nanoparticles reduce NAT's immunostimulatory-related adverse effects by limiting unwanted interactions with components in the blood. In addition, the invention enables efficient nucleic acid therapeutics delivery to the myeloid cell compartment in lymphoid organs, such as the bone marrow and the spleen, for effective immunotherapy.

Nanoparticles as described herein are lipid-based nanosized formulations (diameter ~10-200 nm, such as in certain embodiments ~30-200 nm) with a hydrophobic core and apolipoproteins and/or an apolipoprotein mimetics covering the outer surface. Without being bound to theory, present inventors believe that the core of the nanoparticle comprises an assembly of nucleic acid interacting with the (ionizable) cationic lipid, wherein this core is packaged and buried within an outer protective surface or lipid shell comprising the apolipoprotein and/or an apolipoprotein mimetic, the phospholipid and the sterol, that may function as a surface layer or barrier. The apolipoproteins and/or an apolipoprotein mimetic may use hydrophobic and/or charged (ionic) interactions to interact with the other components of the outer protective surface. The outer protective surface can possibly also comprise some (ionizable) cationic lipids that have not complexed with the nucleic acid component. FIG. 1 provides a schematic overview of the impression of the nanoparticle of the invention. Apolipoproteins are helical proteins with inherent affinity for lipid layers due to their amphiphilic character. There are several classes of apolipoproteins, and all can be used as a structural component for nanoparticle formulations. Apolipoprotein integration affects the nanoparticle's physicochemical properties and shelf-life by providing structural stability. Furthermore, the presence of apolipoprotein modulates the biological behaviour of the nanoparticle. For example, apolipoprotein A1 interacts with cells via scavenger receptor class B type 1 (SRB1) and ATP-binding cassette transporter ABCA1. This increases interactions of the nanoparticle with myeloid cells in lymphoid organs.

Phospholipids in the nanoparticle formulation, due to their amphiphilic character, accumulate at the interface between the hydrophobic core and the aqueous solvent, effectively forming a lipid monolayer membrane, or a surface layer or barrier. For biological uses, single or multiple phospholipid types are used, because of their inherent biocompatibility and net neutral charge. Optionally, mol percentages (~1-95 mol %; relative to the total amount of employed phospholipid) of charged lipids, such as 1,2-Dioleoyl-3-trimethylammonium propane (DOTAP) or 1,2-dioleoyl-sn-glycero-3-phosphate (18PA), can be added to give the entire formulation a specific charged character.

The nanoparticles as taught herein are engineered to complex nucleic acids, which are hydrophilic in nature, thus helper molecules are needed to draw the nucleic acids into the hydrophobic nanoparticle core. To this end, cationic hydrophobic molecules are employed. The cationic group can complex with the anionic phosphate groups in the sugar phosphate backbone via ionic interactions. The hydrophobic part of the helper molecule forms a shell around the hydrophilic nucleic acid molecule. The cationic helper molecules can be either permanently charged or ionizable. They comprise a wide variety of molecules, commercially available or synthesized in house, but they need to adhere to two general criteria: 1) A positively charged group to enable complexation with the negatively charged sugar phosphate backbone. 2) A hydrophobic part to form a hydrophobic shell and enable integration in the nanoparticle core. The content of cationic material in nanoparticle formulations may range from a cationic-to-anionic ratio of 1:1 to 25:1. This ratio, often referred to as the N/P (nitrogen/phosphate) ratio, is based on the number of positive charges in the (ionizable) cationic lipid (often nitrogen-based) versus the number of negative charges in the nucleic acid payload (usually phosphate). Accordingly, the N/P ratio is the ratio between the cumulative molar amount of cationic and/or ionizable groups in the cationic or ionizable lipid component(s) (N) and the cumulative molar amount of phosphate groups in the nucleic acid component(s) (P). In particular embodiments, the N/P ratio of the nanoparticles as taught herein is from 1 to 25, from 1 to 20, from 1 to 15, from 1 to 12, from 1 to 9, from 1 to 6, or from 1 to 3. For example, the N/P ratio of the nanoparticles as taught herein may be 3, 6, 9 or 12.

Besides nucleic acids and cationic helper molecules, additional hydrophobic molecules (e.g. filler material (i.e. filler or filler molecules)) can be included in the core of nanoparticle formulations. Their main application is to alter nanoparticle physicochemical properties and/or improve stability.

Nanoparticles containing therapeutic nucleic acids are expected to precisely regulate gene expression in the myeloid cell compartment and thereby modulating the immune response. A major advantage of the nanoparticle platform technology as taught herein is the possibility to exchange the nucleic acid payload without altering the aNP-formulation's biological behaviour and interactions. Nanoparticles containing therapeutic nucleic acids can therefore be implemented as immunotherapies that promote the immune response to treat e.g., cancer or infectious diseases, or to dampen the immune response to treat e.g., autoimmune diseases or during organ transplantation.

Therefore, in a first aspect, the invention relates to a nanoparticle comprising, consisting essentially of or consisting of:

- an apolipoprotein and/or an apolipoprotein mimetic;
- a phospholipid;
- a sterol;
- a cationic lipid, an ionizable cationic lipid or a combination thereof;
- a nucleic acid; and
- optionally, a filler material.

Without being bound to theory, present inventors believe that the nanoparticles described herein have an outer layer comprising mainly apolipoprotein and/or an apolipoprotein mimetic, phospholipid and sterol, and a core comprising cationic or ionizable cationic lipid and the cargo, namely the nucleic acid. More particularly, as described elsewhere in the present specification, the core of the nanoparticle as taught herein comprises an assembly of nucleic acid interacting with the (ionizable) cationic lipid, wherein this core of the nanoparticle of present invention is surrounded by a lipid shell comprising, consisting essentially of or consisting of apolipoprotein and/or an apolipoprotein mimetic, phospholipid and sterol.

The nanoparticles can be used to deliver the cargo to its intended destination, e.g. a cell, tissue or organ. Preferably the nucleic acid cargo is delivered intracellularly in the target cell, tissue or organ.

In particular embodiments, the nucleic acid is located within (i.e. on the inside) of the nanoparticle. In other words, in particular embodiments, the nucleic acid is not located at the outer surface of the nanoparticle and/or is not exposed to the surroundings of the nanoparticle.

In particular embodiments, the apolipoprotein and/or apolipoprotein mimetic is located at the outer surface of the nanoparticle and/or is exposed to the surroundings of the nanoparticle.

In particular embodiments, the invention relates to a nanoparticle comprising a core surrounded by a surface layer, wherein:

- the core comprises, consists essentially of, or consists of a nucleic acid and a cationic or ionizable cationic lipid; and
- the surface layer comprises, consists essentially of, or consists of:
  - a phospholipid,
  - a sterol, and
  - an apolipoprotein or an apolipoprotein mimetic or a combination thereof.

It was found that by using an apolipoprotein and/or an apolipoprotein mimetic, for example ApoA1, the nanoparticle can successfully be targeted to the myeloid compartment, in vitro, ex vivo and in vivo. This has the advantage that immune progenitor cells can be target by drugs in order to stimulate or inhibit an innate immune response. There are several therapeutical applications where such use is deemed beneficial, such as but not limited to cancer, cardiovascular disease, autoimmune disorders and xenograft rejection.

Because the nanoparticle as described herein has an exterior which is identical to an HDL particle, the nanoparticle will not trigger an immune response which may result in premature degradation or clearance of the nanoparticle by the immune system prior to reaching its intended target, e.g. the myeloid compartment.

The present invention is based on the realization that an apolipoprotein-based nanoparticle or an apolipoprotein mimetic-based nanoparticle may successfully be modified to accommodate nucleic acids. This may be achieved by a combination of the following features:

- the use of a cationic or ionizable cationic lipid to neutralize the nucleic acid to allow it to be loaded in the hydrophobic core of the nanoparticle;
- defining the structural components of the nanoparticle and/or the ranges of their relative amounts, e.g. the amount of apolipoprotein and/or an apolipoprotein mimetic, sterol, phospholipid, cationic or ionizable cationic lipid and, optionally, filler material (for example triglycerides).

The nanoparticles of the present invention are distinct from any nanoparticle described in the art.

In particular embodiments, the nanoparticles of this invention are low in toxicity or are non-toxic.

In particular embodiments, the core of the nanoparticle of present invention is not surrounded by a lipid bi-layer, such as present in vesicle-like or liposomal particles with lipid bi-layers surrounding an aqueous core.

In particular embodiments, the nanoparticles of this invention do not comprise synthetic (non-natural) hydrophilic polymers or (lipid) conjugates of such polymers, such as most notably polyethylene-glycol (PEG). As a result thereof, such nanoparticles do not elicit unwanted immune responses, especially upon repeated administration.

In particular embodiments, the payload (i.e. nucleic acid) of the nanoparticles of this invention is not bound by ionic interactions at the outside (surface) of the particle. Binding of nucleic acid to the outside surface of the particle is undesired as the nucleic is left exposed to the immediate surroundings, presumably making the particles more toxic as well as leading to fast (bio)-degradation of the nucleic acid payload.

In particular embodiments, the nanoparticles of present invention are substantially or entirely biodegradable. In particular embodiments, the nanoparticles of present invention are formed by building blocks that are natural or bio-compatible. For example, the nanoparticles of present invention essentially consist of or consist of C, H, N, O, S and P atoms, with additional counter cations and/or anions. In particular embodiments, the nanoparticles of present invention do not comprise inorganics and/or metals (e.g. solid Au or Ag). Inorganics and/or metals are not or less bio-degradable and are largely incompatible for in vivo use. In further particular embodiments, the core of the nanoparticles of present invention does not comprise inorganics and/or metals (e.g. solid Au or Ag).

The core of the nanoparticle may be solid and not have or bear a significant aqueous void or reservoir in the core. In particular embodiments, the core of the nanoparticle is non-aqueous.

Present inventors have further developed a method for successfully incorporating a nucleic acid in an apolipoprotein and/or apolipoprotein mimetic-based nanoparticle, as the individual components cannot simply be mixed to obtain nanoparticles as described herein.

It was found to be essential that a two-step reaction is performed, where in the first step, a nucleic acid containing nanoparticle is formed, and in the next second step, apolipoprotein and/or apolipoprotein mimetic is included in the nanoparticle. Preferably, the first step is performed at low pH and the second step is performed at physiological pH. This finding allows for the first time to include nucleic acids in an apolipoprotein and/or apolipoprotein mimetic-based nanoparticle, thus allowing delivery of said nucleic acids to the myeloid compartment.

When used herein, a nanoparticle refers to a small particle, e.g. in the range of about 10 nm to about 200 nm in diameter which may be used to deliver a payload to a target, e.g. an organ or cell in a subject.

When used herein, a subject may be a human or a non-human animal such as a mammal, preferably a human.

Filler Material

Nanoparticles as described herein may further comprise a filler material (also referred to herein as "filler" or "filler molecule") such as but not limited to lipids such as triglycerides. Therefore, in an embodiment the nanoparticle further comprises a filler selected from a triacylglyceride (also simply named a tri-glyceride) and a cholesterol acyl ester (also named cholesteryl ester) or combinations thereof, preferably wherein the triacylglyceride is tricaprylin and/or wherein the cholesterol acyl ester is cholesteryl caprylate and/or cholesteryl oleate. Cholesteryl acetate may also be employed as filler material. Yet other filler materials that can be applied are di-glycerides or tri-glycerides or other esters derived from C1-C18 carboxylic acids, preferably C6-C18 fatty acids, where these carboxylic acids and fatty acids may be saturated or unsaturated. Preferably, the filler is a triglyceride derived from C6-C18 fatty acids are preferred.

The nanoparticles as described herein may form nanodiscs or nanospheres, i.e. different shapes of particles. The shape of the nanoparticle may depend on the absence or presence of a filler material. A filler may for example be a triglyceride which is included in the core of the particle together with the payload (the nucleic acid) and the cationic or ionizable cationic lipids. It is understood that including more filler will presumably render the nanoparticles larger, up to a certain extent, where the particle become instable. Without being bound to theory, inclusion of a filler material may contribute to stabilize the nanoparticles or it may stabilize the inclusion of the payload, or it may modulate or enhance the delivery of the nucleic acid.

Nucleic Acid

Many different types of RNA, DNA or synthetic oligonucleotides have been used as nucleic acid therapeutic. The present invention is not limited to a specific type of nucleic acid as the invention is envisioned to work with any type that can be loaded using cationic or ionizable cationic lipids in the nanoparticles. Therefore, in an embodiment, the nucleic acid is RNA, or DNA or a nucleic acid analogue.

In preferred embodiments, the RNA is microRNA (miRNA), small interfering RNA (siRNA), piwi-interacting RNA (piRNA), small nuclear RNA (snoRNA), transfer RNA (tRNA), tRNA-derived small RNA (tsRNA), small regulatory RNA (srRNA), messenger RNA (mRNA), modified mRNA, ribosomal RNA (rRNA), long non-coding RNA (lncRNA) or guide RNA (gRNA) or combinations thereof and/or modifications thereof.

In particular embodiments, the antisense oligonucleotide is single strand DNA or RNA.

In preferred embodiments, the DNA is single stranded or double stranded DNA.

In preferred embodiments, the antisense oligonucleotide is single strand DNA or RNA consisting of nucleotide or nucleoside analogues containing modifications of the phosphodiester backbone or the 2' ribose, preferably wherein the nucleotide or nucleoside analogues are selected from locked nucleic acid (LNA), bridged nucleic acid (BNA), morpholino or peptide nucleic acid (PNA).

In an embodiment of the invention the nucleic acid is conjugated, and the nucleic acid conjugate is incorporated into the nanoparticle of the invention. Nucleic acid conjugates include lipid conjugates with for example phospholipids or with sterols such as cholesterol or with hydrophobic alkyl chains. Nucleic acid conjugates also include conjugates with oligomers or polymers. Preferably, these oligomers or polymers are of a hydrophobic nature.

In an embodiment of the invention, the nucleic acid is incorporated as such or 'as is' within the nanoparticle of the invention, meaning that the nucleic acid is not being conjugated. Presumably, nanoparticles of this embodiment behave in a preferred bio-compatible fashion.

Apolipoprotein

The term "apolipoprotein" when used herein refers to a protein that together with lipids forms lipoproteins, i.e. assemblies of lipids and proteins. The term encompasses wild-type apolipoproteins (such as in particular human wild-type apolipoproteins), as well as biologically active fragments thereof, biologically active variants of apolipoproteins or biologically active fragments thereof, including biologically active mutant (such as naturally occurring mutant or non-naturally occurring mutant) apolipoproteins or biologically active fragments thereof. Apolipoproteins typically function to transport lipids and fat-soluble substances in the blood. Apolipoproteins are described and include but are not limited to ApoA1, ApoA1-Milano, ApoA2, ApoA4, ApoA5, ApoB48, ApoB100, ApoC-I, ApoC-II, ApoC-III, ApoC-IV, ApoD, ApoE, ApoF, ApoH, ApoL and ApoM.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein.

The term "variant" of a protein, polypeptide, peptide or nucleic acid generally refers to proteins, polypeptides or peptides the amino acid sequence of which, or nucleic acids the nucleotide sequence of which, is substantially identical (i.e., largely but not wholly identical) to the sequence of the protein, polypeptide, peptide, or nucleic acid, e.g., at least about 80% identical or at least about 85% identical, e.g., preferably at least about 90% identical, e.g., at least 91% identical, 92% identical, more preferably at least about 93% identical, e.g., at least 94% identical, even more preferably at least about 95% identical, e.g., at least 96% identical, yet more preferably at least about 97% identical, e.g., at least 98% identical, and most preferably at least 99% identical to the sequence of the recited protein, polypeptide, peptide, or nucleic acid. Preferably, a variant may display such degrees of identity to a recited protein, polypeptide, peptide or nucleic acid when the whole sequence of the recited protein, polypeptide, peptide or nucleic acid is queried in the sequence alignment (i.e., overall sequence identity). Sequence identity may be determined using suitable algorithms for performing sequence alignments and determination of sequence identity as know per se. Exemplary but non-limiting algorithms include those based on the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62 (Henikoff et al., 1992, Proc. Natl. Acad. Sci., 89:10915-10919), cost to open a gap=11, cost to extend a gap=1, expectation value=10.0, word size=3).

An example procedure to determine the percent identity between a particular amino acid sequence and the amino acid sequence of a query polypeptide will entail aligning the two amino acid sequences using the Blast 2 sequences (Bl2seq) algorithm, available as a web application or as a standalone executable programme (BLAST version 2.2.31+) at the NCBI web site (www.ncbi.nlm.nih.gov), using suitable algorithm parameters.

A variant of a protein, polypeptide, or peptide may comprise one or more amino acid additions, deletions, or substitutions relative to (i.e., compared with) the corresponding protein or polypeptide.

The term "biologically active" is interchangeable with terms such as "functionally active" or "functional", denoting that the fragment and/or variant at least partly retains the biological activity or intended functionality of the respective or corresponding peptide, polypeptide or protein. Reference to the "activity" of a peptide, polypeptide or protein may generally encompass any one or more aspects of the biological activity of the peptide, polypeptide or protein, such as without limitation any one or more aspects of its biochemical activity, enzymatic activity, signaling activity, interaction activity, ligand activity, and/or structural activity, e.g., within a cell, tissue, organ or an organism.

Preferably, a functionally active fragment or variant, such as a mutant, may retain at least about 20%, e.g., at least about 25%, or at least 30%, or at least about 40%, or at least about 50%, e.g., at least 60%, more preferably at least about 70%, e.g., at least 80%, yet more preferably at least about 85%, still more preferably at least about 90%, and most preferably at least about 95% or even about 100% of the intended biological activity or functionality compared with the corresponding peptide, polypeptide or protein. In certain embodiments, a functionally active fragment or variant may even display higher biological activity or functionality compared with the corresponding peptide, polypeptide or protein, for example may display at least about 100%, or at least about 150%, or at least about 200%, or at least about 300%, or at least about 400%, or at least about 500% of the intended biological activity or functionality compared with the corresponding peptide, polypeptide or protein. By means of an example, where the activity of a given peptide, polypeptide or protein can be readily measured in an assay with a quantitative output, for example an enzymatic assay or a signaling assay or a binding assay producing a quantifiable signal, a functionally active fragment or variant of the peptide, polypeptide or protein may produce a signal which is at least about 20%, or at least about 25%, or at least 30%, or at least about 40%, or at least about 50%, or at least 60%, more preferably at least about 70%, or at least 80%, or at least about 85%, or at least about 90%, or at least about 95%, or at least about 100%, or at least about 150%, or at least about 200%, or at least about 300%, or at least about 400%, or at least about 500% of the signal produced by the corresponding peptide, polypeptide or protein.

By means of an example and not limitation, a biologically active fragment or variant of an apolipoprotein will at least partly retain one or more aspects of the biological activity of the corresponding native or wild-type apolipoprotein. For example, reference to the biological activity of the apolipoprotein may particularly denote the ability to interact with the components of the surface layer of the nanoparticle (e.g. phospholipid and sterol), the ability to stabilize the nanoparticles as taught herein and/or the ability to target the myeloid compartment, such as to target a myeloid cell.

When used herein, the term apolipoprotein may further refer to apolipoprotein mimetics. Apolipoprotein mimetics are short peptides, such as up to 50 amino acids, like 18-mers or 36-mers, that mimic the properties of an apolipoprotein. An example of an ApoA1 mimetic peptide is usually referred to as "18A", which is a peptide with an amino sequence: DWLKAFYDKVAEKLKEAF (SEQ ID NO: 1), with an unfunctionalized N-terminus and C-terminus. Another reported, more convenient, and also more active mimetic is ApoA1 mimetic peptide "2F", which is Ac-DWLKAFYDKVAEKLKEAF-NH2 (SEQ ID NO: 2), i.e. ApoA1 mimetic peptide 18A with an acetamide capped N-terminus and an amide C-terminus. In Leman, L. J. et al., J. Med. Chem. 2014, 57, 2169-2196 (10.1021/jm4005847) further examples of ApoA1 peptidomimetics are described, particularly in Table 2 and Table 3. Other ApoA1 peptidomimetics, such as dimer, trimer and tetramer peptides are illustrated in Zhou et al., J. Am. Chem. Soc. 2013, 135, 13414-13424 (dx.doi.org/10.1021/ja404714a). Preferred ApoA1 peptidomimetics are 18A, 2F and 4F, and any multimers of these peptides. More preferred are 2F and any dimers or trimers of this peptide.

Apolipoproteins are proteins that bind lipids to form lipoproteins. They transport lipids and fat-soluble vitamins in blood, cerebrospinal fluid and lymph. The lipid components of lipoproteins are insoluble in water. However, because of their amphipathic properties, apolipoproteins and other amphipathic molecules such as phospholipids can surround the lipids, creating a lipoprotein particle that is itself water-soluble, and can thus be carried through water-based circulation (i.e., blood, extracellular fluids, lymph). In addition to stabilizing lipoprotein structure and solubilizing the lipid component, apolipoproteins interact with lipoprotein receptors and lipid transport proteins, thereby participating in lipoprotein uptake and clearance. They also serve as enzyme cofactors for specific enzymes involved in the metabolism of lipoproteins.

Apolipoprotein A1 is a protein that in humans is encoded by the APOA1 gene. In particular embodiments, apolipoprotein A1 is human apolipoprotein A1. By means of further guidance, human apolipoprotein A1 precursor is annotated under UniProt accession number P02647.1 (www.uniprot.org). As the major component of HDL particles, it has a specific role in lipid metabolism. The protein, as a component of HDL particles, enables efflux of fat molecules by accepting fats from within cells (including macrophages within the walls of arteries which have become overloaded with ingested fats from oxidized LDL particles) for transport (in the water outside cells) elsewhere, including back to LDL particles or to the liver for excretion.

It is envisioned that any apolipoprotein may be used in the nanoparticles. Therefore, in an embodiment the apolipoprotein is selected from ApoA1, ApoA1-Milano, ApoA2, ApoA4, ApoA5, ApoB48, ApoB100, ApoC-I, ApoC-II, ApoC-III, ApoC-IV, ApoD, ApoE, ApoF, ApoH, ApoL and ApoM, preferably selected from ApoA1, ApoA2, ApoA4, ApoA5, ApoB100, ApoC-I, ApoC-II, ApoC-III, ApoC-IV and ApoE, more preferably selected from ApoA1, ApoA4, ApoA5, ApoB100, ApoC-Ill and ApoE, even more preferably selected from ApoA1, ApoB100 and ApoE. In a particularly preferred embodiment the apolipoprotein is ApoA1 because it allows very efficient targeting of the nanoparticle to the myeloid compartment. In an alternative preferred embodiment the apolipoprotein is ApoE because it allows targeting of the nanoparticle to dendritic cells.

In particular embodiments, the apolipoprotein is a wild-type apolipoprotein or a fragment thereof, preferably a full length wild-type apolipoprotein.

In particular embodiments, the apolipoprotein is a variant of an apolipoprotein or a fragment thereof or a mutant of an apolipoprotein or a fragment thereof.

Apolipoproteins can be produced and purified by methods that are known in the art, such as recombinant protein expression from *E-coli* bacteria, or from other organisms, followed by steps required to isolate the apolipoprotein, e.g. ApoA1, in (sufficiently) pure form. Apolipoproteins can also be isolated from blood, by applying a sequence of purification methods that are known in the art, such as described in Chapman M J, Goldstein S, Lagrange D, Laplaud P M. A density gradient ultracentrifugal procedure for the isolation of the major lipoprotein classes from human serum. J Lipid Res. 1981 February; 22(2):339-58. PMID: 6787159. Apolipoprotein peptide mimetics can be synthesized as according to peptide synthesis protocols and conjugation methods that are known in the art.

It was found by the inventors that there are several advantages associated with the use of apolipoprotein and/or apolipoprotein mimetic in nanoparticles to deliver a nucleic acid at a target site. First of all, apolipoprotein and/or apolipoprotein mimetic stabilizes the nanoparticles by preventing aggregate on during preparation and storage. For the nanoparticles to stay in a stable emulsion it is essential that the nanoparticles do not aggregate or fuse, which may result in precipitation of the particles. The apolipoprotein and/or apolipoprotein mimetic helps to stabilize the particles and prevents aggregation. Further, apolipoprotein and/or apolipoprotein mimetic ensures in vivo stability of the nanoparticles. Because apolipoprotein and/or apolipoprotein mimetic is naturally present on lipid particles circulating in the blood stream, such as LDL and HDL, they are not recognized by the immune system as non-self, thereby ensuring natural stealth, as opposed to chemical modifications or other non-natural methods to improve stability. Lastly, the use of apolipoprotein and/or apolipoprotein mimetic facilitates desirable interactions with immune cells, for example in the myeloid compartment to deliver the nucleic acid cargo.

Therefore, in an embodiment the apolipoprotein and/or apolipoprotein mimetic in the nanoparticle is used to:

prevent aggregation upon preparation and storage;
improve in vivo stability;
provide natural stealth; and/or
facilitate interactions with immune cells.

Cationic Lipid and Ionizable Cationic Lipid

When used herein, the term ionizable cationic lipid refers to a lipid which has a neutral charge at physiological pH (e.g. at pH 7 to 7.5, preferably at pH 7.3 to 7.5, such as at ~pH 7.4) and which is protonated or positively charged at a lower pH (e.g. at pH 1 to 5, preferably at pH 1 to 4, such as at pH 4). It is understood that ionizable cationic lipids are particularly useful, as they may be protonated at low pH thus facilitating binding to the hydrophilic nucleic acid. By subsequently raising the pH the lipids may become (partly) neutral further facilitating inclusion in a hydrophobic environment, e.g. the hydrophobic core of a nanoparticle. Alternatively, and without being bound to theory, the ionizable lipids may remain positively charged within the nanoparticles, even though the pH of the surrounding aqueous solution has been raised to physiological pH, such as about 7.4, due to the action of the surface layer of the nanoparticle that comprises phospholipid sterol and apolipoprotein and/or an apolipoprotein mimetic, and/or due to the non-aqueous environment within the nanoparticle. Furthermore, ionizable cationic lipids are theorized to facilitate the endosomal escape of the nucleic acid in the target cells, where due to the low pH the ionizable cationic lipid will be protonated.

Non-limiting examples of ionizable cationic lipids are DLin-DMA (2-[2,2-bis(octadeca-9,12-dienyl)-1,3-dioxolan-4-yl]-N,N-dimethylethanamine), DLin-KC2-DMA (2-[2,2-bis[(9Z,12Z)-octadeca-9,12-dienyl]-1,3-dioxolan-4-yl]-N,N-dimethylethanamine) and DLin-MC3-DMA ([(6Z,9Z,28Z,31Z)-heptatriaconta-6,9,28,31-tetraen-19-yl] 4-(dimethylamino)butanoate) as represented by formula 1 below:

Formula 1

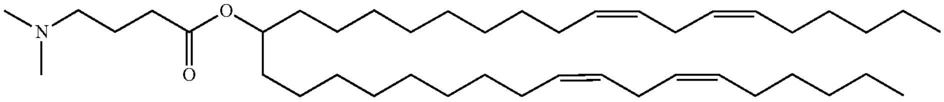

Indeed, a broad range of ionizable cationic lipids (including lipidoids) can be employed for preparing the nanoparticles of this invention, as various series of ionizable cationic lipids have been developed and reported on in literature. Further non-limiting examples include molecules cKK-E12, C12-200, L319, Acuitas-A9, Moderna-L5, TT3 and ssPalmE (such as described in, for example, Witzigmann et al., Advanced Drug Delivery Reviews 159 (2020) 344-363; doi.org/10.1016/j.addr.2020.06.026).

The ionizable lipid may further be an ionizable triglyceride. A non-limiting example is the compound represented by formula 2:

Formula 2

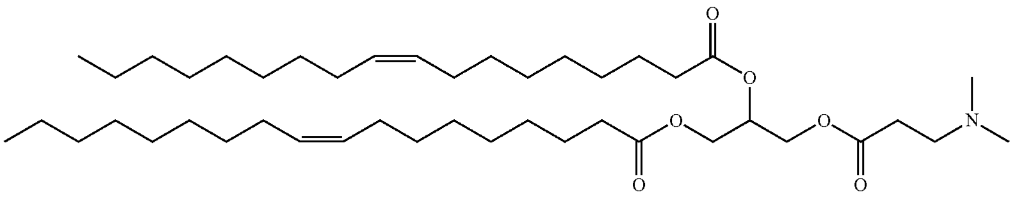

The ionizable lipid may further be a cholesterol ester (also named a cholesteryl ester). A non-limiting example is represented by formula 3:

Formula 3

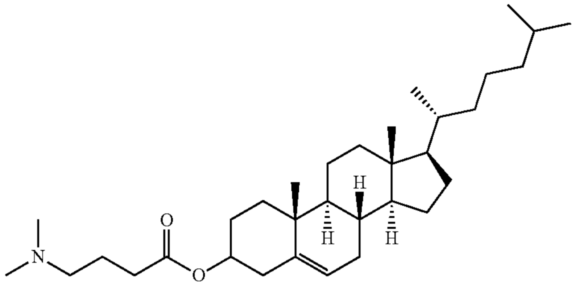

When used herein, the term cationic lipid refers to a positively charged lipid at physiological pH (e.g. pH 7.4). Non-limiting examples of cationic lipids are DOTMA (1,2-di-O-octadecenyl-3-trimethylammonium propane), DOGS (2,5-bis(3-aminopropylamino)-N-[2-[di(heptadecyl) amino]-2-oxoethyl]pentanamide), DOSPA (2-[3-[4-(3-aminopropylamino)butylamino]propylcarbamoylamino]ethyl-[2,3-bis[[(Z)-octadec-9-enoyl]oxy]propyl]-dimethylazanium) and DOTAP (1,2-dioleoyl-3-trimethylammonium-propane). Other examples include any ionizable cationic lipid molecules wherein the tertiary amine moiety has been converted to a quaternary ammonium moiety, for example by alkylation, such as by methylation (-Me), ethylation (-Et), benzylation (-Bn) or ethoxylation ($—CH_2CH_2—OH$). The resultant quaternary ammonium molecule has a permanent positive (cationic) charge, and accordingly also bears a counter anion, for example a chloride anion.

In an embodiment, only ionizable cationic lipids are used to prepare the nanoparticles of the invention. Accordingly, in an embodiment, the nanoparticles as taught herein do not comprise cationic lipids.

In an embodiment, only cationic lipids are used to prepare the nanoparticles of the invention. Accordingly, in an embodiment, the nanoparticles as taught herein do not comprise ionizable cationic lipids.

In an embodiment, a combination of ionizable cationic lipids and cationic lipids are used to prepare the nanoparticles of the invention.

When used herein the term "payload" in general refers to a substance to be included in a particle and delivered at a target site. When referring to the nanoparticles of the invention, the term "payload" refers to the nucleic acid, preferably in combination with the cationic and/or ionizable cationic lipids.

The term "lipid" is well known in the art, and as used herein may in particular be considered to encompass both lipids, i.e. naturally occurring hydrophobic biomolecules such as for example fatty acids, mono-, di- or tri-glycerides of fatty acids, sterol (derivatives) or phospholipids, and lipid-like biomolecules. It is noted that the cationic lipids or ionizable cationic lipids (or lipidoids) described herein are typically not lipids within the most narrow interpretation of the term, i.e. naturally occurring hydrophobic biomolecules such as for example fatty acids, mono-, di- or tri-glycerides of fatty acids, sterol (derivatives) or phospholipids, but are lipid-like biomolecules that resemble lipid biomolecules, i.e. they preferably contain groups that are biocompatible (such as e.g. esters or amides), and/or are constructed using naturally occurring building blocks (e.g. fatty acids, glycerol, cholesterol).

In an embodiment, the cationic or ionizable cationic lipid is selected from an ionizable cationic ester of a long chain alcohol, an ionizable cationic ester of a diglyceride or an ionizable cationic ester of a sterol, or combinations thereof.

The ionizable cationic ester of a long chain alcohol may for example be an ester of a tertiary amine with a carboxy group such as a compound with the formula $(CH_3)_2N(CH_2)_n$COOH, wherein n is an integer of 1 or more, for instance n is 1 to 12; for example 3-dimethylamino-propionic acid or 4-dimethylamino-butyric acid or 5 dimethylamino-pentanoic acid. The ester is formed with a long chain alcohol. The long chain alcohol is preferably a primary or secondary alcohol with a straight or branched chain length of 8 or more carbon atoms, for example 8, 9, 10, 11, 12, 13, 14, 15, 16, 17, 18, 19, 20 or more.

The ionizable cationic ester of a diglyceride is preferably a diacyl glycerol (i.e. a di-glyceride) coupled at the 1 or 2 position with a tertiary amine with a carboxy group such as a compound with the formula $(CH_3)_2N(CH_2)_n$COOH, wherein n is an integer of 1 or more, for instance n is 1 to 12; for example 3-dimethylamino-propionic acid or 4-dimethylamino-butyric acid or 5-dimethylamino-pentanoic acid. The diacyl glycerol may comprise medium chain or long chain saturated or unsaturated fatty acids or derivatives or modifications thereof.

The ionizable cationic ester of a sterol is preferably an ester of sterol coupled at the hydroxyl group to a tertiary amine with a carboxy group such as a compound with the formula $(CH_3)_2N(CH_2)_n$COOH, wherein n is an integer of 1 or more, for instance n is 1 to 12; for example 3-dimethylamino-propionic acid or 4-dimethylamino-butyric acid or 5 dimethylamino-pentanoic acid. The sterol may be cholesterol, stigmasterol or β-sitosterol.

In the above, a carboxy compound is presented with the formula $(CH_3)_2N(CH_2)_n$COOH, wherein n is an integer of 1 or more. Instead of this compound, an alternative compound can be employed with the formula $NH_2$—(C═NH)—NH—$(CH_2)_n$COOH, wherein n is an integer of 1 or more, for instance n is 1 to 12. This carboxy compound comprises a guanidine group instead of a tertiary amine group.

For preparing the nanoparticles of this invention, the ionizable cationic lipid can for example be selected from the molecules as according to Formulas (I) to (V).

(I)

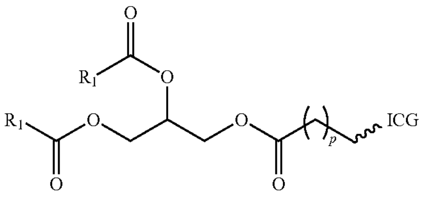

(II)

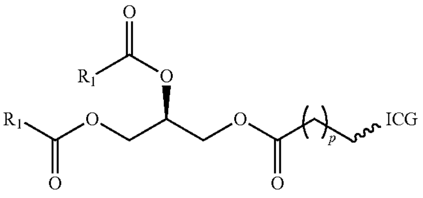

-continued (III)

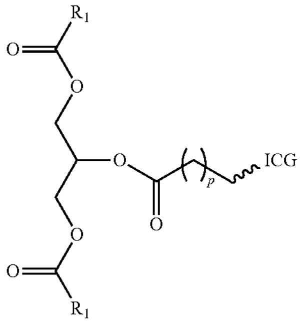

(IV)

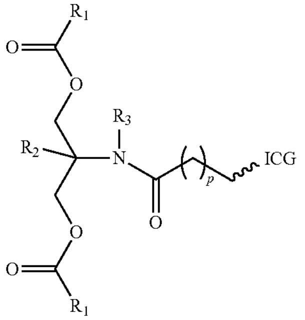

(V)

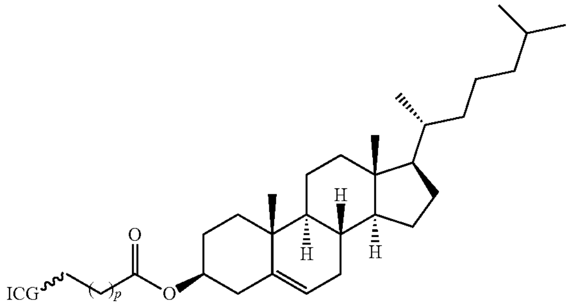

ICG = Ionizable Cationic Group

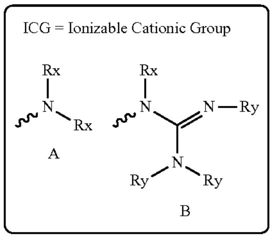

Formula (I) represents a tri-glyceride, wherein the ionizable cationic group (ICG) is comprised in the 1-position.

Formula (II) represents the same type of tri-glyceride as represented in Formula (i), albeit that the molecule is stereo-specifically defined in the naturally occurring configuration, i.e. as it would in a phospholipid: the ICG group is in the same position as the phosphate group is in a phospholipid.

Formula (III) represents a tri-glyceride, wherein the ionizable cationic group (ICG) is comprised in the 2-position.

Formula (IV) represents a di-ester (or a tri-ester), wherein the ionizable cationic group (ICG) is connected via the amide functionality.

Formula (V) represents a cholesteryl ester, wherein the ionizable cationic group (ICG) is connected via the ester functionality.

The ionizable cationic group (ICG) is connected via the wavy bond to the rest of the molecule for any of the Formulas (I) to (V), where the ICG can either represent a tertiary amine (ICG type A, or ICG-A) or it can represent a guanidine (ICG type B, or ICG-B).

In Formulas (I) to (IV), $R_1$ can be independently selected for every position, and it represents a linear or branched C1-C19 alkyl, a linear or branched C1-C19 alkenyl, aryl, arylene-alkyl or alkylene-aryl group, wherein said alkyl or alkenyl group, optionally containing 5 heteroatoms, independently selected from 0 and N. Preferably, every $R_1$-group within a specific molecule as according to any of the Formulas (I) to (IV) is the same $R_1$ group. Preferably, the $R_1$ group is a linear or branched C5-C19 alkyl group, or a linear or branched C5-C19 alkenyl group. When R, is an alkenyl group, this group preferably has one single double bond only. More preferably, the $R_1$ group is a linear or branched C9-C17 alkyl group or a linear or branched C5-C17 alkenyl group. Preferably R1 is a linear C5-C15 alkyl group or a linear C17-C19 alkenyl. Carboxylic acids derived from $R_1$, i.e. $R_1$—COOH, are preferably naturally occurring fatty acid molecules such as capric acid, lauric acid, myristic acid, palmitic acid, stearic acid, palmiteic acid, oleic acid or linoleic acid. Preferred are the C10-C16 saturated fatty acids as well as oleic acid (C18, unsaturated).

The integer p is a discrete number and not an average value; p can be 0 to 11. Preferably, p is 0, 1, 2, 3, 4, 5, 6, 7, 8 or 9. More preferably, p is 1, 2, 3 or 4.

The $R_2$ group in Formula (IV) can be selected from a hydrogen, a methyl, an ethyl and a —$CH_2$—O—C(O)—$R_{1a}$ group (wherein $R_{1a}$ has the same meaning as $R_1$ defined above). Preferably, $R_2$ is a hydrogen, a methyl or a —$CH_2$—O—C(O)—$R_1$ group. More preferably, $R_2$ is a methyl.

The $R_3$ group in Formula (IV) can be selected from a hydrogen, aryl, arylene-alkyl, alkylene-aryl or a linear C1-C6 alkyl group. Preferably, $R_3$ is a hydrogen or a methyl. More preferably, $R_3$ is a hydrogen.

The $R_x$ group in ICG-A can be independently selected for every position, and is selected from a methyl, an ethyl, a propyl and an ethylene-hydroxy (—$CH_2$—$CH_2$—OH) group, preferably it is a methyl group. Preferably, both $R_x$ groups in ICG-A are the same groups, and they preferably are methyl groups.

The $R_y$ group in ICG-B can be independently selected for every position from a hydrogen, a linear or branched C1-C18 alkyl, aryl, arylene-alkyl or alkylene-aryl group, wherein said alkyl group optionally contains up to 5 heteroatoms, independently selected from O and N. Preferably, the $R_y$ group is selected from a hydrogen and a linear C1-C6 alkyl group. Even more preferably, the $R_y$ group is a hydrogen. Preferably, all four $R_y$-groups in ICG-B are the same groups, and they preferably are hydrogens.

From Formulas (I) to (V), Formulas (I), (II) and (IV) are preferred. More preferred are Formulas (I) and (II).

From the ICGs ICG-A and ICG-B, ICG-A is preferred, i.e. tertiary amine ionizable cationic lipids are preferred.

The ionizable cationic lipid molecule as according to any one of the Formulas (I) to (V) has a molecular weight that is higher than 250 Dalton, preferably higher than 350 Dalton, more preferably higher than 450 Dalton. It has a molecular weight that is lower than 3000 Dalton, preferably lower than 1800 Dalton, more preferably lower than 1200 Dalton.

The molecules that are represented by Formulas (I) to (V) may exist in various isomeric forms such as rotamers, tautomers, stereoisomers or regiomers, and all of these are included in the scope of the present invention.

The ionizable cationic lipid as according to any one of the Formulas (I) to (V) preferably is a single compound, i.e. not a mixture of compounds. Accordingly, the purity of the ionizable cationic lipid of Formula (I) to (V) preferably is 50% or higher, preferably 80% or higher, more preferably 90% or higher, most preferably 95% or higher. In case the ionizable cationic lipid is a mixture of compounds, then this is preferably due only to the presence of undefined stereocenters in the molecule. An example is the use of branched alkyl chains in the ionizable cationic lipid that are of racemic origin. Other examples are tri-glycerides wherein the substitution pattern over the three hydroxy-groups in the glycerol entity is not stereo-specifically defined.

The ionizable cationic lipids as according to any one of the Formulas (I) to (V) can be prepared by synthetic methods that are known in the art. In the Examples section, and more particularly Example 9, of this application various non-limiting syntheses of ionizable cationic lipids are presented.

The (ionizable) cationic lipid preferably can be processed from solutions. Accordingly, the (ionizable) cationic lipid is preferably soluble in solvents ranging in polarity. Therefore, the (ionizable) cationic lipid is preferably soluble in tricaprylin, in ethanol or in iso-propanol, more preferably in all three of these solvents. The solubility can be checked by stirring about 20 mg of the (ionizable) cationic lipid in about 1 gram of tricaprylin, ethanol or iso-propanol, and assessing whether all material spontaneously dissolves to create a clear/transparent solution with a concentration of about 2 w/w %. The test can be done at about 20° C. (room temperature) or at about 37° C. Preferably, the (ionizable) cationic lipid is soluble at room temperature.

The (ionizable) cationic lipid is preferably non-toxic, or it may have a limited and low toxicity, either on its own, or when bound to or tested together with nucleic acids, or assayed in the nanoparticle of the invention. Toxicity cell tests can be executed by methods that are known in the art, such as for example by cell viability MTT assays, or by similar or comparable tests.

A further aspect provides an ionizable cationic lipid molecule according to any one of the Formulas (I) to (V), as specified in more detail above. A further aspect provides the use of an ionizable cationic lipid molecule according to any one of the Formulas (I) to (V) in the preparation of a nanoparticle, such as a nucleic acid containing nanoparticle, such as wherein the ionizable cationic lipid molecule(s) is used to complex with the nucleic acid.

Sterol

When used herein the term sterol refers to compounds that are derived from sterol (2,3,4,5,6,7,8,9,10,11,12,13,14,15,16,17-hexadecahydro-1H-cyclopenta[a]phenanthren-3-ol) by substituting other chemical groups for some of the hydrogen atoms, or modifying the bonds in the ring. Sterols and related compounds play essential roles in the physiology of eukaryotic organisms. For example, cholesterol forms part of the cellular membrane in animals, where it affects the cell membrane's fluidity and serves as secondary messenger in developmental signalling. When used herein sterol may for example refer to a sterol selected from the group consisting of cholesterol, desmosterol, stigmasterol, β-sitosterol, ergosterol, hopanoids, hydroxysteroid, phytosterol, steroids, hydrogenated cholesterol, campesterol, zoosterol, or a combination thereof. In the nanoparticle the sterol maintains or regulates membrane fluidity (i.e. in the phospholipid surface (mono)layer barrier of the nanoparticle). In an embodiment the sterol is selected from cholesterol, stigmasterol, or β-sitosterol, or combinations thereof. In an embodiment the sterol is cholesterol, ergosterol, hopanoids, hydroxysteroid, phytosterol, steroids, zoosterol, stigmasterol, or β-sitosterol. In a preferred embodiment the sterol is or comprises cholesterol.

Phospholipid

Phospholipids, also known as phosphatides, are a class of lipids whose molecule has a hydrophilic head containing a phosphate group, and two hydrophobic tails derived from fatty acids, joined by a glycerol molecule.

If the phospholipid is a marine phospholipid, the phospholipid typically has omega-3 fatty acids EPA and DHA integrated as part of the phospholipid molecule. Simple organic molecules such as choline, ethanolamine or serine could be used to modify the phosphate group.

Phospholipids are a key component of all cell membranes. They can form lipid bilayers because of their amphiphilic characteristic. In eukaryotes, cell membranes also contain another class of lipid, a sterol (particularly cholesterol), that is interspersed among the phospholipids. The combination provides fluidity in two dimensions combined with mechanical strength against rupture.

Therefore, in an embodiment the phospholipid is selected from a phosphatidylcholine, a phosphatidylethanolamine, a phosphatidylserine and a phosphatidylglycerol, or combinations thereof.

The acyl groups in the phospholipid may, individually, be medium chain or long chain fatty acids. In an embodiment at least one, preferably both, of the acyl groups in the phospholipid are long chain fatty acids, preferably wherein said long chain fatty acids are selected from C14, C16 and C18 chains, i.e. from myristic acid, myristoleic acid, palmitic acid, palmitoleic acid, stearic acid, linoleic acid and oleic acid, or combinations thereof.

In a particularly preferred embodiment the phospholipid is a neutral phospholipid, meaning it is zwitterionic at physiological pH (it has a nett neutral charge). Therefore, in a preferred embodiment the phospholipid is a phosphatidylcholine (PC) or a phosphatidylethanolamine (PE).

Accordingly, non-limiting examples of phospholipids that can be used are dilauroylphosphatidylcholine (DLPC), dimyristoylphosphatidylcholine (DMPC), dipalmitoylphosphatidylcholine (DPPC), distearoylphosphatidylcholine (DSPC), dioleoylphosphatidylcholine (DOPC), dilauroylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dilauroyl phosphatidylethanolamine (DLPE), dimyristoyl phosphatidylethanolamine (DMPE), dipalmitoyl phosphatidylethanolamine (DPPE), distearoyl phosphatidylethanolamine (DSPE), dilauroyl phosphatidylserine (DLPS), dimyristoyl phosphatidylserine (DMPS), dipalmitoyl phosphatidylserine (DPPS), distearoyl phosphatidylserine (DSPS), 1-palmitoyl-2-oleoyl-sn-glycero-3-phosphocholine (POPC), 1,2-dioleoyl-sn-glycero-3-phosphoethanolamine (DOPE), as well as mixtures thereof.

Lyso-phospholipids are phospholipids in which one of the acyl groups has been removed by hydrolysis, leaving an alcohol group. These molecules therefore have one instead of two fatty acid chains. These phospholipids can also be applied, for example to regulate the shape, function and fluidity of the outer layers of the nanoparticle as taught herein. As lyso-phospholipids, 1-myristoyl-2-hydroxy-sn-glycerophosphocholine (MHPC), 1-palmitoyl-2-hydroxy-sn-glycero-3-phosphocholine (PHPC) and 1-stearoyl-2-hydroxy-sn-glycero-3-phosphocholine (SHPC), or mixtures thereof can be employed.

In an embodiment all phospholipids employed to prepare the nanoparticle of the invention have a natural origin, meaning that they are found in any kind of natural surrounding such as e.g. in (a) certain cell membrane(s). Accordingly, these phospholipids are bio-compatible and bio-degradable. The natural-origin phospholipids may be isolated and purified from natural sources (soya, bovine milk, rapeseed, chicken eggs, sunflower, etc.), but they may also be prepared and purified by (semi)-synthetic means.

Nanoparticle Features

Nanoparticles of embodiments of the invention comprise, consist essentially of, or consist of a nucleic acid, a cationic and/or ionizable cationic lipid, a phospholipid, a sterol, an apolipoprotein and/or apolipoprotein mimetic, and optionally a filler material, wherein:

- the amount of apolipoprotein and/or apolipoprotein mimetic ranges from 0.1 to 90 weight %; and/or
- the amount of nucleic acid ranges from 0.01 to 90 weight %; and/or
- the amount of phospholipid ranges from 0.1 to 95 weight %; and/or
- the amount of sterol ranges from 0.1 to 95 weight %; and/or
- the amount of cationic and/or ionizable cationic lipid ranges from 0.1 to 95 weight %, and
- the amount of optionally present filler material ranges from 0 to 95 weight %, wherein these weight percentages are based on the combined amounts of the apolipoprotein and/or apolipoprotein mimetic, the nucleic acid, the phospholipid, the sterol and the cationic and/or ionizable cationic lipid plus the optional filler material, i.e. these five or six components add up to 100% of the weight of the nanoparticle.

In an embodiment, the amount of apolipoprotein and/or apolipoprotein mimetic, ranges from 0.2 to 50 weight %, such as from 3 to 20 weight % or from 4 to 20 weight %, more preferably from 0.5 to 30 weight %, more preferably from 1 to 20 weight %.

In an embodiment, the amount of nucleic acid ranges from 0.02 to 30 weight %, more preferably from 0.05 to 20 weight %, more preferably from 0.1 to 15 weight %, such as from 0.5 to 5 weight %.

In an embodiment, the amount of phospholipid ranges from 0.2 to 60 weight %, more preferably from 1 to 50 weight %, such as from 10 to 50 weight %, more preferably from 3 to 40 weight %, such as from 10 to 40 weight %.

In an embodiment, the amount of sterol ranges from 0.2 to 90 weight %, more preferably from 0.5 to 70 weight %, such as from 2 to 65 weight %, more preferably from 1 to 50 weight %, such as from 2 to 45 weight %, from 10 to 45 weight % or from 10 to 20 weight %.

In an embodiment, the amount of cationic and/or ionizable cationic lipid ranges from 0.2 to 90 weight %, more preferably from 0.5 to 80 weight %, more preferably from 1 to 70 weight %, such as from 5 to 60 weight %, from 8 to 60 weight %, from 9 to 60 weight %, from 10 to 60 weight %, from 15 to 25 weight %, or from 20 to 60 weight %.

In an embodiment, the amount of optional filler or filler molecule ranges from 0 to 90 weight %, more preferably from 0 to 80 weight %, more preferably from 0 to 70 weight %, such as from 0 to 65 weight %.

In particular embodiments, the amount of optional filler or filler molecule ranges from 20 to 80 weight %, more preferably from 30 to 70 weight %, even more preferably from 30 to 65 weight %, such as from 40 to 65 weight %, from 45 to 55 weight % or from 30 to 60 weight %.

In particular embodiments, the nanoparticle as taught herein does not comprise a filler or filler molecule.

These weight percentages as indicated above are based on the combined amounts of the apolipoprotein and/or apolipoprotein mimetic, the nucleic acid, the phospholipid, the sterol and the cationic and/or ionizable cationic lipid, and optionally the filler material, i.e. these five or six components add up to 100% of the weight of the nanoparticle in the context of these statements.

It was found that nanoparticles constructed from apolipoprotein and/or apolipoprotein mimetic, phospholipids, sterol and cationic and/or ionizable cationic lipid within these ranges are stable and can successfully incorporate nucleic acids.

the outer layer of the nanoparticle is composed of phospholipids, apolipoprotein and/or apolipoprotein mimetic, and sterol. In preferred embodiments, the ratio of apolipoprotein and/or apolipoprotein mimetic to phospholipid based on weight is from 2:1 to 1:10, as this allows to assemble stable nanoparticles. Therefore, in an embodiment, the employed ratio of apolipoprotein and/or apolipoprotein mimetic to phospholipid based on weight is from 2:1 to 1:10, more preferably from 1:1 to 1:5 even more preferably from 1:1.5 to 1:4.

In an embodiment, the relative amounts of the components in the nanoparticle relate to the ratios in which they are employed to prepare the nanoparticle.

After formulation and optionally purification of the nanoparticles of the invention, the retention (or recovery or entrapment) of the various nanoparticle components can be assessed. This can be done by methods that are known in the art. For example, RNA retention can be determined using a Ribogreen assay, while apolipoprotein A1 (Apo-A1) recovery can be assessed using a colorimetric protein quantification assay. Cholesterol and phospholipid recovery can be determined using standard colorimetric quantification assays. Recoveries of the various components of the nanoparticles of present invention are high.

In an embodiment, the relative amounts of the components in the nanoparticle relate to determined levels of incorporation of components in the nanoparticles after formulation and optionally purification.

In an embodiment, nucleic acid (e.g. siRNA or mRNA) retention in the nanoparticle is preferably 1% or higher, preferably 5% or higher, more preferably 20% or higher, such as 40% or higher, even more preferably 50% or higher, such as 60% or higher, 70% or higher, or 80% or higher.

In an embodiment, sterol (e.g. cholesterol) recovery in the nanoparticle is 1% or higher, preferably 10% or higher, more preferably 30% or higher, such as 40% or higher, even more preferably 50% or higher, such as 60% or higher, 70% or higher, 80% or higher, or 85% or higher.

In an embodiment, phospholipid recovery in the nanoparticle is 1% or higher, preferably 10% or higher, more preferably 30% or higher, such as 40% or higher even more preferably 50% or higher, such as 60% or higher, 70% or higher, or 80% or higher.

In an embodiment, apolipoprotein (e.g. Apo-A1) and/or apolipoprotein mimetic recovery in the nanoparticle is 1% or higher, preferably 5% or higher, more preferably 10% or higher, even more preferably 20% or higher, such as 30% or higher or 35% or higher.

In an embodiment, the amount of apolipoprotein and/or apolipoprotein mimetic ranges from 0.05 to 2.0 mol %, such as from 0.10 to 2.0 mol % or from 0.08 to 0.5 mol %; and/or the amount of phospholipid ranges from 5 to 90 mol %, such as from 15 to 90 mol % or from 8.0 to 50 mol %; and/or the amount of sterol ranges from 2.5 to 65 mol %, such as from 2.5 to 50 mol % or from 4 to 65 mol %; and/or the amount of cationic or ionizable cationic lipid ranges from 5.0 to 80 mol %, such as from 8.0 to 80 mol % or from 5 to 65 mol % wherein the molar percentage is based solely on the combined amounts of the apolipoprotein and/or apolipoprotein mimetic, phospholipids, sterols and cationic and/or ionizable cationic lipids in the nanoparticle. It was found that nanoparticles constructed from apolipoprotein and/or apolipoprotein mimetic, phospholipids, sterol and cationic and/or ionizable cationic lipid within these ranges are stable and can successfully incorporate nucleic acids.

The outer layer of the nanoparticle is composed of phospholipids, apolipoprotein and/or apolipoprotein mimetic and sterol. In order to assemble stable nanoparticles preferably the ratio of apolipoprotein to phospholipid based on percentage molar weight is between 1:25 and 1:400. Therefore, in an embodiment, the ratio of apolipoprotein and/or apolipoprotein mimetic to phospholipid based on percentage molar weight is between 1:25 and 1:400, more preferably between 1:50 and 1:200 even more preferably between 1:75 and 1:150.

It was found that the nanoparticles according to the invention have a relatively defined and constant size. In other words, the nanoparticles according to the invention are homogenous in size. The average size is presumably largely determined by the core components, namely the amount and type of nucleic acid, amount cationic and/or ionizable cationic lipid and amount of filler. It is understood that the filler is optional, and that the particle size can presumably be increased by including increasing amounts of filler. In an embodiment the nanoparticles according to invention have an average size of from about 10 to about 200 nm, from about 20 to about 200 nm, or from about 30 to about 200 nm, preferably from about 30 to about 100 nm, preferably wherein the average size refers to particle diameter.

In particular embodiments, the size is the z-average size or the numbered average size.

The sizes of the nanoparticles of the invention can be assessed by methods that are known in the art. For example, dynamic light scattering (DLS) can be employed to measure the diameters of the nanoparticles. Cryo-TEM measurements can also be employed for this purpose. Both techniques may also be used to assess the distribution (or dispersity) in diameters of prepared nanoparticle formulations.

In particular embodiments, the particle size dispersity within a group of nanoparticles as taught herein is between 0 and 0.5, preferably between 0 and 0.4, more preferably between 0 and 0.3 and most preferably between 0 and 0.2.

The shape and nature of the nanoparticles of the invention can be assessed by for example cryo-TEM measurements. The particles may be spherical or near-spherical in shape. The particles may also be oval-like or even worm-like in shape. The particles may also be disc-like. Preferably, the particles are spherical, near-spherical and/or somewhat oval in shape. Preferably, the particles are not disc-like in shape. Preferably, the particles appear solid in nature, i.e. no significant nor large inner aqueous compartments can be observed within the particles. The cryo-TEM observed particles do not have to be completely homogeneous, i.e. the electron densities may vary within the particle. Preferably, the particles of the invention have similar sizes and shapes, i.e. there is no large distribution in sizes nor in shapes. The nanoparticles as defined herein comprise a hydrophobic core and a hydrophilic surface, and therefore may be dissolved in water or aqueous solution such as a saline solution or buffer.

The inherent properties resulting from the constituents of the nanoparticles as defined by the invention result in the nanoparticles being stable in suspension for months, such as for at least 1 week, at least 2 weeks, at least 3 weeks, at least 1 month, at least 2 months, at least 4 months, at least 6 months, at least 8 months, at least 10 months, or at least 12 months. Suitable aqueous buffers are known in the field, such as Phosphate Buffered Saline (PBS), Tris Buffered Saline (TBS). Suitable saline solutions are known, and non-limiting examples include aqueous solutions of NaCl or KCl. When the nanoparticle is intended to be administered to a subject, the nanoparticles should be suspended in a physiologically acceptable carrier for the purpose. For example, if the nanoparticle is intended for intravenous delivery, the physiologically acceptable carrier is typically a fluid isotonic with blood. For example a solution of sodium chloride at 0.9% w/v concentration, a 5% w/v dextrose solution, Ringer's solution, Ringer's lactate or Ringer's acetate may be used, but other suitable carriers are known.

Therefore, in an aspect the invention relates to a composition comprising the nanoparticle according to the invention and a physiologically acceptable carrier. In an embodiment the composition is a pharmaceutical composition. It is understood that the composition may further comprise additional components, such as but not limited to pharmaceutical drugs or biopharmaceutical. This may an attractive option for a combination therapy of a nucleic acid (comprised in the nanoparticle) and a drug. A drug may be a small compound, an antibody or antigen binding fragment, a further nanoparticle, but is not limited thereto.

Uses

The purpose of the nanoparticles described herein is to deliver a nucleic acid to a cell or to deliver a nucleic acid therapy to a subject. The nucleic acid may be for example an mRNA encoding a peptide or protein of interest which is to be expressed in the cell, or may comprise a short nucleic acid such as an siRNA, shRNA intended to interfere in gene expression (e.g. gene silencing), or it may comprise a component of the CRISPR-Cas or a related system (e.g. gRNA) to induce a mutation in the genome of the cell. Therefore in general the mode of action of the nucleic acid (the payload of the nanoparticle) is in the cytoplasm or the nucleus. Therefore the nanoparticle preferably has at least the following properties: 1) it allows targeting of the intended target cell, and 2) it allows delivery of the payload where it can assert its action (thus in most cases in the cytoplasm or nucleus of the target cell).

A further aspect of the invention relates to the nanoparticle according to the invention, or the composition according to the invention for use as a medicament.

It is understood that the nucleic acid therapy comprising nanoparticles may be administered to a subject in need thereof. Depending on the target cells or tissue, the administration may be parenteral, e.g. intravenous, intramuscular or subcutaneous. The administration may further be oral, sublingual, topical, rectal, nasal (inhaled) or vaginal. Further the targeting of the target tissue or cells is determined by the proper choice of apolipoprotein and/or apolipoprotein mimetic. In an embodiment, the use of the nanoparticle or composition according to the invention, comprises delivering a nucleic acid to the myeloid compartment or the spleen. This may for example be achieved by intravenous parenteral administration. Preferably, the apolipoprotein and/or apolipoprotein mimetic is a myeloid compartment targeting apolipoprotein such as ApoA1.

Present inventors have found that the nanoparticles as taught herein enable efficient nucleic acid therapeutics delivery to the myeloid cell compartment in lymphoid organs, such as but not limited to the bone marrow and the spleen, for effective immunotherapy. Indeed, present inventors have found that nanoparticles of the invention, after systemic injection, can target tissues (spleen, bone marrow) that are associated with the presence of immune cells.

A further aspect provides the nanoparticle as taught herein, or the composition as taught herein for use in immunotherapy.

In an aspect the invention relates to the nanoparticle according to the invention, or the composition according to the invention for use in the treatment of a disease by stimulating or inhibiting an innate immune response, preferably wherein said disease is a disease that would benefit from stimulating or inhibiting the innate immune response in a subject, such as a disease characterized by a defective innate immune response, more preferably wherein said disease to be treated is a cancer, a cardiovascular disease, an autoimmune disorder or xenograft rejection. Therefore the nanoparticles according to the invention may be used in the treatment of any disease relating the immune system such as any immune disorder, or for the treatment of any disease or disorder where modulating the immune response is deemed a viable treatment option.

In a further aspect the invention relates to a method for the in vivo delivery of a nucleic acid, the method comprising administering the nanoparticle according to the invention or the composition according to the invention to a subject.

In a further aspect, the invention relates to a method for treating a disease or disorder in a subject in need thereof by stimulating or inhibiting an innate immune response, the method comprising administering a therapeutically effective amount of the nanoparticle according to the invention or the composition according to the invention to the subject. In particular embodiments, the disease or disorder is a disease or disorder characterized by a defective innate immune response. In an embodiment, the disease or disorder is selected from cancer, cardiovascular disease, autoimmune disorder or xenograft rejection.

By targeting the myeloid compartment, a nucleic acid therapy can successfully be delivered to progenitor cells of the different blood cell types, as opposed to already differentiated cells present in blood and tissue, such as T cells and macrophages. In doing so, the innate immune response may be modulated, e.g. stimulated or inhibited, by the nucleic acid therapy, depending on the desired result. For example, in autoimmune disorders, cardiovascular disease or xenograft rejection (prevention of), inhibition of the autoimmune response is desirable, while in cancer, stimulation of the immune response to target cancer cells is desirable.

Nanoparticle Formulation—the Preparation of aNPs

The present invention provides apolipoprotein and/or apolipoprotein mimetic-based nanoparticles with nucleic acids (herein, these particles of the invention are sometimes referred to as aNPs). Until now it was not possible to include nucleic acids in such nanoparticles as the core of such particles is hydrophobic and thus not suitable for incorporation of nucleic acids due to their hydrophilic nature. Although the use of ionizable cationic lipids together with nucleic acids has been described as a tool for intracellular delivery of the nucleic acid, simply combining ionizable cationic lipids and nucleic acids with the other lipid components does not result in the formation of the lipid nanoparticles as described herein. For example, mixing a nucleic acid (e.g. siRNA or mRNA) with a liposomal formulation will create particles in which the nucleic acid is exposed to its aqueous surroundings, making the nucleic acid prone to fast degradation. Furthermore, these particles are instable and display formation of large ill-defined aggregates. In another example, simple addition of an apolipoprotein and/or apolipoprotein mimetic to a liposomal formulation will not result in nanoparticle formulations with defined and desired characteristics.

Surprisingly, and without using a PEG, a PEG-conjugate or another synthetic polymer-type stabilizer material, present inventors have found a controlled formulation process that generates stable and/or non-toxic aNPs with clearly defined sizes and shapes, with an encapsulated and shielded nucleic acid payload, with proper recoveries for the employed components, and with a nucleic acid payload that is active when exposed to (various) cell lines. Moreover, a broad range of compositions (e.g. with varying types and/or levels of apolipoprotein and/or apolipoprotein mimetic, phospholipid, sterol, cationic and/or ionizable cationic lipid, nucleic acid and optional filler) could be employed to generate these aNPs.

Accordingly, the present invention also revolves around the realization that the nucleic acid can be incorporated in the nanoparticles by using a two-step formulation process.

Therefore, in an aspect the invention relates to a method for producing a nanoparticle, comprising the step of:

a) mixing, preferably rapid mixing, of lipid components in organic solvent with a nucleic acid in an aqueous buffer to produce lipid nanoparticles, wherein the lipid components comprise a phospholipid, a sterol, a cationic lipid or ionizable cationic lipid, and optionally a filler material (e.g. a triglyceride), wherein the aqueous buffer has a pH of 5.0 or lower; and b) mixing, preferably rapid mixing, of the lipid nanoparticles (as prepared under a)) with an apolipoprotein and/or apolipoprotein mimetic to produce the nanoparticle of the invention at a pH between 6.0 and 8.0.

The organic solvent may be an alcohol such as ethanol, iso-propanol, methanol, acetonitrile, dimethyl sulfoxide (DMSO), chloroform or combinations thereof. Preferred organic solvents are water mixable and non-toxic, for example ethanol and DMSO, or combinations thereof.

For example, the organic solvent may be from 96% to 100% of ethanol, preferably 100% ethanol.

Rapid mixing is known in the field and has for example been described in Hirota et al. BIOTECHNIQUES VOL. 27, NO. 2, p 286-289; Jeffs et al., Pharm Res 22, 362-372 (2005); Kulkarni et al., ACS Nano 2018, 12, 5, 4787-4795

The aqueous buffer in step a) has a low pH to ensure that the ionizable cationic lipid is positively charged, allowing binding within and inclusion of the nucleic acid/cationic lipid complex in the particle. For example, the buffer may have a pH of 5.0 or lower, such as 4.9, 4.8, 4.7, 4.6, 4.5, 4.4, 4.3, 4.2, 4.1, 4.0, 3.9, 3.8, 3.7, 3.6, 3.5 or lower. The aqueous buffer may be any buffer that does not damage the nucleic acid. An exemplary buffer is sodium acetate at pH 4.0. The nanoparticle is then taken in an aqueous buffer with a pH of around 6 to 8, preferably 7 to 8 more preferably around 7.4. This may for example be achieved by dialysis with an aqueous buffer in the indicated pH range. A non-limiting example of an aqueous buffer suitable for this step is 155 mM PBS at pH 7.4, but it is understood that any buffer may be used that does not damage the nucleic acid.

In step b) the nanoparticle in an aqueous buffer at pH between 6 to 8, preferably between pH 7 to 8, is rapidly mixed with apolipoprotein and/or apolipoprotein mimetic in an aqueous buffer at pH between 6 to 8, preferably between pH 7 to 8, to obtain the nanoparticles according to the invention.

The above described two-step formulation process as taught herein results in aNPs with a broad set of desired and beneficial characteristics (stability, low toxicity or non-toxicity, high nucleic acid retention, nucleic acid activity, etc.). However, the described formulation method is non-limiting as other processes may also lead to aNPs with beneficial features.

A further aspect the invention relates to a nanoparticle obtainable or obtained by a method comprising the step of:

a) mixing, preferably rapid mixing, of lipid components in organic solvent with a nucleic acid in an aqueous buffer to produce lipid nanoparticles, wherein the lipid components comprise a phospholipid, a sterol, a cationic lipid or ionizable cationic lipid, and optionally a filler material (e.g. a tryglyceride), wherein the aqueous buffer has a pH of 5.0 or lower; and b) mixing, preferably rapid mixing, of the lipid nanoparticles (as prepared under a)) with an apolipoprotein and/or apolipoprotein mimetic to produce the nanoparticle of the invention at a pH between 6.0 and 8.0.

Further Aspects to the Invention

It is understood that nanoparticles according to the invention are able to deliver the nucleic acid in a target cell or tissue. The target cell or tissue may be in a subject, or may be in vitro or ex vivo. Therefore, in an aspect the invention relates to an in vivo, in vitro or ex vivo method for introducing a nucleic acid in a cell, the method comprising contacting the nanoparticle according to the invention or the composition according to the invention with a cell. In particular embodiments, the cell is a cell of the myeloid compartment or myeloid cell.

The present application also provides aspects and embodiments as set forth in the following Statements:

Statement 1. A nanoparticle comprising:

an apolipoprotein;

a phospholipid;

a sterol;

a cationic or ionizable cationic lipid; and a nucleic acid.

Statement 2. The nanoparticle according to statement 1 wherein the nanoparticle further comprises a filler selected from a triacylglyceride and a cholesterol acyl ester or combinations thereof, preferably wherein the triacylglyceride is tricaprylin and/or wherein the cholesterol acyl ester is cholesterol caprylate and/or cholesterol oleate.

Statement 3. The nanoparticle according to any one of the preceding statements, wherein the nucleic acid is RNA, DNA or a nucleic acid analogue, preferably wherein the RNA is microRNA (miRNA), small interfering RNA (siRNA), piwi-interacting RNA (piRNA), small nuclear RNA (snoRNA), transfer RNA (tRNA), tRNA-derived small RNA (tsRNA), small regulatory RNA (srRNA), messenger RNA (mRNA), modified mRNA, ribosomal RNA (rRNA), long non-coding RNA (lncRNA) or guide RNA (gRNA) or combinations thereof and/or modifications thereof; or preferably wherein the DNA is single stranded or double stranded DNA; or preferably wherein the antisense oligonucleotide is single strand DNA or RNA consisting of nucleotide or nucleoside analogues containing modifications of the phosphodiester backbone or the 2' ribose, more preferably wherein the nucleotide or nucleoside analogues are selected from locked nucleic acid (LNA), bridged nucleic acid (BNA), morpholino or peptide nucleic acid (PNA).

Statement 4. The nanoparticle according to any one of the preceding statements, wherein the apolipoprotein is selected form ApoA1, ApoA2, ApoA4, ApoA5, ApoB48, ApoB100, ApoC-I, ApoC-II, ApoC-III, ApoC-IV, ApoD, ApoE, ApoF, ApoH, ApoL and ApoM, preferably selected from ApoA1, ApoA2, ApoA4, ApoA5, ApoB100, ApoC-I, ApoC-II, ApoC-III, ApoC-IV and ApoE, more preferably selected from ApoA1, ApoA4, ApoA5, ApoB100, ApoC-Ill and ApoE, most preferably selected from ApoA1, ApoB100 and ApoE.

Statement 5. The nanoparticle according to any one of statements 1 to 5, wherein the apolipoprotein in the nanoparticle is used to:

prevent aggregation upon preparation and storage;
improve in vivo stability;
provide natural stealth; and/or
facilitate interactions with immune cells.

Statement 6. The nanoparticle according to any one of the preceding statements, wherein the cationic or ionizable cationic lipid is selected from an ionizable cationic ester of a long chain alcohol, an ionizable cationic ester of a diglyceride or an ionizable cationic ester of a sterol or combinations thereof.

Statement 7. The nanoparticle according to any one of the preceding statements, wherein the sterol is selected from cholesterol, stigmasterol, or β-sitosterol, or combinations thereof.

Statement 8. The nanoparticle according to any one of the preceding statements, wherein: the phospholipid is selected from a phosphatidylcholine, a phosphatidylethanolamine, a phosphatidylserine and a phosphatidylglycerol or combinations thereof, preferably wherein at least one, more preferably both, of the acyl groups in the phospholipid are long chain fatty acids, even more preferably wherein said long chain fatty acids are selected from myristoleic acid, palmitoleic acid and oleic acid or combinations thereof.

Statement 9. The nanoparticle according to any one of the preceding statements, wherein: the amount of apolipoprotein ranges from 0.10 to 2.0 mol %; and/or the amount of phospholipid ranges from 15 to 90 mol %; and/or the amount of sterol ranges from 2.5 to 50 mol %; and/or the amount of cationic or ionizable cationic lipid ranges from 8.0 to 80 mol %, wherein the molar percentage is based solely on the combined amounts of the apolipoprotein, phospholipids, sterols and cationic or ionizable cationic lipids in the nanoparticle.

Statement 10. The nanoparticle according to any one of the preceding statements, wherein the ratio of apolipoprotein to phospholipid based on percentage molar weight is between 1:25 and 1:400, more preferably between 1:50 and 1:200 even more preferably between 1:75 and 1:150.

Statement 11. The nanoparticle according to any one of the preceding statements having an average size of 30 to 100 nm.

Statement 12. A composition comprising the nanoparticle according to any one of statement 1 to 11 and a physiologically acceptable carrier, preferably wherein the composition is a pharmaceutical composition.

Statement 13. The nanoparticle according to any one of statements 1 to 11, or the composition according to statement 12 for use as a medicament.

Statement 14. The nanoparticle or composition for use according to statement 13, the use comprising delivering a nucleic acid to the myeloid compartment or the spleen.

Statement 15. The nanoparticle according to any one of statements 1 to 11, or the composition according to statement 12 for use in the treatment of a disease by stimulating or inhibiting an innate immune response, preferably wherein said disease is a cancer, a cardiovascular disease, an autoimmune disorder or xenograft rejection.

Statement 16. Method for producing a nanoparticle, comprising the step of:

a) mixing, preferably rapid mixing, of lipid components in organic solvent with a nucleic acid in an aqueous buffer to produce lipid nanoparticles, wherein the lipid components comprise a phospholipid, a sterol, a triglyceride (optional) and a cationic lipid or ionizable cationic lipid and a nucleic acid, wherein the aqueous buffer has a pH of 5.0 or lower; and
b) mixing, preferably rapid mixing, of lipid nanoparticles with an apolipoprotein to produce the nanoparticle at a pH between 6.0 and 8.0.

Statement 17. An in vivo, in vitro or ex vivo method for introducing a nucleic acid in a cell, the method comprising contacting the nanoparticle according to any one of statements 1 to 11 or the composition according to statement 12 with a cell.

Statement 18. A method for the in vivo delivery of a nucleic acid, the method comprising administering the nanoparticle according to any one of statements 1 to 11 or the composition according to statement 12 to a subject.

Statement 19. A method for treating a disease or disorder in a subject in need thereof by stimulating or inhibiting an innate immune response, the method comprising administering a therapeutically effective amount of the nanoparticle according to statements 1 to 11 or the composition according to statement 12 to the subject.

Statement 20. The method according to statement 19, wherein the disease is selected from cancer, cardiovascular disease, autoimmune disorder or xenograft rejection.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1. General Description of Formulation and Characterization

Nanoparticle formulations self-assemble based on ionic and hydrophobic interactions. The components are prepared at the desired concentrations in their respective organic solvent (lipids and other structural components) or aqueous buffer (nucleic acid payloads). The solutions are then brought together via rapid mixing techniques encompassing microfluidic or T-junction mixing.

An excess of aqueous buffer is essential for the formation process. When used herein, an excess of aqueous buffer refers to a ratio of (aqueous buffer):(organic solvent) (based on volume) of at least 2:1 or higher, e.g. 2.2:1, 2.5:1, 2.8:1 or 3:1 or higher.

After initial mixing the small fraction of organic solvent is removed, for example with dialysis or centrifugal filtration. These steps yield lipid nanoparticles to which, in the next step, apolipoprotein and/or apolipoprotein mimetic is added via a rapid mixing technique (such as for example a drip method). After apolipoprotein and/or apolipoprotein mimetic addition and processing, residual protein needs to be removed by dialysis or centrifugal filtration. Finally, the sample is concentrated to a desired concentration (see FIG. 2).

Accordingly, the nucleic acid nanoparticle aNP comprises:

(a) a nucleic acid;
(b) an (ionizable) cationic molecule;
(c) an apolipoprotein;
(d) a phospholipid;
(d) a sterol; and
(e) optionally a triglyceride or a derivative thereof.

After formulating the aNP, the physicochemical properties of the nanoparticle formulations are determined. These properties can vary depending on the formulation's specific composition. Nanoparticles' size and dispersity are determined via dynamic light scattering (DLS) and electron microscopy (e.g. cryo TEM). Electron microscopy is also used to evaluate the nanoparticle morphology. Additionally, the recovery of input material components such as nucleic acid, apolipoprotein and/or apolipoprotein mimetic, phospholipid and cholesterol is determined with various commercially available assays known in the art. Shelf-life is assessed by determining the formulations' physicochemical characteristics over an extended period (1 month) while stored in buffer at 4° C. For a large number of nucleic acid nanoparticle formulations (~150), physicochemical properties and shelf-life have been characterized. With specific formulations, reproducibility and stability under physiological conditions has been investigated.

The following molar percentage ranges of components were tested and generated aNPs were found to be stable, where the molar percentage is based on total amount of apolipoprotein (Apo-A1), phospholipid, sterol (cholesterol) and cationic or ionizable cationic lipid only, so excluding filler, nucleic acid and optional other components:

the amount of apolipoprotein Apo-A1 ranges from 0.08 to 2.0 mol %, such as from 0.10 to 2.0 mol %; and/or
the amount of phospholipid ranges from 5 to 90 mol %, such as from 15 to 90 mol %; and/or
the amount of sterol ranges from 2.5 to 65 mol %, such as from 2.5 to 50 mol %; and/or
the amount of cationic or ionizable cationic lipid ranges from 5.0 to 80 mol %, such as from 8.0 to 80 mol %.

Outside these ranges the nanoparticles may be unstable. Furthermore, a filler material such as a triglyceride may be added in the range from 0 to 95 mol % where the molar percentage is based on total amount of apolipoprotein, phospholipid, sterol and cationic or ionizable cationic lipid only.

Figure 2:
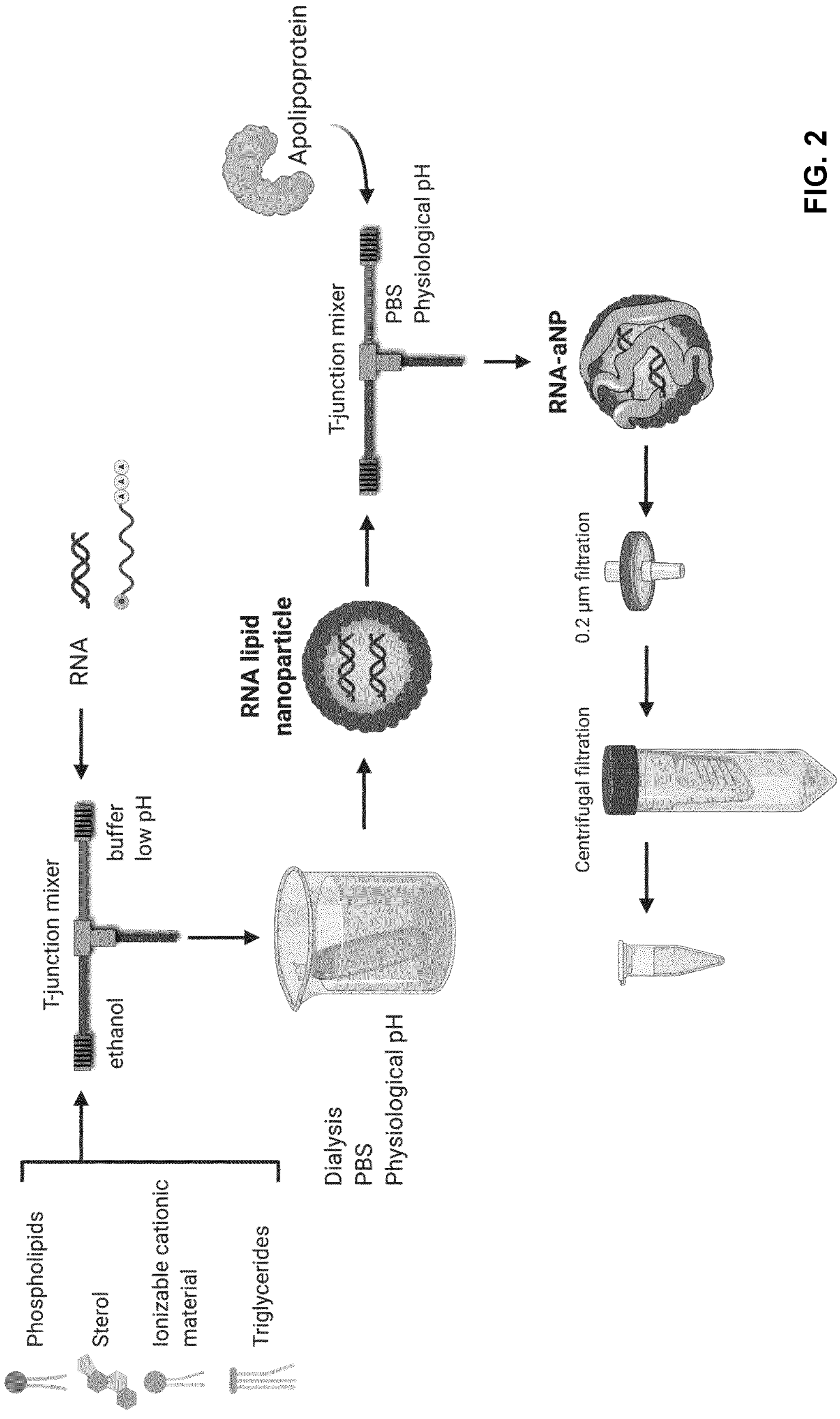
FIG. 2: Schematic overview of an illustrative method according to certain embodiments of the invention for producing apolipoprotein lipid nanoparticles (aNP) containing nucleic acids such as RNA as described herein.

Example 2. An Illustrative Method for Producing Apolipoprotein Lipid Nanoparticles (aNP) Containing Nucleic Acids Such as RNA as Described Herein (FIG. 2)

In the first step, a phospholipid, a sterol such as cholesterol, an ionizable cationic lipid, and an optional filler material (e.g. a triglyceride) were dissolved in a water-miscible organic solvent such as 96%-100% ethanol (e.g. 2.33 mL) and the solution was rapidly mixed (at specified flow rates and ratios) with an aqueous solution that was kept at a lower pH and that contained a nucleic acid (e.g. 25 mM sodium acetate 7 mL, pH 4). For mixing, a T-junction mixing device was used, such as at 28 mL/min. Other microfluidics-based mixing methods, such as mixing in chips with staggered herringbone structures, may also be employed. The resulting lipid nanoparticles were dialyzed at physiological pH (e.g. dialysis at 4° C., overnight, 2×, 155 mM PBS, pH 7.4) and were next, in a second step, rapidly mixed at physiological pH with apolipoproteins such as apolipoprotein A1 to obtain the nanoparticles (aNPs) according to the invention. Apolipoprotein A1 may be present in 155 mM PBS, pH 4. Alternatively, peptide mimetics of apolipoproteins may be used in the second mixing step. For mixing, a T-junction mixing device can be used, such as at 13.3 mL/min. After mixing, the obtained nucleic acid nanobiologic may be incubated for one hour. Optionally, the nanoparticles may be filtered and concentrated (e.g. 0.2 μm filtration followed by a 100 kDa centrifugal filtration). The aNPs of this invention may also be processed by other methods.

Figure 3:
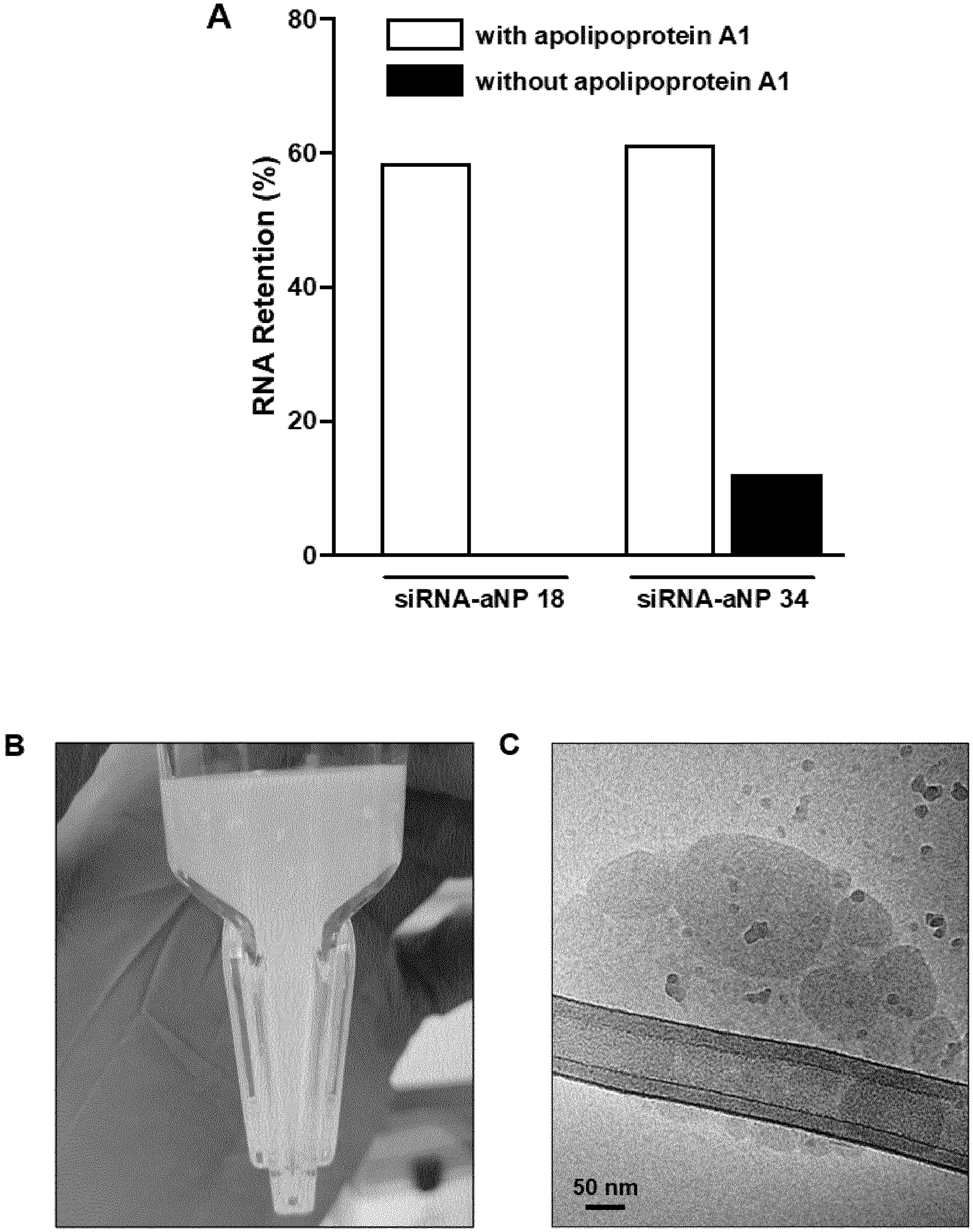
FIG. 3: siRNA retention in apolipoprotein nanoparticles (aNPs) according to certain embodiments of the invention and instability of comparative example nanoparticles (NPs) without apolipoprotein. (A) Representative aNP containing siRNA (siRNA-aNP) 18 and 34 were prepared according to the production procedure depicted in FIG. 2 (white bars). Additionally, comparative NPs were prepared by omitting the procedure's second step, whereby apolipoprotein A1 is incorporated in the formulation (black bars). RNA retention was determined using the Ribogreen assay one day post formulating. (B) Representative image of the comparative example siRNA-NP formulation 18 that has no apolipoprotein A1 incorporated. (C) Representative cryogenic transmission electron micrographs of the comparative example siRNA-NP formulation 18 (scale bar 50 nm).

Example 3. siRNA Retention in Apolipoprotein Nanoparticles (aNPs) and Instability of Comparative Example Nanoparticles (NPs) without Apolipoprotein (FIG. 3)

Two representative aNP containing siRNA (siRNA-aNP) (aNP 18 and 34, of which the formulation is shown in Table 1 (FIG. 11)) were prepared according to the production procedure according to Example 2 (FIG. 2). siRNA-aNP formulations 18 and 34 are formulations according to certain embodiments of the invention and comprise varying amounts of phospholipid (namely 1-palmitoyl-2-oleoyl-sn-glycero-3-phosphocholine (POPC) or 1,2-dimyristoyl-sn-glycero-3-phosphocholine (DMPC)), cholesterol, an ionizable cationic lipid (namely Dlin-MC3-DMA), triglycerides, apolipoprotein A1 (ApoA1) and siRNA.

Additionally, comparative NPs were prepared by omitting the procedure's second step whereby apolipoprotein A1 is incorporated in the formulation. RNA retention was determined using the Ribogreen assay (ThermoFisher—R11490) one day post formulating the NPs.

Only the aNPs as according to the invention convincingly captured the siRNA payload (FIG. 3A). The comparative example NPs without apolipoprotein did not or only hardly retained the siRNA (FIG. 3A).

FIG. 3B shows a representative image of the comparative example siRNA-NP formulation 18 that had no apolipoprotein A1 incorporated, showing large ill-defined precipitates/aggregates in the hazy solution, indicating the inability of forming a stable (transparent) formulation.

FIG. 3C shows a representative cryogenic transmission electron micrographs of the comparative example siRNA-NP formulation 18 showing a large ill-defined aggregate (scale bar 50 nm).

In conclusion, these data show that apolipoprotein is a crucial and essential structural component for the formation and stability of apolipoprotein lipid nanoparticles (aNP) containing nucleic acids.

ApoA1 Purification

A small culture of ClearColi cells transformed with pET20b-apoA1 plasmid was started in LB medium with 100 μg/mL ampicillin. The next day, 20 mL of small culture was diluted in 1 liter of 2YT medium to start large cultures. The culture was grown at 37° C. and 150 rpm until an OD600 of 0.6-0.8, then Isopropyl β-D-1-thiogalactopyranoside (IPTG) was added at a final concentration of 0.1 mM to induce expression. The induced culture was incubated overnight at 20° C. and 150 rpm. Induced bacterial cultures were pelleted and cells were lysed chemically by resuspending pellets in 5 mL BugBuster Protein Extraction Reagent (Novagen) per gram pellet. Benzonase Nuclease (Merck Millipore) was added to cells resuspended in BugBuster, and then the cell suspension was incubated at room temperature while shaking. The cell lysate was kept on ice at all times. After lysis, cell lysate was centrifuged to pellet insoluble cell debris and supernatant was flown through an IMAC column containing immobilized nickel ions. The column was washed with 8 column volumes of buffer A (20 mM Tris, 500 mM NaCl, 10 mM imidazole, pH 7.9), then 8 column volumes of buffer A50 (20 mM Tris, 500 mM NaCl, 50 mM imidazole, pH 7.9). To elute apoA1, 8 column volumes of buffer A500 (20 mM Tris, 500 mM NaCl, 500 mM imidazole, pH 7.9) was applied to the column. All fractions of the purification steps were collected and analyzed with SDS-PAGE. The buffer of fractions containing purified apoA1 was changed to PBS using Amicon Ultracentrifugal Filters (Amicon). To store apoA1, aliquots were snap-frozen in liquid nitrogen and stored at −70° C.

Figure 4:
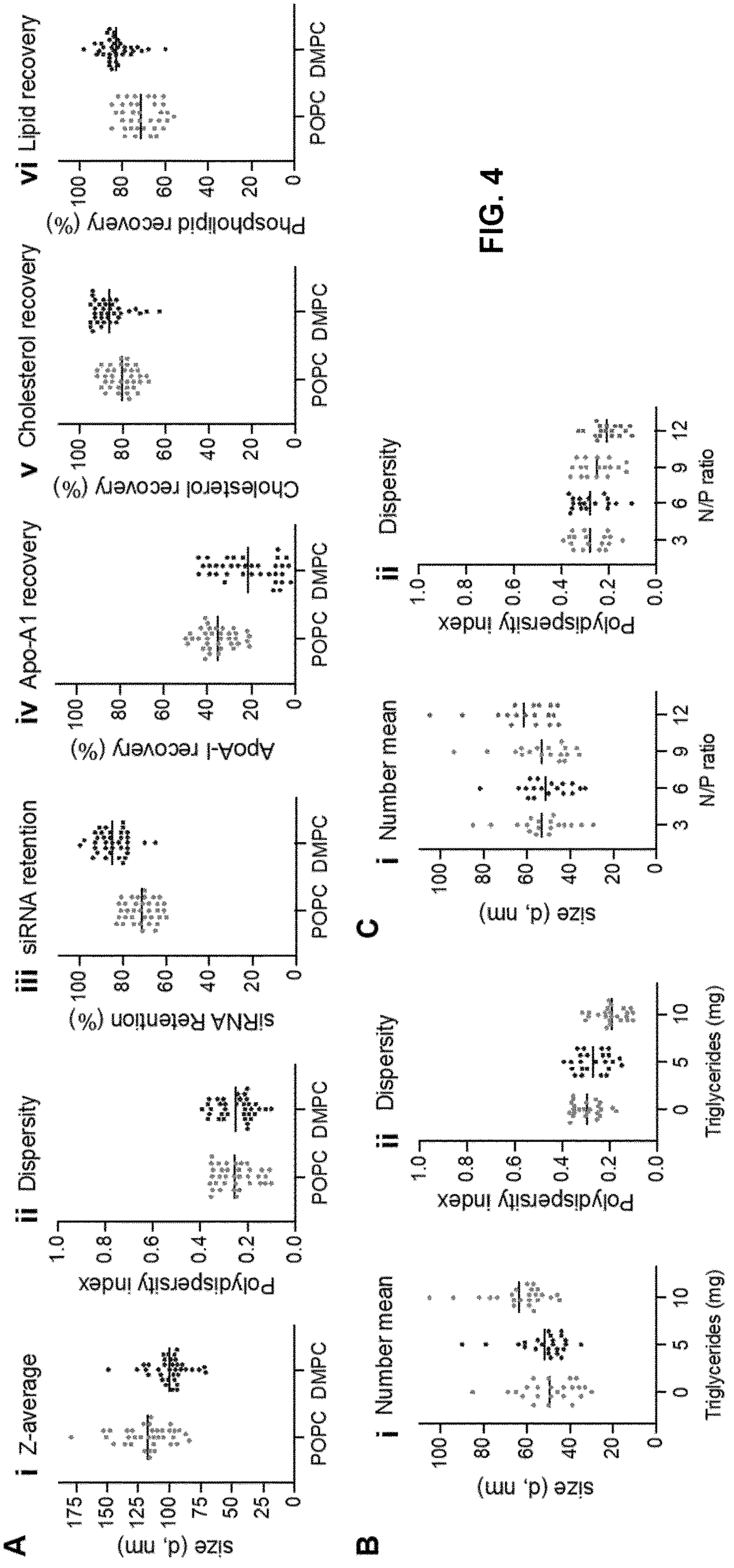
FIG. 4: The lipid composition of apolipoprotein lipid nanoparticles (aNP) containing siRNA (siRNA-aNP) according to certain embodiments of the invention influences their physicochemical properties and can be optimized to obtain siRNA-aNP with optimal characteristics. (A) One day after formulating, the library's individual siRNA-aNP formulations' physicochemical properties were determined according to (i) particle size (z-average) and (ii) particle size dispersity as assessed using dynamic light scattering (DLS), (iii) for siRNA retention using Ribogreen assay, (iv) apolipoprotein A1 (apo-A1) using colorimetric protein quantification assay, and (v) cholesterol and (vi) phospholipid recovery using standard colorimetric quantification assays. Data are displayed for both formulation types in which either 1-palmitoyl-2-oleoyl-sn-glycero-3-phosphocholine (POPC) or 1,2-dimyristoyl-sn-glycero-3-phosphocholine (DMPC) was employed. (B) Analysis of the library's individual siRNA-aNP formulations according to (i) particle size (number mean) and (ii) particle size dispersity using dynamic light scattering (DLS) one day after production, displayed by the formulations' triglyceride content. (C) Analysis of the library's individual siRNA-aNP formulations according to (i) particle size (number mean) and (ii) particle size dispersity using dynamic light scattering (DLS) one day after production, displayed by the formulations' N/P ratios. The N/P ratio is the employed ratio of positively-chargeable amine (N=nitrogen) groups of ionizable cationic materials to negatively-charged nucleic acid phosphate (P) groups).

Example 4. The Lipid Composition of Apolipoprotein Lipid Nanoparticles (aNP) Containing siRNA (siRNA-aNP) Influences their Physicochemical Properties and can be Optimized to Obtain siRNA-aNP with Optimal Characteristics (FIG. 4)

A library of 72 siRNA-aNP formulations was established and physicochemical parameters were analyzed. siRNA-aNP formulations contained from 8 to 52 mol % of phospholipid (namely 1-palmitoyl-2-oleoyl-sn-glycero-3-phosphocholine (POPC) or 1,2-dimyristoyl-sn-glycero-3-phosphocholine (DMPC)), from 4 to 62 mol % cholesterol, from 5 to 62 mol % of an ionizable cationic lipid (namely Dlin-MC3-DMA), from 0 to 76 mol % triglycerides, from 0.08 to 0.5 mol % apolipoprotein A1 (prepared as described in Example 3) and from 0.03 to 0.18% of non-specific (Integrated DNA technologies—51-01-14-03) or firefly luciferase (Integrated DNA technologies—custom sequence) siRNA. The exact formulations of formulations 1, 3, 6, 7, 8, 9, 10, 11, 12, 14, 18, 19, 20, 21, 22, 23, 24, 29, 31, 32, 33, 34, 35, 39, 42, 43, 44, 45, 46, 47, 48, 50, 54, 55, 56, 59, 60, 67, 68, 71 and 72 are shown in Table 1 (FIG. 11).

siRNA-aNP formulations were produced using the procedure as described in Example 2.

One day after formulating, the library's individual siRNA-aNP formulations' physicochemical properties were determined according to (i) particle size (z-average) and (ii) particle size dispersity as assessed using dynamic light scattering (DLS), (iii) for siRNA retention using Ribogreen assay, (iv) apolipoprotein A1 (apo-A1) using colorimetric protein quantification assay, and (v) cholesterol and (vi) phospholipid recovery using standard colorimetric quantification assays (FIG. 4A). Data are displayed in FIG. 4A for both formulation types in which either 1-palmitoyl-2-oleoyl-sn-glycero-3-phosphocholine (POPC) or 1,2-dimyristoyl-sn-glycero-3-phosphocholine (DMPC) was employed as a phospholipid. The results in FIG. 4A show that the aNPs were optimized by varying the composition to yield stable and homogeneous formulations of around 100 nm that effectively encapsulate siRNA. The results in FIG. 4A also show that apolipoprotein A1, cholesterol, and phospholipids were effectively incorporated in the formulations.

The library's individual siRNA-aNP formulations were further analyzed according to (i) particle size (number mean) and (ii) particle size dispersity using dynamic light scattering (DLS) one day after production, displayed by the formulations' triglyceride content. The results in FIG. 4B show that adding tri-glycerides as a filler molecule resulted in increased siRNA-aNP size and homogeneity.

The library's individual siRNA-aNP formulations were also analyzed according to (i) particle size (number mean) and (ii) particle size dispersity using dynamic light scattering (DLS) one day after production, displayed by the formulations' N/P ratios. The N/P ratio is the employed ratio of positively-chargeable amine (N=nitrogen) groups of ionizable cationic materials to negatively-charged nucleic acid phosphate (P) groups in the nucleic acid component(s) as described elsewhere in the present specification. The results in FIG. 4 C indicate that siRNA-aNPs were produced with various N/P ratios without influencing particle size or dispersity.

Figure 5:
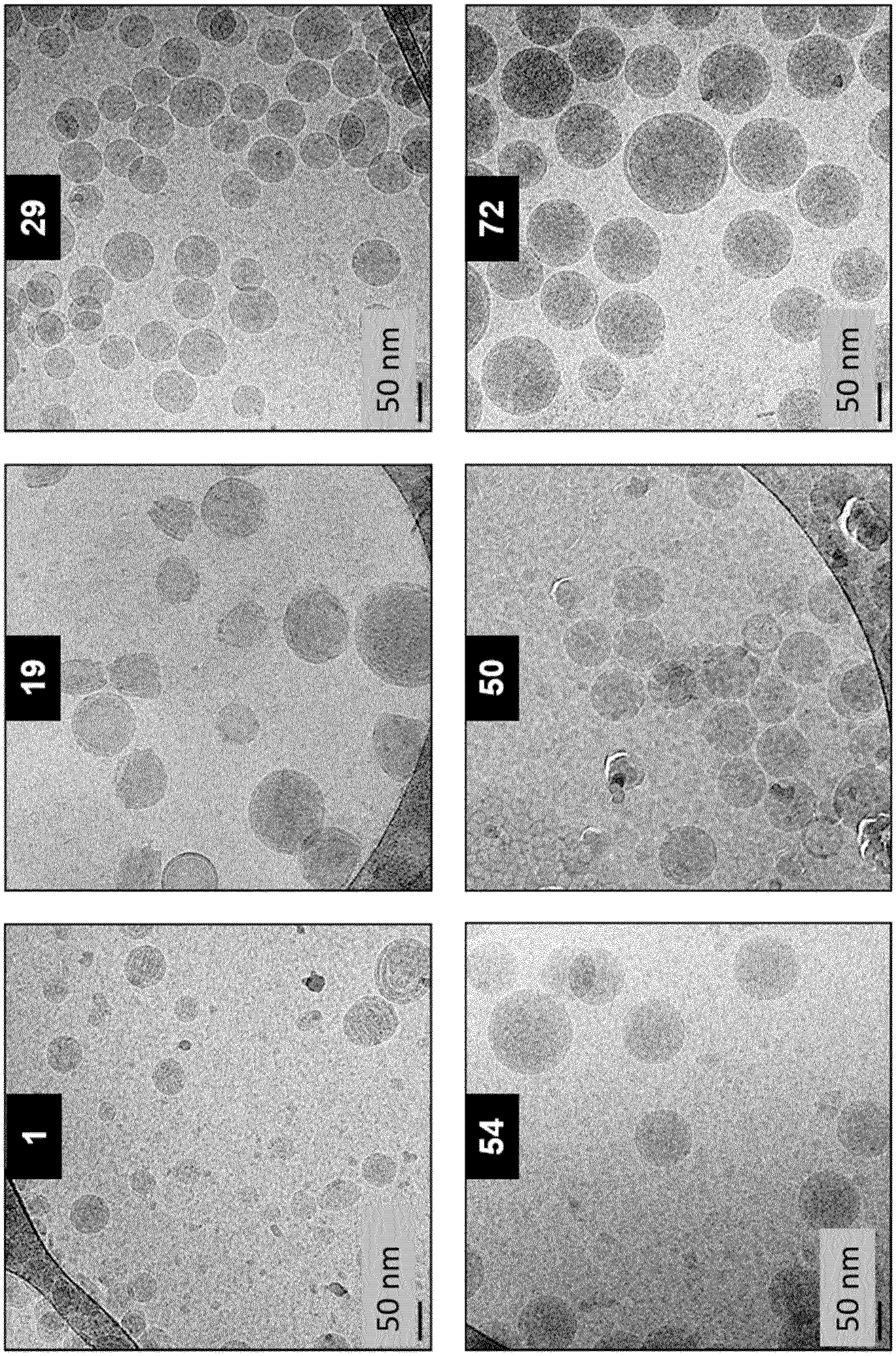
FIG. 5: Representative cryogenic transmission electron micrographs, showing that the lipid composition of apolipoprotein lipid nanoparticles (aNP) containing siRNA (siRNA-aNP) according to certain embodiments of the invention can be employed to influence the morphology and size of these aNPs. All the library's individual siRNA-aNP formulations were subjected to cryogenic electron transmission electron microscopy using a FEI TITAN 300 kV to determine particle size, morphology and formulation homogeneity (scale bars 50 nm).

Example 5. Representative Cryogenic Transmission Electron Micrographs, Showing that the Lipid Composition of Apolipoprotein Lipid Nanoparticles (aNP) Containing siRNA (siRNA-aNP) can be Employed to Influence the Morphology and Size of these aNPs (FIG. 5)

All the library's individual siRNA-aNP formulations were subjected to cryogenic electron transmission electron microscopy using a FEI TITAN 300 kV to determine particle size, morphology and formulation homogeneity (scale bars 50 nm).

Cryogenic transmission electron microscopy (cryo-TEM) images were taken from all the individual formulations of the library containing 72 siRNA-aNPs. The formulations of the 72 siRNA-aNPs are as described in Example 4. The results indicate that the formulations had a spherical appearance and that their morphology, internal structure, size, and homogeneity was dependent on the formulation composition. For example, where formulations with a low amount of cholesterol and tri-glycerides such as formulation 1 appeared to have an internal structure containing multiple concentric rings, formulations with a high amount of cholesterol and tri-glycerides, such as formulation 72, appeared to have an electron dense core surrounded by a surface barrier. Upon inspection of the images, it can be seen that the particles comprised a (distinct) surface barrier layer, possibly but not necessarily a monolayer, and likely composed of phospholipid, cholesterol and apolipoprotein. Without wishing to be bound by any theory, the inventors believe that the layer shields and protects the siRNA that is buried in the core by the ionizable cationic lipid.

Example 6. Apolipoprotein Lipid Nanoparticles (aNP) Containing Firefly Luciferase siRNA (siRNA-aNP) Induce Potent Reporter Gene Expression Knockdown In Vitro (FIG. 6

The functional effect of the siRNA-aNP library's 72 individual formulations was determined by measuring firefly luciferase knockdown in murine RAW264.7 macrophages. More particularly, murine RAW264.7 macrophages were transfected with the pmirGLO plasmid (Promega, E1330) for stable dual-reporter luciferase expression (Firefly and Renilla luciferase) and subsequently exposed to the library's individual siRNA-aNP formulations containing firefly luciferase (Fluc) siRNA for 48 hours. Luminescence assays were performed according to the manufactures protocol (Dual-Glo Luciferase Assay System, Promega, E2920). Data were corrected for control siRNA-aNP formulations containing non-specific siRNA. The formulations of the 72 siRNA-aNPs are as described in Example 4.

Figure 6:
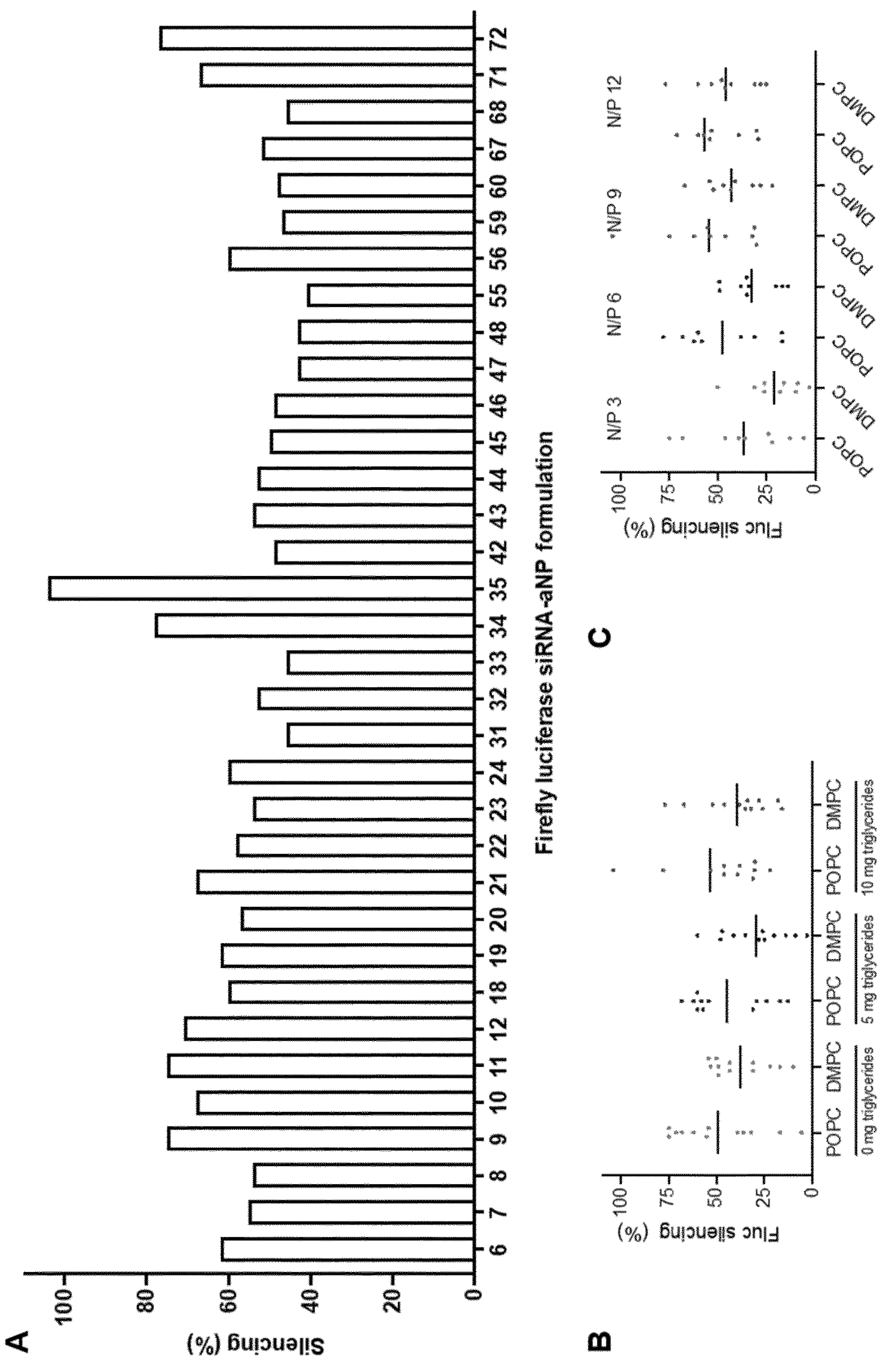
FIG. 6: Apolipoprotein lipid nanoparticles (aNP) according to certain embodiments of the invention containing Firefly luciferase siRNA (siRNA-aNP) induce potent reporter gene expression knockdown in vitro. (A) Murine RAW264.7 macrophages transfected with the pmirGLO plasmid (Promega) for stable dual-reporter luciferase expression (Firefly and Renilla luciferase) were exposed to the library's individual siRNA-aNP formulations containing firefly luciferase (Fluc) siRNA for 48 hours. Luminescence assays were performed according to the manufacturer's protocol (Dual-Glo Luciferase Assay System, Promega). Data are corrected for control siRNA-aNP formulations containing non-specific siRNA. (B) Firefly luciferase expression knockdown data displayed according to the library's individual siRNA-aNP formulations' phospholipid type and triglyceride content. (C) Firefly luciferase expression knockdown data displayed according to the library's individual siRNA-aNP formulations' phospholipid type and N/P ratios. The N/P ratio is the used ratio of positively-chargeable amine (N=nitrogen) groups of ionizable cationic materials to negatively-charged nucleic acid phosphate (P) groups).

The results show that depending on the formulation composition, firefly luciferase siRNA-aNPs induced potent gene silencing compared to non-specific siRNA-aNPs. FIG. 6A shows some representative formulations that lead to a silencing of 40% or more, and even up to 100%. The results in FIG. 6B show that adding tri-glycerides to the formulations can affect their functional effects irrespective of the formulation's phospholipid type. The results in FIG. 6 C show increasing the N/P ratio 3 to 9 appeared to improve functional effects, irrespective of the formulation's phospholipid type.

Figure 7:
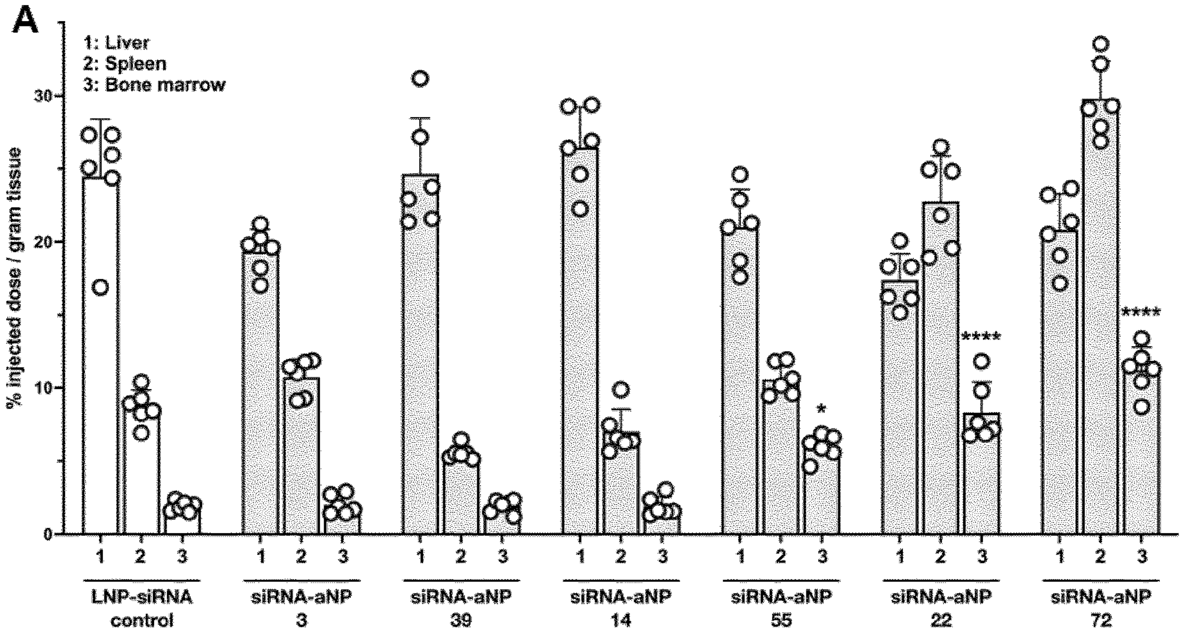
FIG. 7: Apolipoprotein lipid nanoparticles (aNP) according to certain embodiments of the invention containing radiolabeled siRNA (siRNA-aNP) localize to hematopoietic tissues including the spleen and the bone marrow following intravenous administration in mice. (A) Biodistribution of siRNA-aNP following intravenous administration in mice. C57BL/6 mice (n=6 per formulation) were intravenously injected with siRNA-aNP formulations of the invention or with comparative example LNP formulations# containing zirconium 89-radiolabeled non-specific siRNA at a dose of 2 mg/kg siRNA. 24 hours after injection, mice were sacrificed, and organs collected for quantitative analysis by gamma counting. Data are presented as mean±SD of % injected dose per gram of tissue (% ID/g) and analyzed by two-way ANOVA with Tukey's post test. * Indicates p-value <0.05, **** indicates p-value <0.0001. (B) Biodistribution results displayed as bone marrow to liver ratio of % injected dose per gram of tissue (% ID/g). # The LNP-siRNA comparative example is composed of Dlin-MC3-DMA, DSPC, cholesterol and PEG-DMG (50:38.5:10:1.5 mol %), with included siRNA.
Figure 7:
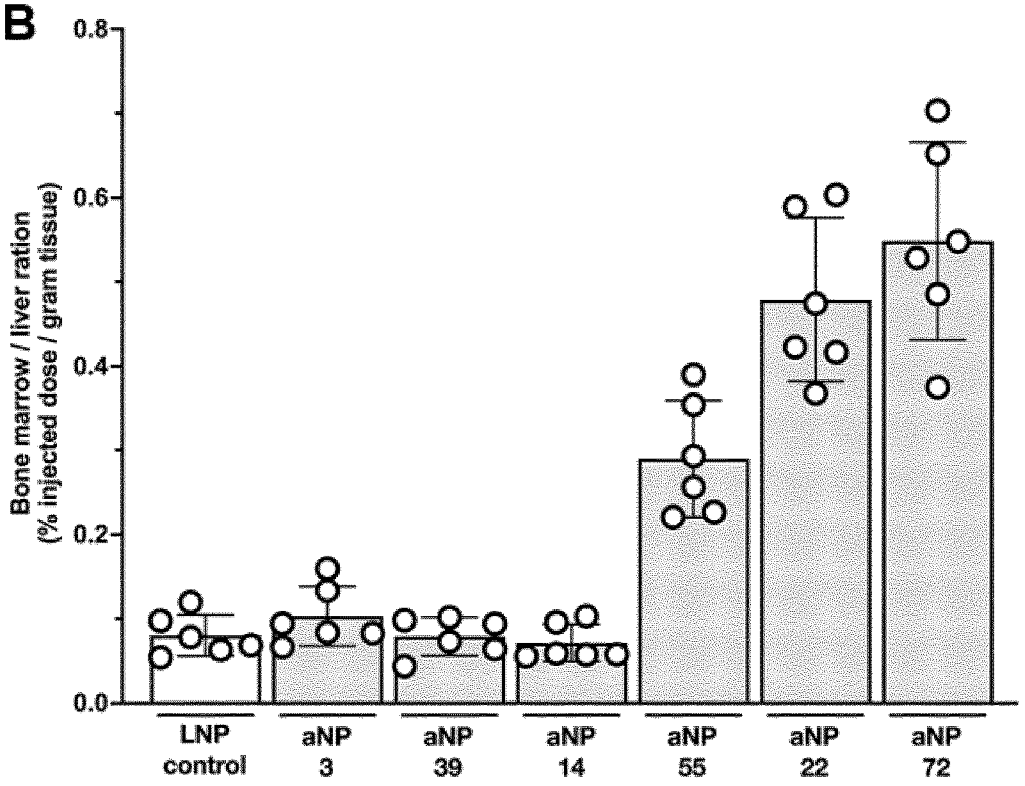

Example 7. Apolipoprotein Lipid Nanoparticles (aNP) Containing Radiolabeled siRNA (siRNA-aNP) Localize to Hematopoietic Tissues Including the Spleen and the Bone Marrow Following Intravenous Administration in Mice (FIG. 7)

siRNA-aNP formulations 3, 39, 14, 55, 22 and 72 were all formulations according to certain embodiments of the invention and comprised varying amounts of phospholipid (namely 1-palmitoyl-2-oleoyl-sn-glycero-3-phosphocholine (POPC) or 1,2-dimyristoyl-sn-glycero-3-phosphocholine (DMPC)), cholesterol, an ionizable cationic lipid (namely Dlin-MC3-DMA), triglycerides, apolipoprotein A1 (prepared as described in Example 3) and siRNA. The formulations of the siRNA-aNPs are as described in Table 1 (FIG. 11).

FIG. 7A shows the biodistribution of siRNA-aNP following intravenous administration in mice. C57BL/6 mice (n=6 per formulation) were intravenously injected with illustrative siRNA-aNP formulations of the invention or with comparative example LNP formulations# containing zirconium 89-radiolabeled non-specific siRNA at a dose of 2 mg/kg siRNA. The LNP control formulations comprised PEGylated lipids. 24 hours after injection, mice were sacrificed, and organs collected for quantitative analysis by gamma counting. Data are presented as mean±SD of % injected dose per gram of tissue (% ID/g) and analyzed by two-way ANOVA with Tukey's post test. * Indicates p-value <0.05, **** indicates p-value <0.0001.

FIG. 7B shows the biodistribution results displayed as bone marrow to liver ratio of % injected dose per gram of tissue (% ID/g). # The LNP-siRNA comparative example was composed of Dlin-MC3-DMA, DSPC, cholesterol and PEG-DMG (50:38.5:10:1.5 mol %), with included siRNA.

In conclusion, the data show that the aNPs containing siRNA as payload according to certain embodiments of the invention were able to target tissues that are associated with the presence of immune cells following systemic injection. Furthermore, the composition of the siRNA-aNPs could be used to steer targeting and subsequent biodistribution.

Figure 8:
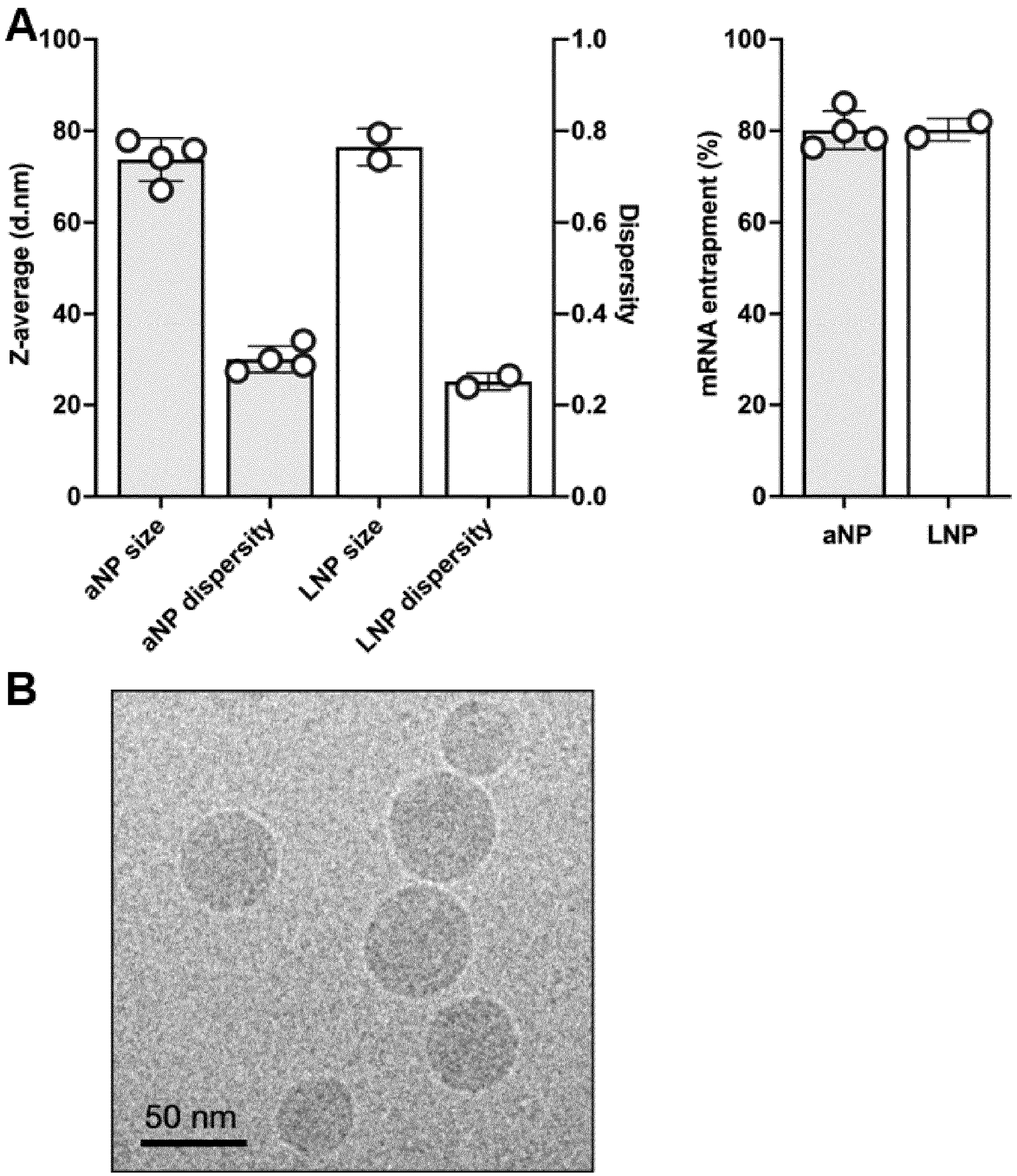
FIG. 8: Apolipoprotein lipid nanoparticles (aNP) according to certain embodiments of the invention can encapsulate mRNA to yield stable formulations and induce gene expression in vitro. (A) Firefly luciferase messenger RNA (mRNA)-containing aNP formulations were prepared using the method described in FIG. 2. The mRNA-aNP formulations according to certain embodiments of the invention and the LNP-mRNA comparative example formulations# were characterized with respect to their particle size and particle size dispersity using dynamic light scattering (DLS). mRNA entrapment efficiency was assessed using the Ribogreen assay. (B) Representative mRNA-aNP cryogenic transmission electron micrograph (scale bar 50 nm). (C) Human HEK293 cells were exposed for 24 hours to firefly mRNA-containing aNPs and comparative example LNPs. Reporter gene expression (left) was determined by luminescence, and cell viability (right) was determined by MTT assay, indicating mRNA-aNP induce dose-dependent firefly luciferase expression without inducing toxicity in vitro. (D) Murine RAW264.7 macrophages were exposed to firefly mRNA-containing aNP for 24 hours. Gene expression was determined by luminescence, indicating mRNA-aNP induce dose-dependent firefly luciferase expression in macrophage cell cultures. (E). Primary murine bone marrow-derived macrophages were exposed to firefly mRNA-containing aNP for 24 hours. Gene expression was determined by luminescence, indicating mRNA-aNP induce dose-dependent firefly luciferase expression in primary cells.# The LNP-mRNA comparative example is composed of Dlin-MC3-DMA, DSPC, cholesterol and PEG-DMG (50:38.5:10:1.5 mol %), with included mRNA.
Figure 8:
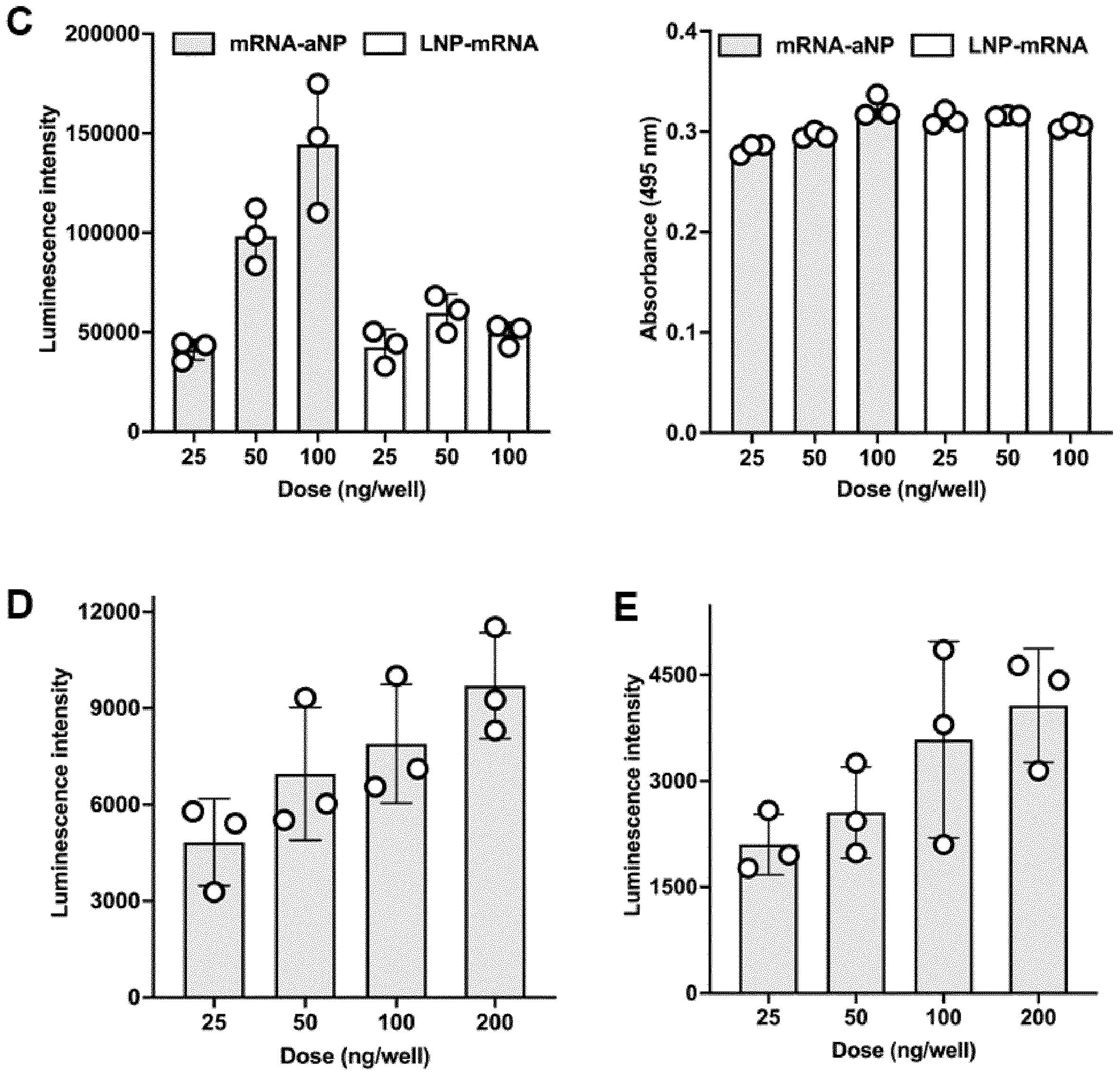

Example 8. Apolipoprotein Lipid Nanoparticles (aNP) can Encapsulate mRNA to Yield Stable Formulations and Induce Gene Expression In Vitro (FIG. 8)

Firefly luciferase messenger RNA (mRNA; Trilink Biotechnologies—L7602)-containing aNP formulations were prepared using the method described in Example 2. The mRNA-aNP formulations of the invention and the LNP-mRNA comparative example formulations# were characterized with respect to their particle size and particle size dispersity using dynamic light scattering (DLS) (FIG. 8A, left panel). mRNA entrapment efficiency was assessed using the Ribogreen assay (FIG. 8A, right panel).

FIG. 8B shows a representative mRNA-aNP (according to certain embodiments of the invention) cryogenic transmission electron micrograph (scale bar 50 nm).

Human HEK293 cells were exposed for 24 hours to firefly mRNA-containing aNPs and comparative example LNPs. Reporter gene expression was determined by luminescence (FIG. 8C, left panel), and cell viability was determined by MTT assay (Promega—G3582) (FIG. 8C, right panel), indicating mRNA-aNP induced dose-dependent firefly luciferase expression without inducing toxicity in vitro.

Murine RAW264.7 macrophages were exposed to firefly mRNA-containing aNP for 24 hours. Gene expression was determined by luminescence, indicating mRNA-aNP induced dose-dependent firefly luciferase expression in macrophage cell cultures (FIG. 8D).

Primary murine bone marrow-derived macrophages were exposed to firefly mRNA-containing aNP for 24 hours. Gene expression was determined by luminescence, indicating mRNA-aNP induced dose-dependent firefly luciferase expression in primary cells (FIG. 8E). #The LNP-mRNA comparative example was composed of Dlin-MC3-DMA, DSPC, cholesterol and PEG-DMG (50:38.5:10:1.5 mol %), with included mRNA.

Figure 9:
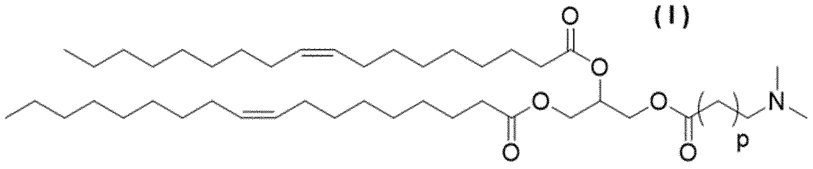
FIG. 9: Molecular structures of monovalent ionizable cationic materials that can be used to complex RNA (or other nucleic acids), for incorporation into apolipoprotein lipid nanoparticles (aNP) according to certain embodiments of the invention. The examples 1-15 as referred to in FIG. 9, are the sub-examples 1-15 of Example 9.
Figure 9:
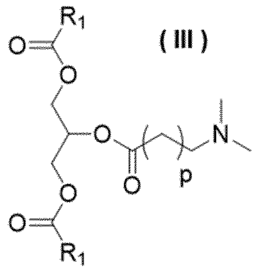
Figure 9:
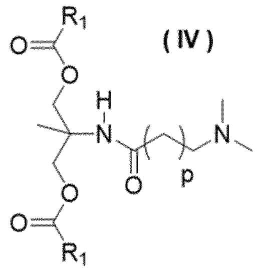
Figure 9:
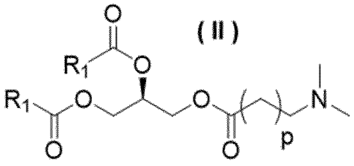
Figure 9:
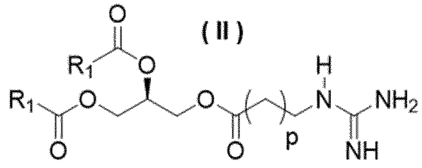
Figure 9:
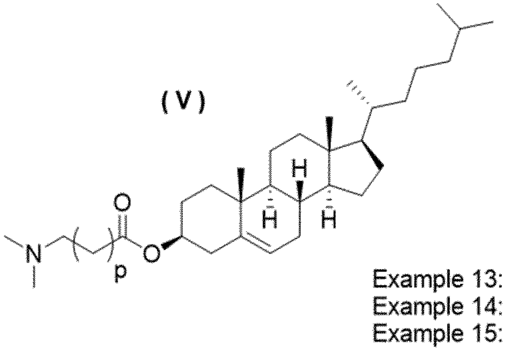

Example 9. The Synthesis of Ionizable Cationic Lipids According to Formulas (I) to (V) (as Depicted in FIG. 9)

Starting compounds, reagents, solvents, deuterated solvents and (purification) materials have been purchased from commercial sources (e.g. Merck, ABCR, Cambridge Isotopes Laboratories, etc.). NMR analyses were conducted on a Bruker 400 MHz spectrometer. MALDI-TOF-MS analyses were conducted on a Bruker Autoflex spectrometer. HPLC-MS was conducted on a LCQ Fleet (Thermo Scientific) equipped with an ESI ion-trap MS detector as well as a PDA detector, applying a C18 reversed phase column (Kinetex 5 μm particles, 2.1 mm (i.d.)×50 mm, Phenomenex), and using an eluent gradient from 5% acetonitrile and 95% water to 95% acetonitrile and 5% water (both with 0.1% formic acid) at a flow rate of 0.2 mL/min.

Examples for Formula (II) (ICG-A Type): 1,2 Glycerol Ionizable Cationic Lipids Scheme A: Synthetic route to ionizable cationic lipids as according to Formula (II) with ICG-A type.

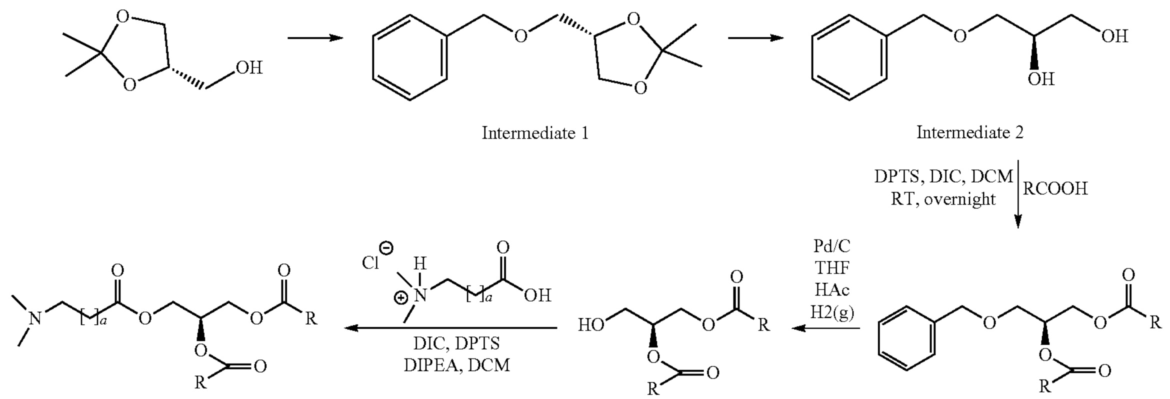

Intermediate 1

Intermediate 2 a = 1 or 2

R = $C_{11}H_{23}$ or $C_{10}H_{21}$ or $C_9H_{19}$ or $C_{17}H_{35}$

R = $C_{11}H_{23}$ or $C_{10}H_{21}$ or $C_9H_{19}$

Intermediate 3, 4 and 5

DPTS = 4-(dimethyl-amino)-pyridinium 4-toluene-sulfonate; DIC = N,N'-di-isopropyl-carbodiimide; DCM = dichloromethane; RT = room temperature; DIPEA = di-isopropylethylamine; Pd/C = palladium on carbon; THF = tetrahydrofuran; HAc = acetic acid; H2(g) = hydrogen gas.

Intermediate 1: (S)-4-((Benzyloxy)methyl)-2,2-dimethyl-1,3-dioxolane

This compound was obtained via the benzyl protection of (S)-(2,2-dimethyl-1,3-dioxolan-4-yl)methanol according to a literature procedure (Lee, Jong-Dae; et al, Organic Letters (2007), 9(2), 323-326). Yield: 16.8 g (88%). The $^1$H-NMR spectrum was in agreement with the desired structure.

Intermediate 2: (R)-3-((Benzyloxy)propane-1,2-diol

This compound was obtained via the deprotection of the diol group in (S)-4-((benzyloxy)methyl)-2,2-dimethyl-1,3-dioxolane using acetic acid and water according to a literature procedure (Lee, Jong-Dae; et al, Organic Letters (2007), 9(2), 323-326). Yield: 9.45 g (76%). The $^1$H-NMR spectrum was in agreement with the desired structure.

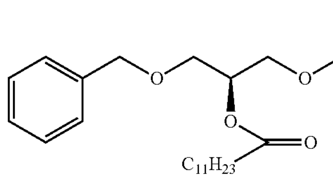

Intermediate 3: (S)-3-(Benzyloxy)propane-1,2-diyl di-dodecanoate

This compound was obtained via the coupling of (R)-3-((benzyloxy)propane-1,2-diol (3 g; 16.5 mmol) with dodecanoic acid (6.92 g; 34.6 mmol; 2.1 moleqs) in DCM (23 mL) using DPTS (0.4 g; 1.36 mmol; about 0.1 moleqs) and DIC (5.2 g; 41.3 mmol; 2.5 moleqs) as couple reagents. The reaction mixture was stirred for 24 hours at room temperature, after which the reaction mixture was filtrated over a plug of celite. The crude mixture was purified via silica column chromatography using 1/9 EtOAc/Heptane as eluent. Yield: 8.21 g (91%). The $^1$H-NMR spectrum was in agreement with the desired structure.

$^1$H NMR (400 MHz, Chloroform-d) δ 7.43-7.27 (m, 5H, Ar—H), 5.37-5.06 (m, 1H, chiral $OCH_2CHCH_2O$), 4.67-4.43 (m, 2H, $OCH_2$—Bn), 4.43-4.08 (m, 2H, $CHCH_2OCO$), 3.67-3.31 (m, 2H, $CHCH_2OCH_2$), 2.29 (dt, J=16.9, 7.5 Hz, 4H, $CH_2CH_2OCO$), 1.59 (dq, J=10.6, 7.1 Hz, 4H, $CH_2CH_2COO$), 1.26 (d, J=4.2 Hz, 32H, $CH_3(CH_2)_8CH_2$), 0.88 (t, J=6.8 Hz, 6H, $CH_3CH_2$).

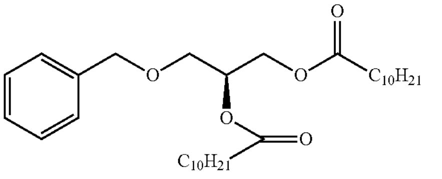

Intermediate 4: (S)-3-(Benzyloxy)propane-1,2-diyl di-undecanoate

The reaction between (R)-3-((benzyloxy)propane-1,2-diol and undecanoic acid was performed in a similar way as done for Intermediate 3. Yield: 478 mg (90%). The $^1$H-NMR spectrum was in agreement with the desired structure.

$^1$H NMR (400 MHz, Chloroform-d) δ 7.54-7.26 (m, 5H, Ar—H), 5.33-5.12 (m, 1H, chiral $OCH_2CHCH_2O$), 4.66-4.44 (m, 2H, $OCH_2$—Bn), 4.35-4.19 (m, 2H, $CHCH_2OCO$), 3.59 (d, J=5.3 Hz, 2H, $CHCH_2OCH_2$), 2.30 (dt, J=17.0, 7.5 Hz, 4H, $CH_2CH_2COO$), 1.74-1.49 (m, 4H, $CH_2CH_2COO$), 1.50-1.08 (m, 28H, $CH_3(CH_2)_7CH_2$), 0.88 (t, J=6.8 Hz, 6H, $CH_3CH_2$).

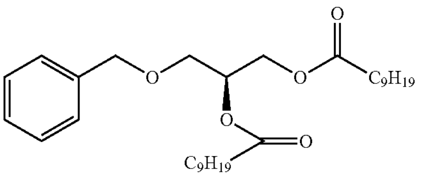

Intermediate 5: (S)-3-(Benzyloxy)propane-1,2-diyl di-decanoate

The reaction between (R)-3-((benzyloxy)propane-1,2-diol and decanoic acid was performed in a similar way as done for Intermediate 3. Yield: 505 mg (93%). The $^{1}$H-NMR spectrum was in agreement with the desired structure.

$^{1}$H NMR (400 MHz, Chloroform-d) δ 7.42-7.27 (m, 5H, Ar—H), 5.24 (dtd, J=6.4, 5.2, 3.7 Hz, 1H, chiral $OCH_2CHCH_2O$), 4.65-4.44 (m, 2H, $OCH_2$—Bn), 4.35-4.19 (m, 2H, $CHCH_2OCO$), 3.59 (dd, J=5.2, 1.2 Hz, 2H, $CHCH_2OCH_2$), 2.30 (dt, J=16.9, 7.5 Hz, 4H, $CH_2CH_2COO$), 1.74-1.51 (m, 4H, $CH_2CH_2COO$), 1.51-1.08 (m, 24H, $CH_3(CH_2)_6CH_2$), 1.08-0.67 (m, 6H, $CH_3CH_2$).

Subexample 1: (R)-3-((4-(Dimethylamino)butanoyl)oxy)propane-1,2-diyl di-dodecanoate Step 1, Building Block 1: (S)-3-Hydroxypropane-1,2-diyl di-dodecanoate

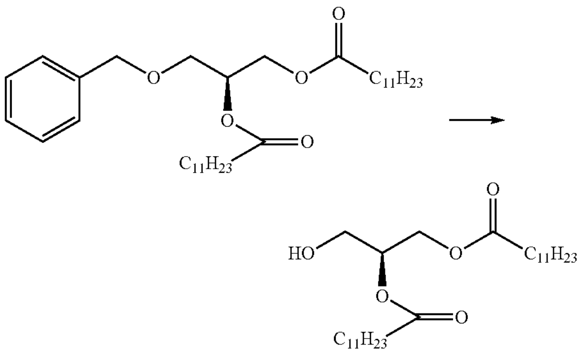

This compound was obtained via debenzylation of (S)-3-(benzyloxy)propane-1,2-diyl di-dodecanoate (Intermediate 3; 8.21 g; 15 mmol) using a hydrogen balloon and Pd/C (250 mg; Degussa type) as catalyst in THF (50 mL) and acetic acid (0.5 mL). The reaction mixture was stirred for 24 hours at room temperature, after which the reaction mixture was filtrated over a plug of celite and evaporated to dryness. The crude mixture was dissolved in chloroform and washed with demi-water and then with a saturated NaCl-solution (aq). An oil was obtained that slowly became solid. Yield: 7.1 g (100%). The $^{1}$H-NMR spectrum was in agreement with the desired structure.

$^{1}$H NMR (400 MHz, Chloroform-d) δ 5.09 (p, J=5.0 Hz, 1H, chiral $OCH_2CHCH_2O$), 4.48-4.19 (m, 2H, $CHCH_2OCO$), 3.73 (t, J=4.0 Hz, 2H, $CHCH_2OH$), 2.33 (dt, J=9.0, 7.5 Hz, 4H, $CH_2CH_2COO$), 1.61 (h, J=5.2, 3.1 Hz, 4H, $CH_2CH_2COO$), 1.28 (d, J=14.7 Hz, 32H, $CH_3(CH_2)_8CH_2$), 1.04-0.66 (m, 6H, $CH_3CH_2$).

Step 2: (R)-3-((4-(Dimethylamino)butanoyl)oxy)propane-1,2-diyl di-dodecanoate

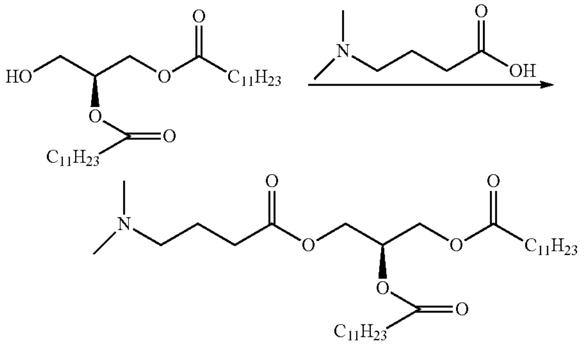

This compound was obtained via coupling of (S)-3-hydroxypropane-1,2-diyl di-dodecanoate (Building Block 1; 0.1 g; 0.22 mmol) to 4-(dimethylamino)butanoic acid hydrochloride (55 mg; 0.33 mmol; 1.5 moleqs) in DCM (1 mL) using DIPEA (74 mg; 0.58 mmol; 2.6 moleqs), DPTS (6.4 mg; 0.1 moleqs) and DIC (41.4 mg; 0.33 mmol; 1.5 moleqs) as reagents. The reaction mixture was stirred for 24 hours at room temperature, after which the reaction mixture was filtrated over a plug of celite, the filtrate was diluted with DCM and was subsequently washed with 0.1M HCl (aq), 0.1 M NaOH (aq) and saturated NaCl (aq). The organic layer was dried with $Na_2SO_4$. The crude mixture was stirred in acetonitrile and filtrated. The filtrate was evaporated to dryness to afford an oil that slowly became solid at 4° C. Yield: 90 mg (80%). The $^{1}$H-NMR spectrum was in agreement with the desired structure.

$^{1}$H NMR (400 MHz, Chloroform-d) δ 5.27 (tt, J=6.0, 4.3 Hz, 1H, $OCH_2CHCH_2O$), 4.30-4.15 (4H, $CHCH_2OCO$), 2.44-2.25 (m, 8H, $CH_2CH_2COO$ and $NCH_2$), 2.21 (s, 6H, $N(CH_3)_2$), 1.78 (p, J=7.4 Hz, 2H, $NCH_2CH_2CH_2COO$), 1.70-1.51 (m, 4H, $CH_2CH_2COO$), 1.40-1.08 (m, 32H, $CH_3(CH_2)_8CH_2$), 1.08-0.69 (m, 6H, $CH_3CH_2$).

MALDI-TOF-MS (CHCA matrix, positive reflector mode): m/z $(M+H)^+$=570.48. Calculated: $C_{33}H_{63}NO_6$ (exact mass 569.47; molecular weight 569.87).

Subexample 2: (R)-3-((4-(Dimethylamino)butanoyl)oxy)propane-1,2-diyl di-undecanoate Step 1, Building Block 2: (S)-3-Hydroxypropane-1,2-diyl di-undecanoate

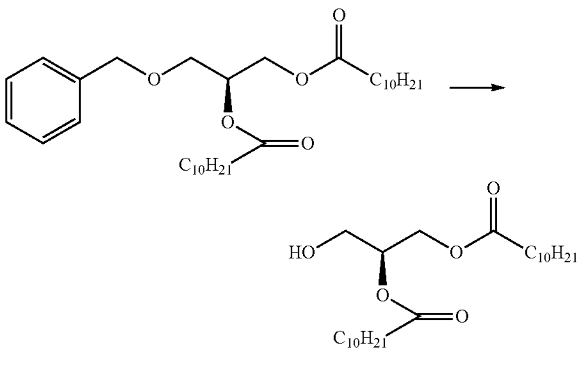

The hydrogenation reaction of (S)-3-(benzyloxy)propane-1,2-diyl di-undecanoate (Intermediate 4) was performed in a similar way as done for the preparation of Building Block 1.Yield: 405 mg (80%). The $^1$H-NMR spectrum was in agreement with the desired structure.

$^1$H NMR (400 MHz, Chloroform-d) δ 5.09 (p, J=5.1 Hz, 1H, chiral $OCH_2CHCH_2O$), 4.42-4.20 (m, 2H, $CHCH_2OCO$), 3.94-3.52 (m, 2H, $CHCH_2OH$), 2.33 (dt, J=9.1, 7.5 Hz, 4H, $CH_2CH_2COO$), 1.76-1.53 (m, 4H, $CH_2CH_2COO$), 1.28 (d, J=14.9 Hz, 28H, $CH_3(CH_2)_7CH_2$), 0.88 (t, J=6.8 Hz, 6H, $CH_3CH_2$).

Step 2: (R)-3-((4-(Dimethylamino)butanoyl)oxy)propane-1,2-diyl di-undecanoate

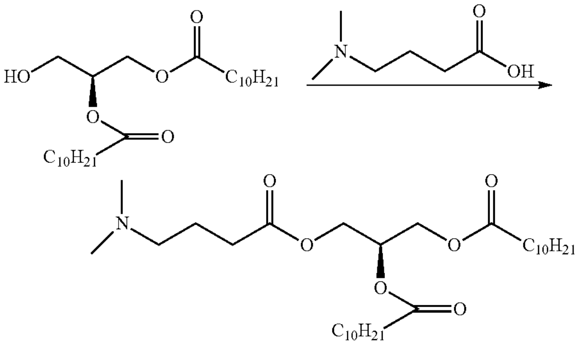

The reaction between (S)-3-hydroxypropane-1,2-diyl di-undecanoate (Building Block 2) and 4-(dimethylamino) butanoic acid hydrochloride was performed in a similar way as done for the preparation of Subexample 1 (step 2). Yield: 96 mg (87%). The $^1$H-NMR spectrum was in agreement with the desired structure.

$^1$H NMR (400 MHz, Chloroform-d) δ 5.27 (tt, J=6.0, 4.3 Hz, 1H, $OCH_2CHCH_2O$), 4.30-4.15 m, 4H, $CHCH_2OCO$), 2.55-2.25 (m, 8H, $(CH_3)_2NCH_2CH_2CH_2COO$, $(CH_3)_2NCH_2CH_2CH_2COO$ and $CH_2CH_2COO$ of the Cao tails), 2.21 (s, 6H, $N(CH_3)_2$), 1.78 (p, J=7.4 Hz, 2H, $NCH_2CH_2CH_2COO$), 1.61 (td, J=7.3, 6.8, 3.1 Hz, 4H, $CH_2CH_2COO$), 1.28 (d, J=14.1 Hz, 28H, $CH_3(CH_2)_7CH_2$), 1.06-0.67 (m, 6H, $CH_3CH_2$).

MALDI-TOF-MS (CHCA matrix, positive reflector mode): m/z $(M+H)^+$=542.45, $(M+Na)^+$=564.43. Calculated: $C_{31}H_{59}NO_6$(exact mass 541.43; molecular weight 541.81).

Subexample 3: (R)-3-((4-(Dimethylamino)butanoyl)oxy)propane-1,2-diyl di-decanoate

Step 1, Building Block 3: (S)-3-Hydroxypropane-1,2-diyl di-decanoate

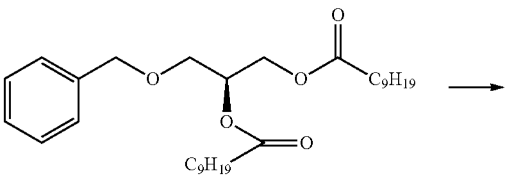

-continued

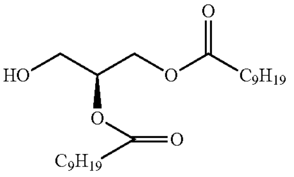

The hydrogenation reaction of (S)-3-(benzyloxy)propane-1,2-diyl di-decanoate (Intermediate 5) was performed in a similar way as done for the preparation of Building Block 1. Yield: 412 mg (100%). The $^1$H-NMR spectrum was in agreement with the desired structure.

$^1$H NMR (400 MHz, Chloroform-d) δ 5.09 (p, J=5.0 Hz, 1H, chiral $OCH_2CHCH_2O$), 4.46-4.20 (m, 2H, $CHCH_2OCO$), 3.74 (t, J=5.6 Hz, 2H, $CHCH_2OH$), 2.33 (dt, J=9.1, 7.5 Hz, 4H, $CH_2CH_2COO$), 1.78-1.54 (m, 4H, $CH_2CH_2COO$), 1.28 (d, J=8.8 Hz, 24H, $CH_3(CH_2)_6CH_2$), 1.09-0.51 (m, 6H, $CH_3CH_2$).

Step 2: (R)-3-((4-(Dimethylamino)butanoyl)oxy)propane-1,2-diyl di-decanoate

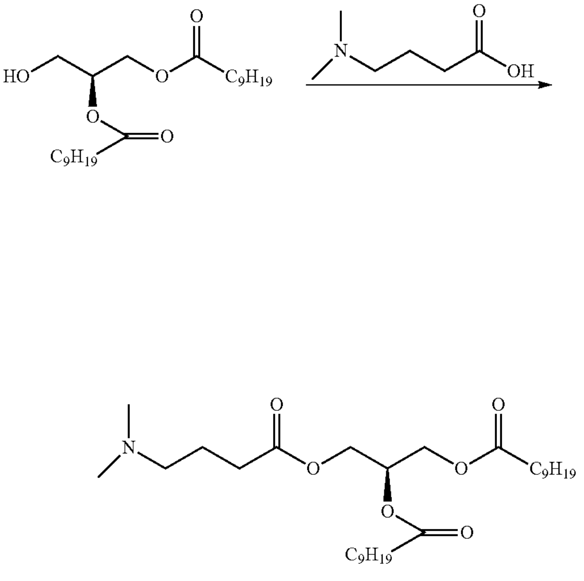

The reaction between (S)-3-hydroxypropane-1,2-diyl di-decanoate (Building Block 3) and 4-(dimethylamino)butanoic acid hydrochloride was performed in a similar way as done for Subexample 1 (step 2), albeit without using DIPEA. Yield: 110 mg (80%). The $^1$H-NMR spectrum was in agreement with the desired structure.

$^1$H NMR (400 MHz, Chloroform-d) δ 5.27 (tt, J=6.0, 4.3 Hz, 1H, $OCH_2CHCH_2O$), 4.30-4.15 m, 4H, $CHCH_2OCO$), 2.48-2.23 (m, 8H, $(CH_3)_2NCH_2CH_2CH_2COO$, $(CH_3)_2NCH_2CH_2CH_2COO$ and $CH_2CH_2COO$ of the $C_9$ tails), 2.21 (s, 6H, $N(CH_3)_2$), 1.78 (p, J=7.4 Hz, 2H, $NCH_2CH_2CH_2COO$), 1.61 (ddt, J=11.7, 7.8, 4.7 Hz, 4H, $CH_2CH_2COO$), 1.40-1.12 (m, 24H, $CH_3(CH_2)_6CH_2$), 1.02-0.73 (m, 6H, $CH_3CH_2$).

MALDI-TOF-MS (CHCA matrix, positive reflector mode): m/z $(M+H)^+$=514.43. Calculated: $C_{29}H_{55}NO_6$ (exact mass 513.40; molecular weight 513.76).

Subexample 4: (R)-3-((3-(Dimethylamino)propanoyl)oxy)propane-1,2-diyl di-dodecanoate

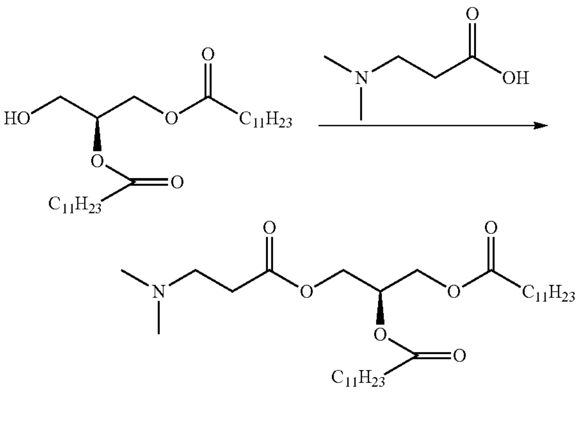

The reaction between (S)-3-hydroxypropane-1,2-diyl di-dodecanoate (Building Block 1) and 3-(dimethylamino) propanoic acid hydrochloride was performed in a similar way as done for the preparation of Subexample 1 (step 2). Yield: 83 mg (68%). The $^1$H-NMR spectrum was in agreement with the desired structure.

$^1$H NMR (400 MHz, Chloroform-d) δ 5.27 (tt, J=6.0, 4.3 Hz, 1H, $OCH_2CHCH_2O$), 4.40-4.16 (m, 4H, $CHCH_2OCO$), 2.68-2.55 (m, 2H, $(CH_3)_2NCH_2CH_2COO$), 2.55-2.43 (m, 2H, $(CH_3)_2NCH_2CH_2COO$), 2.31 (td, J=7.5, 3.7 Hz, 4H, $CH_2CH_2COO$ of the $C_{11}$ tails), 2.23 (s, 6H, $N(CH_3)_2$), 1.62 (qt, J=7.0, 3.4 Hz, 4H, $CH_2CH_2COO$), 1.27 (d, J=9.9 Hz, 32H, $CH_3(CH_2)_8CH_2$), 1.09-0.64 (m, 6H, $CH_3CH_2$).

MALDI-TOF-MS (CHCA matrix, positive reflector mode): m/z $(M+H)^+$=556.48, $(M+Na)^+$=578.44. Calculated: $C_{32}H_{61}NO_6$ (exact mass 555.45; molecular weight 555.84).

Subexample 5: (R)-3-((3-(Dimethylamino)propanoyl)oxy)propane-1,2-diyl di-undecanoate

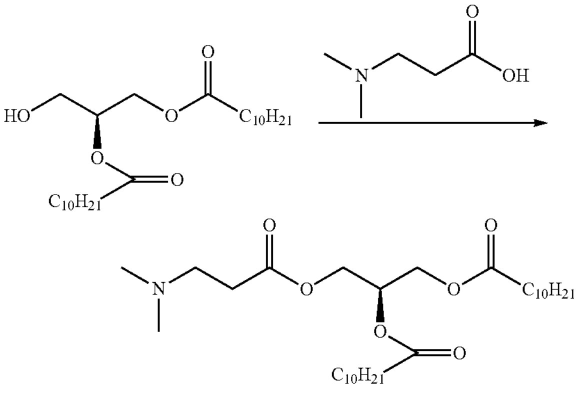

The reaction between (S)-3-hydroxypropane-1,2-diyl di-undecanoate (Building Block 2) and 3-(dimethylamino) propanoic acid hydrochloride was performed in a similar way as done for the preparation of Subexample 1 (step 2). Yield: 108 mg (82%). The $^1$H-NMR spectrum was in agreement with the desired structure.

$^1$H NMR (400 MHz, Chloroform-d) δ 5.27 (tt, J=6.0, 4.3 Hz, 1H, $OCH_2CHCH_2O$), 4.31-4.04 (m, 4H, $CHCH_2OCO$), 2.74-2.56 (m, 2H, $(CH_3)_2NCH_2CH_2COO$), 2.56-2.42 (m, 2H, $(CH_3)_2NCH_2CH_2COO$), 2.31 (ddd, J=9.1, 5.6, 2.4 Hz, 4H, $CH_2CH_2COO$ of the Cao tails), 2.25 (d, J=1.2 Hz, 6H, $N(CH_3)_2$), 1.62 (tt, J=7.3, 3.6 Hz, 4H, $CH_2CH_2COO$), 1.51-1.07 (m, 28H, $CH_3(CH_2)_7CH_2$), 1.07-0.66 (m, 6H, $CH_3CH_2$).

MALDI-TOF-MS (CHCA matrix, positive reflector mode): m/z $(M+H)^+$=528.45. Calculated: $C_{30}H_{57}NO_6$ (exact mass 527.42; molecular weight 527.79).

Subexample 6: (R)-3-((3-(Dimethylamino)propanoyl)oxy)propane-1,2-diyl di-decanoate

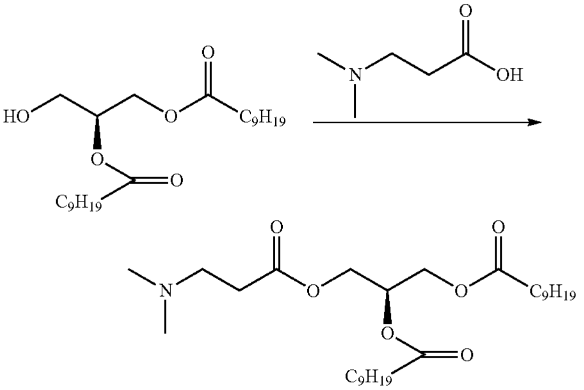

The reaction between (S)-3-hydroxypropane-1,2-diyl di-decanoate (Building Block 3) and 3-(dimethylamino)propanoic acid hydrochloride was performed in a similar way as done for the preparation of Subexample 1 (step 2), albeit without the use of DIPEA. Yield: 131 mg (80%). The $^1$H-NMR spectrum was in agreement with the desired structure.

$^1$H NMR (400 MHz, Chloroform-d) δ 5.42-5.06 (m, 1H, $OCH_2CHCH_2O$), 4.51-4.17 (m, 4H, $CHCH_2OCO$), 2.75-2.53 (m, 4H, $(CH_3)_2NCH_2CH_2COO$, $(CH_3)_2NCH_2CH_2COO$), 2.48-2.03 (m, 10H, $N(CH_3)_2$), $CH_2CH_2COO$ of the $C_9$ tail), 1.61 (td, J=7.3, 3.5 Hz, 4H, $CH_2CH_2COO$), 1.39-1.18 (m, 24H, $CH_3(CH_2)_6CH_2$), 0.88 (t, J=6.8 Hz, 6H, $CH_3CH_2$).

MALDI-TOF-MS (CHCA matrix, positive reflector mode): m/z $(M+H)^+$=500.42. Calculated: $C_{26}H_{53}NO_6$ (exact mass 499.39; molecular weight 499.73).

Subexample 7: (R)-3-((3-(Dimethylamino)propanoyl)oxy)propane-1,2-diyl di-stearate

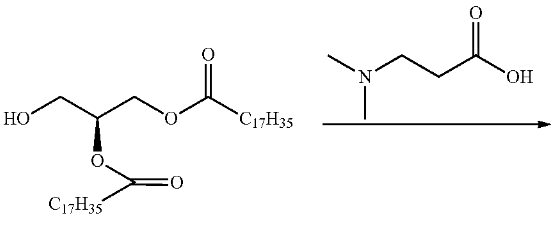

-continued

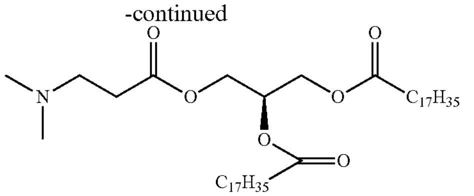

Building Block 4, i.e. (S)-3-hydroxypropane-1,2-diyl distearate was purchased from Merck (1,2-distearoyl-sn-glycerol; CAS 10567-21-2). The reaction between this Building Block 4 and 3-(dimethylamino)propanoic acid hydrochloride was performed in a similar way as done for the preparation of Subexample 1 (step 2), albeit without the use of DIPEA. Also, the reaction was stirred at 40° C. instead of at RT. The $^{1}$H-NMR spectrum was in agreement with the desired structure.

$^{1}$H NMR (400 MHz, Chloroform-d) δ 5.27 (tt, J=6.0, 4.2 Hz, 1H, $OCH_2CHCH_2O$), 4.30-4.16 (m, 4H, $CHCH_2OCO$), 2.60 (dd, J=7.4, 6.0 Hz, 2H, $(CH_3)_2NCH_2CH_2COO$), 2.49 (dd, J=7.5, 6.2 Hz, 2H, $(CH_3)_2NCH_2CH_2COO$), 2.31 (td, J=7.6, 3.7 Hz, 4H, $CH_2CH_2COO$ of the $C_{18}$ tails), 2.23 (s, 6H, $N(CH_3)_2$), 1.70-1.51 (m, 4H, $CH_2CH_2COO$), 1.26 (s, 56H, $CH_3(CH_2)_{14}CH_2$), 0.88 (t, J=6.8 Hz, 6H, $CH_3CH_2$).

Examples for Formula (I) (ICG-A Type): 1,2 Glycerol Ionizable Cationic Lipids

Subexample 8: (R)-3-((4-(Dimethylamino)butanoyl) oxy)propane-1,2-diyl di-oleate

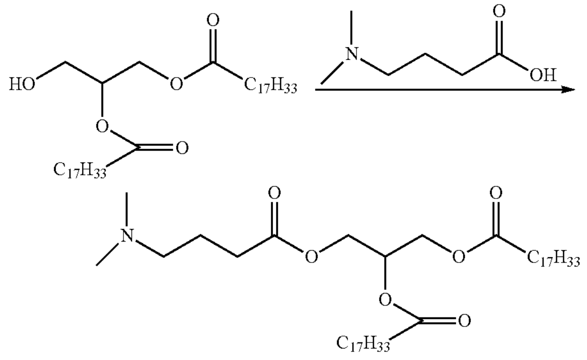

Building Block 5, i.e. (S)-3-hydroxypropane-1,2-diyl dioleate was purchased from ABCR. It is a racemic compound (CAS 2442-61-7). The reaction between Building Block 5 and 4-dimethylamino)butanoic acid hydrochloride was performed in a similar way as done for the preparation of Subexample 1 (step 2). The $^{1}$H-NMR spectrum was in agreement with the desired structure.

$^{1}$H NMR (400 MHz, Chloroform-d) δ 5.35 (td, J=7.2, 6.1, 4.2 Hz, 4H, CH═CH), 5.25 (ddd, J=10.2, 5.8, 4.3 Hz, 1H, $OCH_2CHCH_2O$), 4.30-4.14 (m, 2H, $CHCH_2OCO$), 2.43-2.28 (m, 8H, $(CH_3)_2NCH_2CH_2CH_2COO$, $(CH_3)_2NCH_2CH_2CH_2COO$, $CH_2CH_2COO$ of oleic tails), 2.26 (s, 6H, $N(CH_3)_2$), 2.11-1.92 (m, 8H, $CH_2CH{=}CHCH_2$), 1.81 (p, J=7.4 Hz, 2H, $NCH_2CH_2CH_2COO$), 1.62 (q, J=7.2 Hz, 4H, $CH_2CH_2COO$), 1.42-1.19 (m, 40H, $CH_3(CH_2)_6CH_2CH{=}CH(CH_2)_4CH_2COO$), 0.95-0.82 (m, 6H, $CH_3CH_2$).

Subexample 9: (R)-3-((3-(Dimethylamino)propanoyl)oxy)propane-1,2-diyl di-oleate

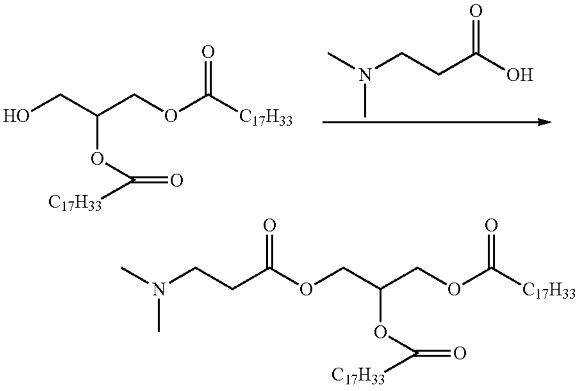

Building Block 5, i.e. (S)-3-hydroxypropane-1,2-diyl dioleate was purchased from ABCR. It is a racemic compound (Cas [2442-61-7]). The reaction between Building Block 5 and 3-dimethylamino)propanoic acid hydrochloride was performed in a similar way as done for the preparation of Subexample 1 (step 2), albeit without the use of DIPEA. Yield: 120 mg (33%). The $^{1}$H-NMR spectrum was in agreement with the desired structure.

$^{1}$H NMR (400 MHz, Chloroform-d) δ 5.46-5.19 (m, 5H, CH═CH, $OCH_2CHCH_2O$), 4.31-4.15 (m, 4H, $CHCH_2OCO$), 2.62 (td, J=7.1, 3.8 Hz, 2H, $(CH_3)_2NCH_2CH_2COO$), 2.50 (td, J=7.2, 2.6 Hz, 2H, $(CH_3)_2NCH_2CH_2COO$), 2.31 (dd, J=9.1, 6.1 Hz, 4H, $CH_2CH_2COO$ of oleic tails), 2.24 (s, 6H, $N(CH_3)_2$), 2.02 (dq, J=12.8, 6.7 Hz, 8H, $CH_2CH{=}CHCH_2$), 1.60 (q, J=7.2 Hz, 4H, $CH_2CH_2COO$), 1.52-1.18 (m, 40H, $CH_3(CH_2)_4CH_2CH{=}CH(CH_2)_4CH_2COO$), 0.99-0.77 (m, 6H, $CH_3CH_2$).

HPLC-MS: (M+H+)=720. Calculated: $C_{44}H_{81}NO_6$ (exact mass; 719.61 molecular weight 720.13).

Example for Formula (III) (ICG-A Type): 1,3 Glycerol Ionizable Cationic Lipids

Subexample 10: 2-((3-(Dimethylamino)propanoyl) oxy)propane-1,3-diyl di-dodecanoate Step 1: 2-Oxopropane-1,3-diyl di-dodecanoate

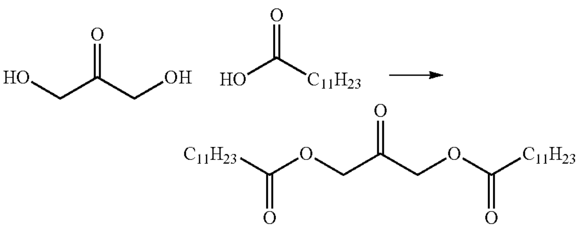

This compound was obtained via the coupling of 1,3-dihydroxypropan-2-one (0.5 gram; 5.6 mmol) with dodecanoic acid (2.28 gram; 11.4 mmol; 2.05 moleqs) in DCM (50 mL) using DIPEA (2.32 mL; 13.3 mmol; 2.4 moleqs), DMAP (67 milligram; 0.56 mmol; 0.2 moleqs) and EDC·HCl (2.65 gram, 13.8 mmol, 2.4 moleqs) as coupling reagents. Work-up by extraction/washing steps followed by silica column chromatography. Yield: 2.27 g (90%). The $^1$H-NMR spectrum was in agreement with the desired structure.

$^1$H NMR (400 MHz, Chloroform-d) δ 4.75 (s, 4H, $OCCH_2OCO$), 2.42 (t, J=7.5 Hz, 4H, $CH_2CH_2COO$), 1.67 (q, J=7.4 Hz, 4H, $CH_2CH_2COO$), 1.50-1.07 (m, 32H, $CH_3(CH_2)_8CH_2$), 1.07-0.64 (m, 6H, $CH_3CH_2$).

Step 2: 2-Hydroxypropane-1,3-diyl di-dodecanoate

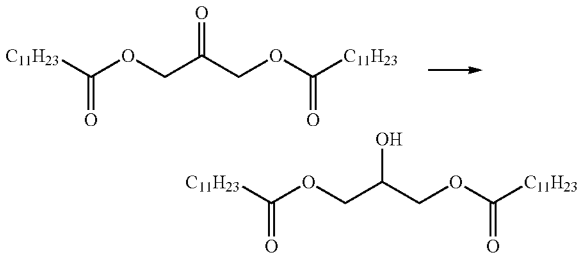

This compound was obtained via the reduction of 2-oxopropane-1,3-diyl di-dodecanoate (1.54 gram; 3.37 mmol) with sodium boron hydride (229 mg; 7.9 mmol; 2.4 moleqs) in THF (45 mL) and water (3 mL). The sodium boron hydride was added to a cooled solution of the ketone in THF/water (0° C. ice bath). The reaction mixture was stirred for 2 hours after which the reaction was quenched by the addition of acetic acid (1 mL). The reaction mixture was diluted with chloroform (50 mL) and was washed with a saturated $Na_2CO_3$ solution and a saturated NaCl solution. The organic layer was dried with $Na_2SO_4$. The crude product was then purified via silica column chromatography using 2% acetone in chloroform as eluent. A pure fraction of product was obtained (440 mg; 28% yield), as well as impure fractions. The $^1$H-NMR spectrum was in agreement with the desired structure.

$^1$H NMR (400 MHz, Chloroform-d) δ 4.31-4.01 (m, 5H, $OCH_2CH(OH)CH_2O$), 2.42 (d, J=4.8 Hz, 1H, OH), 2.35 (t, J=7.6 Hz, 4H, $CH_2CH_2COO$), 1.74-1.58 (m, 4H, $CH_2CH_2COO$), 1.27 (d, J=12.5 Hz, 32H, $CH_3(CH_2)_8CH_2$), 0.88 (t, J=6.8 Hz, 6H, $CH_3CH_2$).

Step 3: 2-((3-(Dimethylamino)propanoyl)oxy)propane-1,3-diyl di-dodecanoate

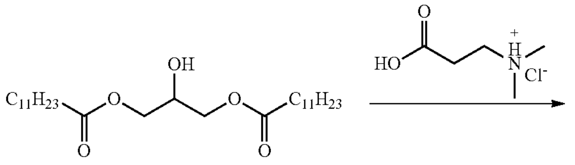

-continued

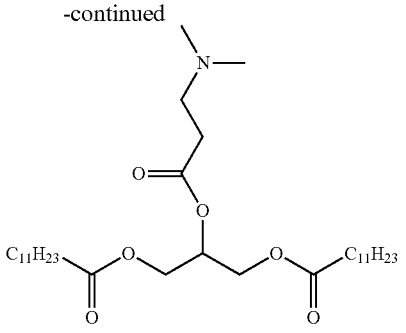

The reaction between 2-hydroxypropane-1,3-diyl di-dodecanoate and 3-(dimethylamino)propanoic acid hydrochloride was performed in a similar way as done for the preparation of Subexample 1 (step 2). Yield: 165 mg (68%). The $^1$H-NMR spectrum was in agreement with the desired structure.

$^1$H NMR (400 MHz, Chloroform-d) δ 5.28 (tt, J=5.8, 4.4 Hz, 1H, $OCH_2CHCH_2O$), 4.30-4.16 (m, 4H, $CHCH_2OCO$), 2.61 (td, J=7.1, 1.1 Hz, 2H, $(CH_3)_2NCH_2CH_2COO$), 2.50 (ddd, J=7.9, 6.9, 1.1 Hz, 2H, $(CH_3)_2NCH_2CH_2COO$), 2.31 (t, J=7.6 Hz, 4H, $CH_2CH_2COO$ of the $C_{11}$ tails), 2.23 (s, 6H, $N(CH_3)_2$), 1.62 (q, J=7.1 Hz, 4H, $CH_2CH_2COO$), 1.27 (d, J=8.7 Hz, 32H, $CH_3(CH_2)_8CH_2$), 0.99-0.71 (m, 6H, $CH_3CH_2$).

MALDI-TOF-MS (CHCA matrix, positive reflector mode): m/z $(M+H)^+$=556.46. Calculated: $C_{32}H_{61}NO_6$ (exact mass 555.45; molecular weight 555.84).

Example for Formula (II) (ICG-B Type): 1,2 Glycerol Ionizable Cationic Lipids

Subexample 11: (R)-3-((5-Guanidinopentanoyl)oxy)propane-1,2-diyl di-dodecanoate

Step 1: (Z)-5-(2,3-Bis(tert-butoxycarbonyl)guanidino)pentanoic acid

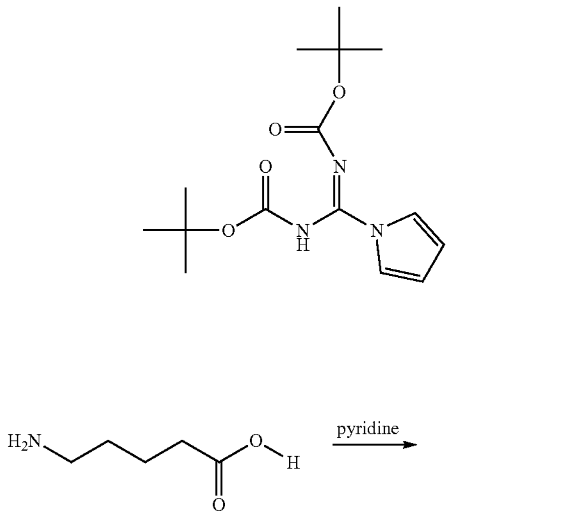

-continued

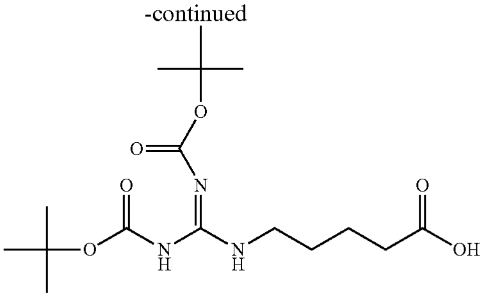

The reaction between tert-butyl (E)-(((tert-butoxycarbonyl)imino)(1H-pyrrol-1-yl)methyl)carbamate (0.5 gram; 4.25 mmol) and 5-aminopentanoic acid (1.45 gram; 4.68 mmol; 1.1 moleqs) was performed in pyridine (10 mL) at room temperature for 48 hours. The reaction mixture suspension developed into a clear solution. The mixture was evaporated to dryness, and the residue was dissolved in 1 M NaOH (25 mL) and was washed with EtOAc (50 mL). The water layer was acidified to a pH of 3 using a concentrated HCl solution. The water layer was extracted two times with EtOAc, and the collected organic layers were first washed with a saturated NaCl-solution and then dried with $Na_2SO_4$. Evaporation of the solvent gave a white solid (1.22 gram). This crude product was further purified by stirring it in a mixture of 1/3 EtOAc/Heptane with added drops of acetic acid (about 0.2 v/v %). The $^1$H-NMR spectrum was in agreement with the desired structure.

$^1$H NMR (400 MHz, Chloroform-d) δ 8.35 (t, J=5.3 Hz, 1H), 3.73-3.15 (m, 2H, $NCH_2CH_2$), 2.40 (t, J=7.0 Hz, 2H, $CH_2CH_2COOH$), 1.83-1.57 (m, 4H. $NCH_2CH_2CH_2CH_2COOH$), 1.50 (d, J=2.3 Hz, 18H, $CH_3$ Boc).

HPLC-MS: m/z $(M+H)^+$=359.92. Calculated: $C_{16}H_{29}N_3O_6$ (exact mass 359.21; molecular weight 359.42).

Step 2: (R,E)-6-((tert-Butoxycarbonyl)amino)-2,2-dimethyl-4,12-dioxo-3,13-dioxa-5,7-diazahexadec-5-ene-15,16-diyl di-dodecanoate

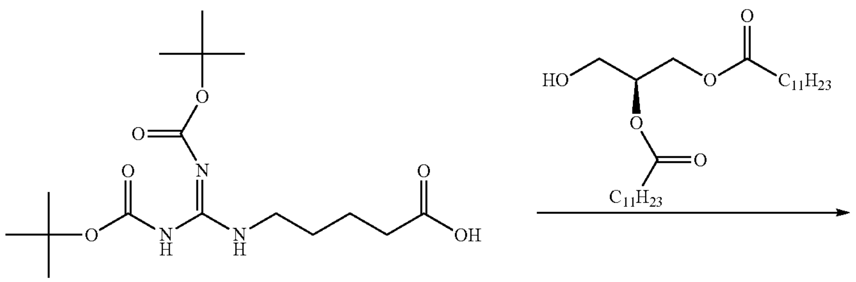

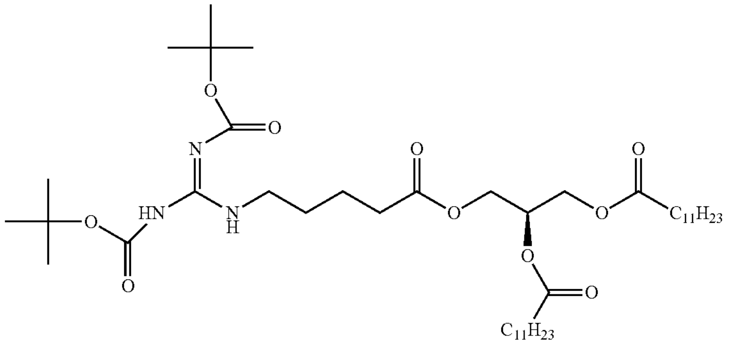

The reaction between (Z)-5-(2,3-bis(tert-butoxycarbonyl) guanidino)pentanoic acid (0.43 gram; 1.2 mmol; 1.1 moleqs) and (S)-3-hydroxypropane-1,2-diyl di-dodecanoate (Building Block 1; 0.5 gram; 1.1 mmol) was performed in DCM (4 mL) using DIC (0.15 g; 1.2 mmol; 1.1 moleqs) and DPTS (32 mg; 0.11 mmol; 0.1 moleqs) as reagents. The mixture was stirred at room temperature for 72 hours. The mixture was diluted with DCM (25 mL) and was then subsequently washed with 1M NaOH (25 mL) and by a saturated NaCl (aq) solution. The solution was dried with $Na_2SO_4$. The crude product was purified by silica column chromatography with EtOAc/Heptane (1/3) as eluent. Yield: 0.471 g (54%). The $^1$H-NMR spectrum was in agreement with the desired structure.

$^1$H NMR (400 MHz, Chloroform-d) δ 11.50 (s, 1H, NH), 8.32 (t, J=5.2 Hz, 1H, NH), 5.26 (tt, J=6.0, 4.3 Hz, 1H, $OCH_2CHCH_2O$), 4.30-4.14 (m, 4H, $CHCH_2OCO$), 3.43 (td, J=6.9, 5.2 Hz, 2H, $NCH_2(CH_2)_2CH_2COO$), 2.59-2.20 (m, 6H, $CH_2CH_2COO$ of the $C_{11}$ tails, $NCH_2(CH_2)_2CH_2COO$), 1.84-1.56 (m, 8H, $NCH_2CH_2CH_2CH_2COOH$, $CH_2CH_2COO$), 1.50 (d, J=3.9 Hz, 18H, $CH_3$ Boc), 1.27 (d, J=9.2 Hz, 32H, $CH_3(CH_2)_8CH_2$), 1.11-0.64 (m, 8H, $CH_3$).

Step 3: (R)-3-((5-Guanidinopentanoyl)oxy)propane-1,2-diyl di-dodecanoate $NCH_2CH_2CH_2CH_2COO$, $CH_2CH_2COO$), 1.27 (d, J=9.0 Hz, 32H, $CH_3(CH_2)_8CH_2$), 0.88 (t, J=6.7 Hz, 6H, $CH_3$).

MALDI-TOF-MS (CHCA matrix, positive reflector mode): m/z $(M+H)^+$=598.46. Calculated: $C_{33}H_{63}N_3O$ (exact mass 597.47; molecular weight 597.88).

Example for Formula (IV) (ICG-A Type): Serinol-Derived Type of Ionizable Cationic Lipids Subexample 12: 2-(4-(Dimethylamino)butanamido)-2-methylpropane-1,3-diyl di-dodecanoate Step 1: tert-Butyl (1,3-dihydroxy-2-methylpropan-2-yl)carbamate

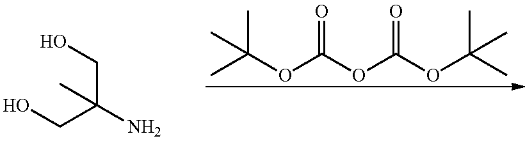

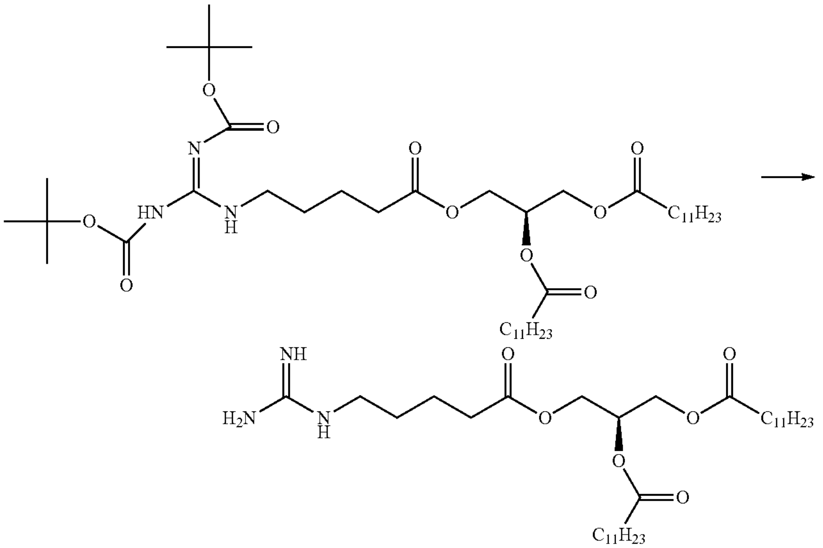

(R,E)-6-((tert-Butoxycarbonyl)amino)-2,2-dimethyl-4,12-dioxo-3,13-dioxa-5,7-diazahexadec-5-ene-15,16-diyl di-dodecanoate (0.471 gram; 0.6 mmol) was deprotected with TFA in DCM at room temperature for 24 hours. The reaction mixture was evaporated and coevaporated several times with DCM to remove the excess of TFA. The product was diluted in chloroform and first washed with a 0.05M NaOH solution (25 mL) and then with a saturated NaCl (aq) solution. The organic layer was dried with $Na_2SO_4$, and the solution was concentrated to afford the product. Yield: 0.35 g (100%). The $^1$H-NMR spectrum was in agreement with the desired structure.

$^1$H NMR (400 MHz, Chloroform-d) δ 5.27 (td, J=6.1, 3.0 Hz, 1H, $OCH_2CHCH_2O$), 4.49-4.00 (m, 4H, $CHCH_2OCO$), 3.21 (q, J=6.8, 6.1 Hz, 2H, $NCH_2(CH_2)_2CH_2COO$), 2.57-2.26 (m, 6H, $CH_2CH_2COO$ of the $C_{11}$ tails, $NCH_2(CH_2)_2CH_2COO$), 1.88-1.48 (m, 8H, -continued

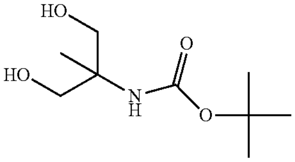

2-Amino-2-methylpropane-1,3-diol (5 gram; 48 mmol) was reacted with BOC-anhydride (8 gram; 96 mmol; 2 moleqs) in a mixture of methanol (120 mL) and THF (30 mL). The BOC-anhydride solution was added dropwise to the reaction mixture that was cooled in an ice bath (0° C.). The reaction mixture was stirred for 24 hours at room temperature, and was then concentrated. The residue was dissolved in EtOAc, washed three times with demi water and dried with $Na_2SO_4$. The crude product was recrystallized from EtOAc. Yield: 3.5 g (36%). The $^1$H-NMR spectrum was in agreement with the desired structure.

$^1$H NMR (400 MHz, Chloroform-d) δ 4.98 (s, 1H, NH), 3.78-3.62 (m, 4H, $OCOCH_2CCH_2OCO$), 3.52 (s, 2H, OH), 1.44 (s, 9H, $CH_3$ Boc), 1.17 (s, 3H, $NCCH_3$).

Step 2: 2-((tert-Butoxy-carbonyl)amino)-2-methyl-propane-1,3-diyl di-dodecanoate

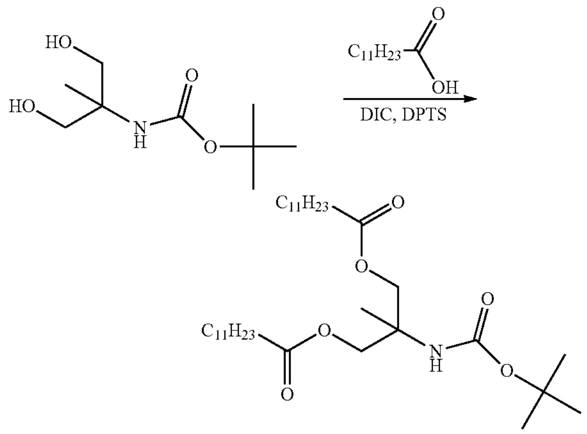

tert-Butyl (1,3-dihydroxy-2-methylpropan-2-yl)carbamate (0.5 gram; 2.43 mmol) was coupled to dodecanoic acid (1.02 gram; 5.1 mmol; 2.1 moleqs) in DCM (4 mL) using DPTS (70 mg; 0.24 mmol; 0.1 moleqs) and DIC (0.77 gram; 41.2 mmol; 6.1 moleqs) as reagents. After stirring the reaction mixture for 24 hours at room temperature, it was filtrated over a plug of celite. The filtrate was diluted with DCM (25 mL), and was then washed with 0.1M HCl (25 mL), 0.1M NaOH (25 mL) and a saturated NaCl (aq) solution (25 mL). The solution was dried with $Na_2SO_4$. Further purification was done via silica column chromatography using EtOAc/Hept 1/20 as eluent. Yield: 1.13 g (82%). The $^1$H-NMR spectrum was in agreement with the desired structure.

$^1$H NMR (400 MHz, Chloroform-d) δ 4.73 (s, 1H, NH), 4.42-3.96 (m, 4H, $OCOCH_2CCH_2OCO$), 2.33 (t, J=7.5 Hz, 4H, $CH_2CH_2COO$ of the $C_{11}$ tails), 1.62 (p, J=7.7 Hz, 4H, $CH_2CH_2COO$), 1.52 (s, 9H, $CH_3$ Boc), 1.36 (s, 3H, $NCCH_3$), 1.33-1.09 (m, 32H, $CH_3(CH_2)_8CH_2$), 0.88 (t, J=6.7 Hz, 6H, $CH_3$).

Step 3: 2-Amino-2-methylpropane-1,3-diyl di-dodecanoate

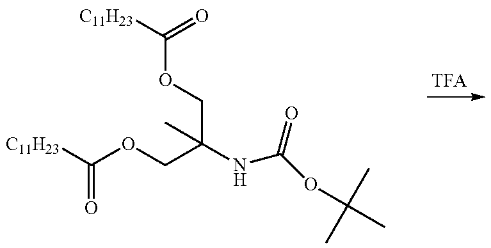

-continued

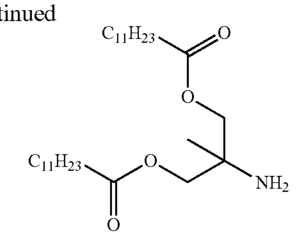

(2-((tert-Butoxy-carbonyl)amino)-2-methylpropane-1,3-diyl di-dodecanoate (1.13 gram; 1.98 mmol) was stirred in TFA (2 mL) and DCM (4 mL) at room temperature for 24 hours. The solvents were evaporated, the crude product residue (a white solid) was redissolved in chloroform, and the organic solution was subsequently washed with 1.0M NaOH (25 mL) and a saturated NaCl (aq) solution. After drying in $Na_2SO_4$ the product was isolated. Yield: 0.853 g (91%). The $^1$H-NMR spectrum was in agreement with the desired structure.

$^1$H NMR (400 MHz, Chloroform-d) b 3.94 (q, J=10.9 Hz, 4H, $OCOCH_2CCH_2OCO$), 2.33 (t, J=7.6 Hz, 4H, $CH_2CH_2COO$ of the $C_{11}$ tails), 1.63 (q, J=7.2 Hz, 4H, $CH_2CH_2COO$), 1.27 (d, J=11.9 Hz, 32H, $CH_3(CH_2)_8CH_2$), 1.12 (s, 3H, $NCCH_3$), 0.88 (t, J=6.7 Hz, 6H, $CH_3$).

MALDI-TOF-MS (CHCA matrix, positive reflector mode): m/z $(M+H)^+$=470.43, $(M+Na)^+$=492.41. Calculated: $C_{28}H_{55}NO_4$ (exact mass 469.41; molecular weight 469.75).

Step 4: 2-(4-(Dimethylamino)butanamido)-2-methylpropane-1,3-diyl di-dodecanoate

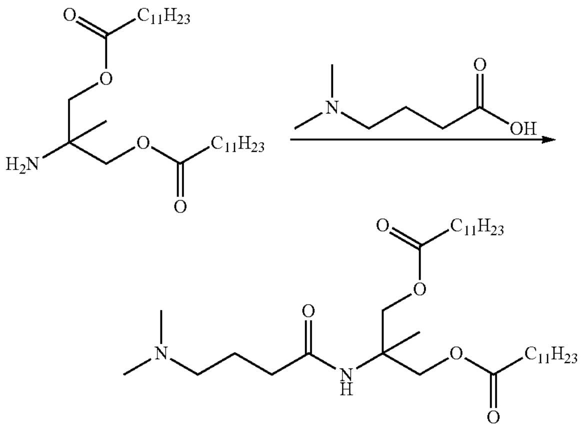

2-Amino-2-methylpropane-1,3-diyl di-dodecanoate (0.32 gram; 0.68 mmol) was coupled to 4-(dimethylamino)butanoic acid hydrochloride (0.17 gram; 1.02 mmol; 1.5 moleqs) in DCM (2 mL) using DPTS (20 mg; 0.24 mmol; 0.07 moleqs) and DIC (0.127 gram; 1.01 mmol; 1.5 moleqs) as reagents. The reaction mixture was stirred for 24 hours at room temperature, after which it was filtrated over a plug of celite. The filtrate was diluted with DCM (25 mL), washed with 0.1M HCl (25 mL), 0.1M NaOH (25 mL), saturated NaCl (aq) (25 mL), and finally dried with $Na_2SO_4$. The crude product was purified via silica column chromatography using a 2% MeOH/chloroform to 10% MeOH/chloroform eluent gradient. Yield: 294 mg (75%). The $^1$H-NMR spectrum was in agreement with the desired structure.

$^{1}H$ NMR (400 MHz, Chloroform-d) δ 6.86 (s, 1H, NH), 4.50-4.09 (m, 4H, $OCOCH_2CCH_2OCO$), 2.40 (t, J=6.6 Hz, 2H. $CH_2N(CH_3)_2$), 2.36-2.16 (m, 10H, $NCOCH_2$, $OCOCH_2$ and $CH_2N(CH_3)_2$), 1.79 (q, J=6.8 Hz, 2H, $CH_2CH_2N(CH_3)_2$), 1.75-1.54 (m, 4H, $CH_2CH_2COO$), 1.39 (s, 3H, $NCCH_3$), 1.27 (d, J=9.1 Hz, 32H, $CH_3(CH_2)_8CH_2$), 1.12-0.52 (m, 6H, $CH_3$).

MALDI-TOF-MS (CHCA matrix, positive reflector mode): m/z $(M+H)^+$=583.47, $(M+Na)^+$=605.46. Calculated: $C_{34}H_{66}N_2O_5$ (exact mass 582.50; molecular weight 582.91).

Examples for Formula (V) (ICG-A Type): Cholesteryl Ionizable Cationic Lipids

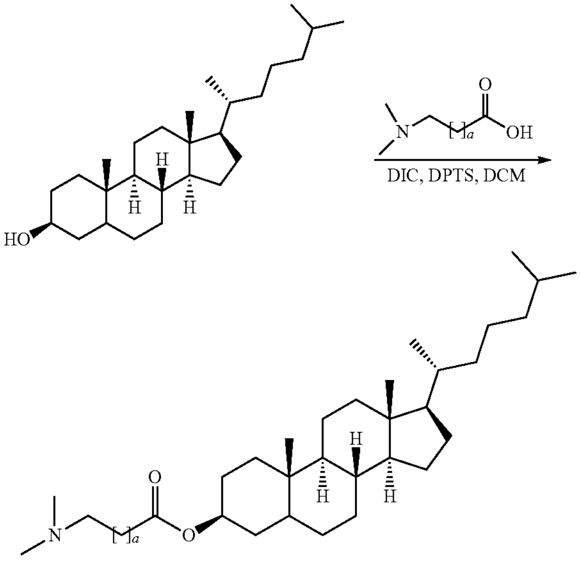

a = 0, 1, 2

Scheme B: Synthetic Route to Cholesteryl Ionizable Cationic Lipids as According to Formula (V) with ICG-A type. DPTS=4-(dimethyl-amino)-pyridinium 4-toluene-sulfonate; DIC=N,N-di-isopropyl-carbodiimide; DCM=dichloromethane Subexample 13: (3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-(dimethylamino)butanoate

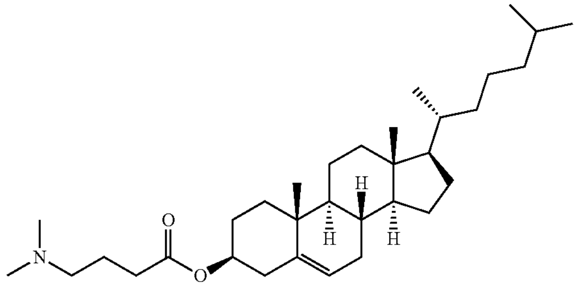

Cholesterol (0.30 g; 0.77 mmol) was reacted with 4-(dimethylamino)butanoic acid hydrochloride (0.195 gram; 1.16 mmol; 1.5 moleqs) in DCM (2 mL) using DPTS (21.7 milligram; 0.077 mmol; 0.1 moleqs) and DIC (0.15 gram; 1.16 mmol; 1.5 moleqs) as reagents. The reaction mixture was stirred for 24 hours at room temperature, after which it was filtrated over a plug of celite. The filtrate was diluted with DCM (25 mL), washed with 0.1M NaOH (25 mL) and saturated NaCl (aq) (25 mL), and finally dried with $Na_2SO_4$. The crude mixture was precipitated from chloroform (1.5 mL) into acetonitrile (50 mL) at 0° C. The product precipitate was collected by filtration, washed with cold acetonitrile and dried at 40° C. Yield: 165 mg (42%).

$^{1}H$ NMR (400 MHz, Chloroform-d) δ 5.37 (d, J=5.0 Hz, 1H, $C{=}CHCH_2$), 4.71-4.49 (m, 1H, $CH_2CHCOO$), 2.37-2.25 (m, 6H, $CH_2N(CH_3)_2$, $CH{=}CCH_2CHCOO$, $CH_2COO$), 2.22 (s, 6H, $CH_2N(CH_3)_2$), 2.08-1.91 (m, 2H,), 1.91-1.71 (m, 5H), 1.57-1.41 (m, 6H), 1.34 (d, J=8.2 Hz, 3H), 1.26 (d, J=10.9 Hz, 1H), 1.22-1.05 (m, 7H), 1.02 (s, 5H), 0.99-0.94 (m, 2H), 0.91 (d, J=6.5 Hz, 3H), 0.86 (dd, J=6.6, 1.8 Hz, 6H), 0.68 (s, 3H). The $^{1}H$-NMR spectrum was in agreement with the desired structure.

HPLC-MS: m/z $(M+H)^+$=500.42. Calculated: $C_{33}H_{57}NO_2$ (exact mass 499.44; molecular weight 499.82).

Subexample 14: (3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(dimethylamino)propanoate

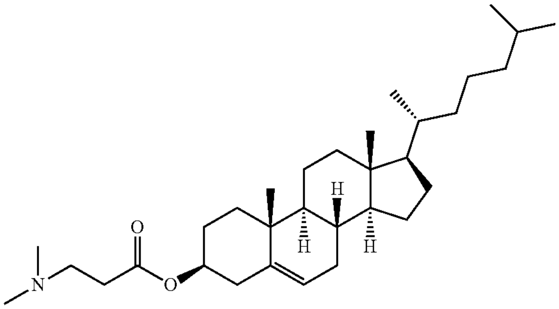

A similar procedure as described in Example 13 was employed to couple cholesterol (0.097 gram; 0.25 mmol) to 3-(dimethyl-amino)propanoic acid hydrochloride (0.058 gram; 0.375 mmol; 1.5 moleqs). Yield: 76 mg (63%). The $^{1}H$-NMR spectrum was in agreement with the desired structure.

$^{1}H$ NMR (400 MHz, Chloroform-d) δ 5.37 (d, J=4.9 Hz, 1H), 4.62 (t, J=5.9 Hz, 1H), 2.67-2.56 (m, 2H), 2.51-2.41 (m, 2H), 2.32 (d, J=7.5 Hz, 2H), 2.24 (s, 6H), 2.05-1.91 (m, 2H), 1.84 (tt, J=9.5, 4.2 Hz, 3H), 1.66-1.42 (m, 9H), 1.42-1.23 (m, 4H), 1.23-1.04 (m, 7H), 1.02 (s, 4H), 0.96 (dd, J=11.3, 5.3 Hz, 2H), 0.91 (d, J=6.5 Hz, 3H), 0.86 (dd, J=6.6, 1.8 Hz, 6H), 0.68 (s, 3H).

HPLC-MS: m/z $(M+H)^+$=486.33. Calculated: $C_{32}H_{55}NO_2$ (exact mass 485.42; molecular weight 485.80).

Subexample 15: (3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl dimethylglycinate

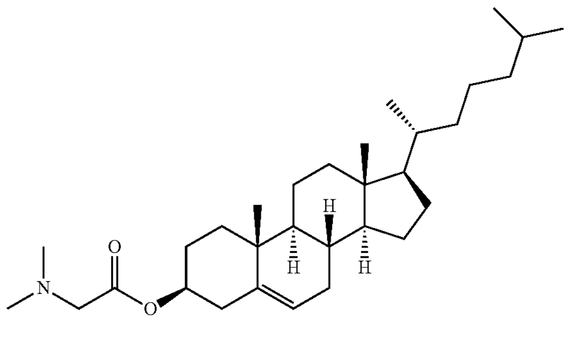

A similar procedure as described in Example 13 was employed to couple cholesterol (0.193 gram; 0.5 mmol) to dimethyl-glycine hydrochloride (0.077 gram; 0.75 mmol; 1.5 moleqs). Yield: 147 mg (63%). The $^1$H-NMR spectrum was in agreement with the desired structure.

$^1$H NMR (400 MHz, Chloroform-d) δ 5.38 (d, J=5.1 Hz, 1H), 4.78-4.61 (m, 1H), 3.14 (s, 2H), 2.35 (s, 8H), 2.08-1.92 (m, 2H), 1.92-1.75 (m, 3H), 1.72-1.41 (m, 10H), 1.30 (dd, J=31.8, 9.6 Hz, 4H), 1.23-1.04 (m, 7H), 1.02 (s, 4H), 0.99-0.94 (m, 2H), 0.91 (d, J=6.5 Hz, 3H), 0.86 (dd, J=6.6, 1.8 Hz, 6H), 0.68 (s, 3H).

HPLC-MS: m/z $(M+H)^+$=472.17. Calculated: $C_{31}H_{53}NO_2$ (exact mass 471.41; molecular weight 471.77).

Figure 10:
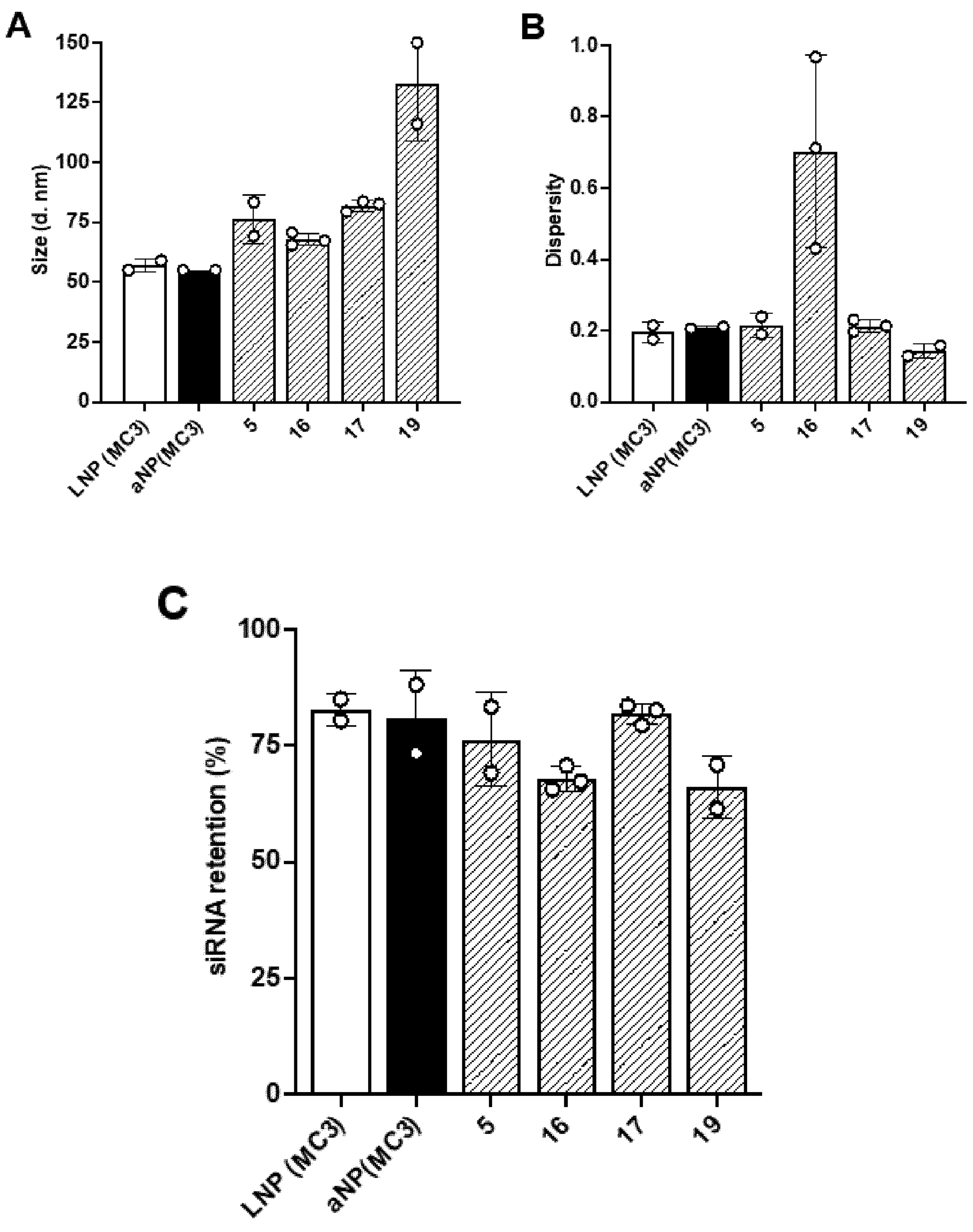
FIG. 10: Apolipoprotein lipid nanoparticles (aNP) containing siRNA (siRNA-aNP) according to certain embodiments of the invention can be prepared with various ionizable cationic materials to yield stable formulations. siRNA-aNP formulations that contained phospholipids, cholesterol, ionizable cationic materials as depicted in FIG. 9 (ionizable cationic lipids 5, 16, 17 and 19 are the molecules of Examples 10, 13, 9 and 8, respectively, as shown in FIG. 9), triglycerides, apolipoprotein A1 and siRNA. siRNA-aNP formulations were produced using the procedure described in FIG. 2. One day after formulating, the library's individual siRNA-aNP formulations and the LNP-siRNA comparative example formulations# were analyzed for: (A) particle size and (B) particle size dispersity using dynamic light scattering (DLS), and (C) siRNA retention using Ribogreen assay. #The LNP-siRNA comparative example is composed of Dlin-MC3-DMA, DSPC, cholesterol and PEG-DMG (50:38.5:10:1.5 mol %), with included siRNA.

Example 10. Apolipoprotein Lipid Nanoparticles (aNP) Containing siRNA (siRNA-aNP) can be Prepared with Various Ionizable Cationic Materials to Yield Stable Formulations (FIG. 10)

siRNA-aNP formulations that contained phospholipids, cholesterol, selected ionizable cationic materials as depicted in FIG. 9, triglycerides, apolipoprotein A1 and siRNA. siRNA-aNP formulations were produced using the procedure described in Example 2. One day after formulating, the library's individual siRNA-aNP formulations and the LNP-siRNA comparative example formulations# were analyzed for: (A) particle size and (B) particle size dispersity using dynamic light scattering (DLS), and (C) siRNA retention using Ribogreen assay. #The LNP-siRNA comparative example was composed of Dlin-MC3-DMA, DSPC, cholesterol and PEG-DMG (50:38.5:10:1.5 mol %), with included siRNA.

In addition, non-optimized siRNA-aNP formulations of ionizable cationic materials 17 and 19 were tested and showed moderate (about 50%) silencing capability in murine RAW264.7 macrophages transfected with the pmirGLO plasmid (Promega) for stable dual reporter luciferase expression (Firefly and Renilla luciferase).

The invention claimed is:

1. A nanoparticle comprising a core surrounded by a surface layer, wherein:

the core comprises a nucleic acid and a cationic or ionizable cationic lipid; and the surface layer is a monolayer comprising:

a phospholipid, a sterol, and an apolipoprotein or an apolipoprotein mimetic or a combination thereof.

2. The nanoparticle according to claim 1, wherein the apolipoprotein, apolipoprotein mimetic, or the combination thereof is located on the outer surface of the surface layer.

3. The nanoparticle according to claim 1, wherein the nanoparticle core further comprises a filler.

4. The nanoparticle according to claim 1, wherein the nucleic acid is RNA, DNA or a nucleic acid analogue.

5. The nanoparticle according to claim 4, wherein the RNA is microRNA (miRNA), small interfering RNA (siRNA), piwi-interacting RNA (piRNA), small nuclear RNA (snoRNA), transfer RNA (tRNA), tRNA-derived small RNA (tsRNA), small regulatory RNA (srRNA), messenger RNA (mRNA), modified mRNA, ribosomal RNA (rRNA), long non-coding RNA (lncRNA) or guide RNA (gRNA) or combinations thereof and/or modifications thereof.

6. The nanoparticle according to claim 4, wherein the DNA is single stranded or double stranded DNA.

7. The nanoparticle according to claim 1, wherein the nucleic acid is an antisense oligonucleotide and the antisense oligonucleotide is single strand DNA or RNA consisting of nucleotide or nucleoside analogues containing modifications of the phosphodiester backbone or the 2' ribose.

8. The nanoparticle according to claim 7, wherein the nucleotide or nucleoside analogues are selected from locked nucleic acid (LNA), bridged nucleic acid (BNA), morpholino or peptide nucleic acid (PNA).

9. The nanoparticle according to claim 1, wherein the apolipoprotein is selected from ApoA1, ApoA1-Milano, ApoA2, ApoA4, ApoA5, ApoB48, ApoB100, ApoC-I, ApoC-II, ApoC-III, ApoC-IV, ApoD, ApoE, ApoF, ApoH, ApoL, ApoM, and combinations thereof.

10. The nanoparticle according to claim 9, wherein the apolipoprotein is selected from ApoA1, ApoA2, ApoA4, ApoA5, ApoB100, ApoC-I, ApoC-II, ApoC-III, ApoC-IV, ApoE, and combinations thereof.

11. The nanoparticle according to claim 9, wherein the apolipoprotein is selected from ApoA1, ApoA4, ApoA5, ApoB100, ApoC-III, ApoE, and combinations thereof.

12. The nanoparticle according to claim 9, wherein the apolipoprotein is selected from ApoA1, ApoB100, ApoE, and combinations thereof.

13. The nanoparticle according to claim 1, wherein the cationic or ionizable cationic lipid is selected from an ionizable cationic ester of a long chain alcohol, an ionizable cationic ester of a diglyceride or an ionizable cationic ester of a sterol or combinations thereof.

14. The nanoparticle according to claim 1, wherein the ionizable cationic lipid is a molecule according to any one of Formulae (I), (II), (III), (IV) or (V)

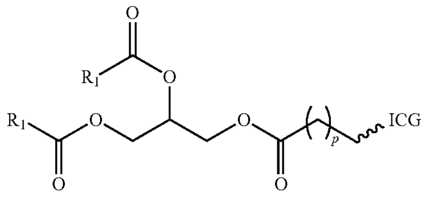
(I)

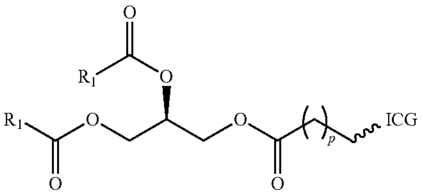
(II)

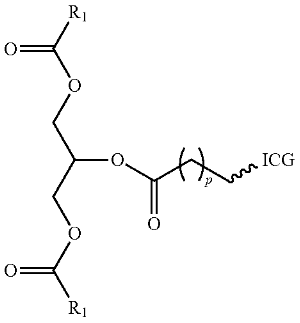
(III)

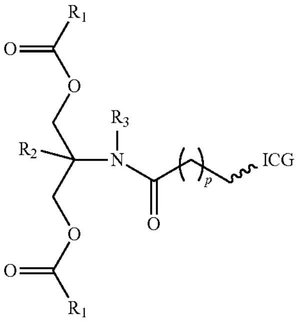
(IV)

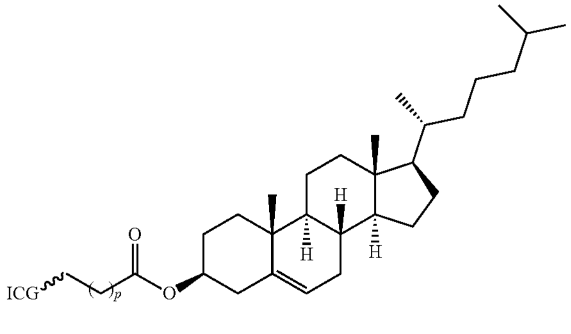
(V)

wherein ICG is

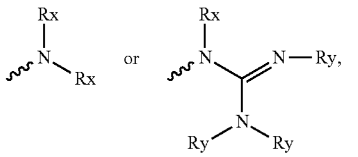

wherein the wavy line indicates the point of attachment to the compound of formulae (I), (II), (III), (IV) or (V);

p is an integer selected from 0, 1, 2, 3, 4, 5, 6, 7, 8, 9, 10 and 11;

each $R_1$ is independently selected from the group consisting of linear or branched C1-C19 alkyl, linear or branched C1-C19 alkenyl, aryl, arylene-alkyl and alkylene-aryl group, wherein said alkyl or alkenyl group optionally contains up to 5 heteroatoms, independently selected from O and N;

$R_2$ is selected from the group consisting of hydrogen, methyl, ethyl and a $—CH_2—O—C(O)—R_{1a}$;

$R_3$ is selected from the group consisting of hydrogen, aryl, arylene-alkyl, alkylene-aryl and linear C1-C6 alkyl group;

$R_{1a}$ is selected from the group consisting of linear or branched C1-C19 alkyl, linear or branched C1-C19 alkenyl, aryl, arylene-alkyl and alkylene-aryl group, wherein said alkyl or alkenyl group optionally contains up to 5 heteroatoms, independently selected from O and N;

each $R_x$ is independently selected from the group consisting of methyl, ethyl, propyl and $—CH_2—CH_2—OH$;

each $R_y$ group is independently selected from the group consisting of hydrogen, linear or branched C1-C18 alkyl, aryl, arylene-alkyl or alkylene-aryl group, wherein said alkyl group optionally contains up to 5 heteroatoms, independently selected from O and N;

or rotamers, tautomers stereoisomers or regioisomers thereof.

15. The nanoparticle according to claim 1, wherein the sterol is selected from cholesterol, desmosterol, stigmasterol, β-sitosterol, ergosterol, hopanoids, hydroxysteroid, phytosterol, steroids, hydrogenated cholesterol, campesterol, zoosterol, or combinations thereof.

16. The nanoparticle according to claim 1, wherein:

the phospholipid is selected from a phosphatidylcholine (PC), a phosphatidylethanolamine (PE), a phosphatidylserine and a phosphatidylglycerol or combinations thereof.

17. The nanoparticle according to claim 16, wherein at least one or both, of the acyl groups in the phospholipid are long chain fatty acids.

18. The nanoparticle according to claim 17, wherein said long chain fatty acids are selected from myristoleic acid, palmitoleic acid and oleic acid or combinations thereof.

19. The nanoparticle according to claim 1, wherein the phospholipid is selected from the group consisting of dilauroylphosphatidylcholine (DLPC), dimyristoylphosphatidylcholine (DMPC), dipalmitoylphosphatidylcholine (DPPC), distearoylphosphatidylcholine (DSPC), dioleoylphosphatidylcholine (DOPC), dilauroylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dilauroyl phosphatidylethanolamine (DLPE), dimyristoyl phosphatidylethanolamine (DMPE), dipalmitoyl phosphatidylethanolamine (DPPE), distearoyl phosphatidylethanolamine (DSPE), dilauroyl phosphatidylserine (DLPS), dimyristoyl phosphatidylserine (DMPS), dipalmitoyl phosphatidylserine (DPPS), distearoyl phosphatidylserine (DSPS), 1-palmitoyl-2-oleoyl-sn-glycero-3-phosphocholine (POPC), 1,2-dioleoyl-sn-glycero-3-phosphoethanolamine (DOPE), or combinations thereof.

20. The nanoparticle according to claim 1, wherein:

the amount of apolipoprotein ranges from 0.08 to 2.0 mol %, or from 0.10 to 2.0 mol %; and/or the amount of phospholipid ranges from 5 to 90 mol %, or from 15 to 90 mol %; and/or the amount of sterol ranges from 2.5 to 65 mol %, or from 2.5 to 50 mol %; and/or the amount of cationic or ionizable cationic lipid ranges from 5.0 to 80 mol %, or from 8.0 to 80 mol %, wherein the molar percentage is based solely on the combined amounts of the apolipoprotein, phospholipids, sterols and cationic or ionizable cationic lipids in the nanoparticle.

21. The nanoparticle according to claim 1, wherein the amount of apolipoprotein and/or apolipoprotein mimetic ranges from 0.1 to 90 weight %;

the amount of nucleic acid ranges from 0.01 to 90 weight %;

the amount of phospholipid ranges from 0.1 to 95 weight %;

the amount of sterol ranges from 0.1 to 95 weight %; and/or the amount of cationic and/or ionizable cationic lipid ranges from 0.1 to 95 weight %, wherein these weight percentages are based on the combined amounts of the apolipoprotein and/or apolipoprotein mimetic, the nucleic acid, the phospholipid, the sterol and the cationic and/or ionizable cationic lipid.

22. The nanoparticle according to claim 1, wherein the ratio of apolipoprotein to phospholipid based on percentage molar weight is between 1:25 and 1:400, or between 1:50 and 1:200, or between 1:75 and 1:150.

23. The nanoparticle according to claim 1, wherein the ratio of apolipoprotein to phospholipid based on weight is from 2:1 to 1:10, or from 1:1 to 1:5, or from 1:1.5 to 1:4.

24. The nanoparticle according to claim 1, having an average size of 10 to 100 nm, or from 30 to 100 nm.

25. A composition comprising the nanoparticle according to claim 1 and a physiologically acceptable carrier.

26. The composition according to claim 25, wherein the composition is a pharmaceutical composition.

27. A method of delivering a nucleic acid to the myeloid compartment or the spleen of a subject, the method comprising administering the nanoparticle according to claim 1 to the subject.

28. A method of treating a disease by stimulating or inhibiting an innate immune response in a subject in need thereof, the method comprising administering a therapeutically effective amount of the nanoparticle according to claim 1 to the subject.

29. The method according to claim 28, wherein said disease is a cancer, a cardiovascular disease, an autoimmune disorder or xenograft rejection.

30. A method for producing a nanoparticle, comprising the step of:

a) rapid mixing of lipid components in organic solvent with a nucleic acid in an aqueous buffer to produce lipid nanoparticles, wherein the lipid components comprise a phospholipid, a sterol, a cationic lipid or ionizable cationic lipid, wherein the aqueous buffer has a pH of 5.0 or lower; and b) rapid mixing of the lipid nanoparticles with an apolipoprotein, an apolipoprotein mimetic, or a combination thereof to produce the nanoparticle at a pH between 6.0 and 8.0.

31. A nanoparticle that is obtainable or obtained by the method of claim 30.

32. An in vitro or ex vivo method for introducing a nucleic acid in a cell, the method comprising contacting the nanoparticle according to claim 1 with a cell.

33. An in vivo method for introducing a nucleic acid in a cell, the method comprising contacting the nanoparticle according to claim 1 with a cell.

34. A method for the in vivo delivery of a nucleic acid, the method comprising administering the nanoparticle according to claim 1 to a subject.

35. A method for treating a disease or disorder in a subject in need thereof by stimulating or inhibiting an innate immune response, the method comprising administering a therapeutically effective amount of the composition according to claim 25 to the subject.

36. The method according to claim 35, wherein the disease is selected from cancer, cardiovascular disease, autoimmune disorder or xenograft rejection.

37. The nanoparticle according to claim 1, wherein the nanoparticle core further comprises a filler selected from a triacylglyceride and a cholesterol acyl ester or combinations thereof.

38. The nanoparticle according to claim 37, wherein the triacylglyceride is tricaprylin and/or wherein the cholesterol acyl ester is cholesteryl caprylate and/or cholesteryl oleate.

* * * * *